US012335456B2

(12) United States Patent
Fisker et al.

(10) Patent No.: US 12,335,456 B2
(45) Date of Patent: *Jun. 17, 2025

(54) INTRAORAL SCANNING APPARATUS

(71) Applicant: 3SHAPE A/S, Copenhagen (DK)

(72) Inventors: Rune Fisker, Virum (DK); Henrik Öjelund, Lyngby (DK); Rasmus Kjær, Copenhagen (DK); Mike Van Der Poel, Rødovre (DK); Arish A. Qazi, Toronto (CA); Karl-Josef Hollenbeck, Copenhagen (DK)

(73) Assignee: 3SHAPE A/S, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/628,376

(22) Filed: Apr. 5, 2024

(65) Prior Publication Data

US 2024/0251068 A1  Jul. 25, 2024

Related U.S. Application Data

(63) Continuation of application No. 18/455,708, filed on Aug. 25, 2023, which is a continuation of application
(Continued)

(51) Int. Cl.
*H04N 13/296* (2018.01)
*A61B 5/00* (2006.01)
(Continued)

(52) U.S. Cl.
CPC ......... *H04N 13/296* (2018.05); *A61B 5/0068* (2013.01); *A61B 5/1077* (2013.01);
(Continued)

(58) Field of Classification Search
CPC .. H04N 13/296; A61B 5/0068; A61B 5/1077; A61B 5/1075; A61B 5/1076;
(Continued)

(56) References Cited

U.S. PATENT DOCUMENTS

| 1,051,002 A | 1/1913 | Peterson |
| 1,076,146 A | 10/1913 | Noyes |
(Continued)

FOREIGN PATENT DOCUMENTS

| CN | 1067573 A | 1/1993 |
| CN | 1906678 A | 1/2007 |
(Continued)

OTHER PUBLICATIONS

"221 Patent in View of Boerjes U.S. Pat. No. RE48,221,", D-1 Preliminary Invalidity Contentions, 17 pages.
(Continued)

*Primary Examiner* — Thai Q Tran
*Assistant Examiner* — Jose M Mesa
(74) *Attorney, Agent, or Firm* — Buchanan Ingersoll & Rooney PC

(57) ABSTRACT

A scanner includes a camera, a light source for generating a probe light incorporating a spatial pattern, an optical system for transmitting the probe light towards the object and for transmitting at least a part of the light returned from the object to the camera, a focus element within the optical system for varying a position of a focus plane of the spatial pattern on the object, unit for obtaining at least one image from said array of sensor elements, unit for evaluating a correlation measure at each focus plane position between at least one image pixel and a weight function, a processor for determining the in-focus position(s) of each of a plurality of image pixels for a range of focus plane positions, or each of a plurality of groups of image pixels for a range of focus plane positions, and transforming in-focus data into 3D real world coordinates.

19 Claims, 18 Drawing Sheets

Related U.S. Application Data

No. 17/892,397, filed on Aug. 22, 2022, now Pat. No. 11,831,815, which is a continuation of application No. 17/742,115, filed on May 11, 2022, now Pat. No. 11,671,582, which is a continuation of application No. 17/533,403, filed on Nov. 23, 2021, now Pat. No. 11,368,667, which is a continuation of application No. 17/340,806, filed on Jun. 7, 2021, now Pat. No. 11,622,102, which is a continuation of application No. 17/206,581, filed on Mar. 19, 2021, now Pat. No. 11,076,146, which is a continuation of application No. 16/774,843, filed on Jan. 28, 2020, now Pat. No. 11,051,002, which is a continuation of application No. 16/433,369, filed on Jun. 6, 2019, now Pat. No. 10,595,010, which is a continuation of application No. 16/217,943, filed on Dec. 12, 2018, now Pat. No. 10,326,982, which is a continuation of application No. 15/974,105, filed on May 8, 2018, now Pat. No. 10,349,041, which is a continuation of application No. 14/502,230, filed on Sep. 30, 2014, now Pat. No. 10,097,815, which is a continuation of application No. 13/376,427, filed as application No. PCT/DK2010/050148 on Jun. 17, 2010, now Pat. No. 8,878,905.

(60) Provisional application No. 61/231,118, filed on Aug. 4, 2009.

(51) Int. Cl.
*A61B 5/107* (2006.01)
*G01B 11/25* (2006.01)

(52) U.S. Cl.
CPC ...... *G01B 11/2513* (2013.01); *G01B 11/2518* (2013.01); *A61B 5/1075* (2013.01); *A61B 5/1076* (2013.01); *A61B 5/4547* (2013.01); *G01B 2210/58* (2013.01)

(58) Field of Classification Search
CPC .............. A61B 5/4547; G01B 11/2513; G01B 11/2518; G01B 2210/58
See application file for complete search history.

(56) References Cited

U.S. PATENT DOCUMENTS

| | | |
|---|---|---|
| 3,878,905 A | 4/1975 | Schaumann |
| 3,971,065 A | 7/1976 | Bayer |
| 4,291,958 A | 9/1981 | Frank et al. |
| 4,342,227 A | 8/1982 | Petersen et al. |
| 4,349,880 A | 9/1982 | Southgate et al. |
| 4,516,231 A | 5/1985 | Michaelis |
| 4,575,805 A | 3/1986 | Moermann et al. |
| 4,629,324 A | 12/1986 | Stern et al. |
| 4,640,620 A | 2/1987 | Schmidt |
| 4,781,448 A | 11/1988 | Chatenever et al. |
| 4,802,759 A | 2/1989 | Matsumoto et al. |
| 4,896,015 A | 1/1990 | Taboada et al. |
| 5,131,844 A | 7/1992 | Marinaccio et al. |
| 5,151,609 A | 9/1992 | Nakagawa et al. |
| 5,181,181 A | 1/1993 | Glynn |
| 5,269,325 A | 12/1993 | Robinson et al. |
| 5,339,154 A | 8/1994 | Gassler et al. |
| 5,372,502 A | 12/1994 | Massen et al. |
| 5,377,011 A | 12/1994 | Koch |
| 5,381,236 A | 1/1995 | Morgan |
| 5,428,450 A | 6/1995 | Vieillefosse et al. |
| 5,440,393 A | 8/1995 | Wenz |
| 5,455,899 A | 10/1995 | Forslund |
| 5,563,343 A | 10/1996 | Shaw et al. |
| 5,605,459 A | 2/1997 | Kuroda et al. |
| 5,615,003 A | 3/1997 | Hermary et al. |
| 5,675,407 A | 10/1997 | Geng |
| 5,702,249 A | 12/1997 | Cooper |
| 5,722,412 A | 3/1998 | Pflugrath et al. |
| 5,737,084 A | 4/1998 | Ishihara |
| 5,737,339 A | 4/1998 | Goto et al. |
| 5,766,006 A | 6/1998 | Murljacic |
| 5,850,289 A | 12/1998 | Fowler et al. |
| 5,851,113 A | 12/1998 | Jung et al. |
| 6,007,332 A | 12/1999 | Obrien |
| 6,026,189 A | 2/2000 | Greenspan |
| 6,072,496 A | 6/2000 | Guenter et al. |
| 6,081,739 A | 6/2000 | Lemchen |
| 6,135,961 A | 10/2000 | Pflugrath et al. |
| 6,148,120 A | 11/2000 | Sussman |
| 6,206,691 B1 | 3/2001 | Lehmann et al. |
| 6,227,850 B1 | 5/2001 | Chishti et al. |
| 6,229,913 B1 | 5/2001 | Nayar et al. |
| 6,249,616 B1 | 6/2001 | Hashimoto |
| 6,251,073 B1 | 6/2001 | Imran et al. |
| 6,259,452 B1 | 7/2001 | Coorg et al. |
| 6,263,234 B1 | 7/2001 | Engelhardt et al. |
| 6,334,773 B1 | 1/2002 | Ahlen et al. |
| 6,334,853 B1 | 1/2002 | Kopelman et al. |
| 6,361,489 B1 | 3/2002 | Tsai |
| 6,450,807 B1 | 9/2002 | Chishti et al. |
| 6,471,511 B1 | 10/2002 | Chishti et al. |
| 6,476,803 B1 | 11/2002 | Zhang et al. |
| 6,485,413 B1 | 11/2002 | Boppart et al. |
| 6,532,299 B1 | 3/2003 | Sachdeva et al. |
| 6,575,751 B1 | 6/2003 | Lehmann et al. |
| 6,592,371 B2 | 7/2003 | Durbin et al. |
| 6,645,148 B2 | 11/2003 | Nguyen-dinh et al. |
| 6,697,164 B1 | 2/2004 | Babayoff et al. |
| 6,743,014 B2 | 6/2004 | Kerschbaumer et al. |
| 6,750,873 B1 | 6/2004 | Rushmeier et al. |
| 6,751,344 B1 | 6/2004 | Grumbine |
| 6,761,561 B2 | 7/2004 | Mandelkern et al. |
| 6,865,289 B1 | 3/2005 | Berestov |
| 6,904,159 B2 | 6/2005 | Porikli |
| 6,954,550 B2 | 10/2005 | Fujieda |
| 6,967,644 B1 | 11/2005 | Kobayashi |
| 6,975,898 B2 | 12/2005 | Seibel |
| 6,977,732 B2 | 12/2005 | Chen et al. |
| 6,990,228 B1 | 1/2006 | Wiles et al. |
| 7,010,223 B2 | 3/2006 | Thoms |
| 7,027,642 B2 | 4/2006 | Rubbert et al. |
| 7,058,213 B2 | 6/2006 | Rubbert et al. |
| 7,068,825 B2 | 6/2006 | Rubbert et al. |
| 7,077,647 B2 | 7/2006 | Choi et al. |
| 7,079,679 B2 | 7/2006 | Kirk et al. |
| 7,086,863 B2 | 8/2006 | Van |
| 7,099,732 B2 | 8/2006 | Geng |
| 7,123,760 B2 | 10/2006 | Mullick et al. |
| 7,134,874 B2 | 11/2006 | Chishti et al. |
| 7,141,020 B2 | 11/2006 | Poland et al. |
| 7,156,655 B2 | 1/2007 | Sachdeva et al. |
| 7,160,110 B2 | 1/2007 | Imgrund et al. |
| 7,166,537 B2 | 1/2007 | Jacobsen et al. |
| 7,184,150 B2 | 2/2007 | Quadling et al. |
| 7,197,179 B2 | 3/2007 | Rubbert et al. |
| 7,213,214 B2 | 5/2007 | Baar et al. |
| 7,215,430 B2 | 5/2007 | Kacyra et al. |
| 7,221,332 B2 | 5/2007 | Miller et al. |
| 7,230,771 B2 | 6/2007 | Kuiper et al. |
| 7,296,996 B2 | 11/2007 | Sachdeva et al. |
| 7,319,529 B2 | 1/2008 | Babayoff |
| 7,339,170 B2 | 3/2008 | Deliwala |
| 7,349,104 B2 | 3/2008 | Geng |
| 7,355,721 B2 | 4/2008 | Quadling et al. |
| 7,385,708 B2 | 6/2008 | Ackerman et al. |
| 7,458,812 B2 | 12/2008 | Sporbert et al. |
| 7,460,248 B2 | 12/2008 | Kurtz et al. |
| 7,471,821 B2 | 12/2008 | Imgrund et al. |
| 7,474,414 B2 | 1/2009 | Bae et al. |
| 7,483,062 B2 | 1/2009 | Allman et al. |
| 7,494,338 B2 | 2/2009 | Durbin et al. |
| 7,522,322 B2 | 4/2009 | Blanding et al. |
| 7,550,707 B2 | 6/2009 | Hashimoto et al. |

(56) References Cited

U.S. PATENT DOCUMENTS

| | | |
|---|---|---|
| 7,551,353 B2 | 6/2009 | Kim et al. |
| 7,605,817 B2 | 10/2009 | Zhang et al. |
| 7,609,875 B2 | 10/2009 | Liu et al. |
| 7,636,455 B2 | 12/2009 | Keaton et al. |
| 7,698,068 B2 | 4/2010 | Babayoff |
| 7,708,557 B2 | 5/2010 | Rubbert |
| 7,724,378 B2 | 5/2010 | Babayoff |
| 7,762,814 B2 | 7/2010 | Van |
| 7,813,591 B2 | 10/2010 | Paley et al. |
| 7,831,292 B2 | 11/2010 | Quaid et al. |
| 7,840,042 B2 | 11/2010 | Kriveshko et al. |
| 7,929,151 B2 | 4/2011 | Liang et al. |
| 7,929,751 B2 | 4/2011 | Zhang et al. |
| 7,940,260 B2 | 5/2011 | Kriveshko |
| 7,946,845 B2 | 5/2011 | Lehmann |
| 8,003,889 B2 | 8/2011 | Turcovsky |
| 8,026,916 B2 | 9/2011 | Wen |
| 8,035,637 B2 | 10/2011 | Kriveshko |
| 8,078,006 B1 | 12/2011 | Sandrew et al. |
| 8,090,194 B2 | 1/2012 | Gordon et al. |
| 8,092,215 B2 | 1/2012 | Pettinati et al. |
| 8,103,134 B2 | 1/2012 | Sorek et al. |
| 8,121,351 B2 | 2/2012 | Katz et al. |
| 8,121,718 B2 | 2/2012 | Rubbert et al. |
| 8,144,954 B2 | 3/2012 | Quadling et al. |
| 8,177,551 B2 | 5/2012 | Sachdeva et al. |
| 8,179,551 B2 | 5/2012 | Yamamichi |
| 8,180,100 B2 | 5/2012 | Fujimaki et al. |
| 8,208,704 B2 | 6/2012 | Wong et al. |
| 8,260,539 B2 | 9/2012 | Zeng |
| 8,280,152 B2 | 10/2012 | Thiel et al. |
| 8,331,653 B2 | 12/2012 | Seki et al. |
| 8,335,353 B2 | 12/2012 | Yamamoto et al. |
| 8,345,961 B2 | 1/2013 | Li et al. |
| 8,363,228 B2 | 1/2013 | Babayoff |
| 8,384,665 B1 | 2/2013 | Powers et al. |
| 8,386,061 B2 | 2/2013 | Violante et al. |
| 8,390,821 B2 | 3/2013 | Shpunt et al. |
| 8,400,635 B2 | 3/2013 | Inglese et al. |
| 8,442,283 B2 | 5/2013 | Choi |
| 8,451,456 B2 | 5/2013 | Babayoff |
| 8,456,636 B2 | 6/2013 | Hennig |
| 8,469,705 B2 | 6/2013 | Sachdeva et al. |
| 8,477,320 B2 | 7/2013 | Stock et al. |
| 8,526,700 B2 | 9/2013 | Isaacs |
| 8,532,355 B2 | 9/2013 | Quadling et al. |
| 8,547,374 B1 | 10/2013 | Sadjadi et al. |
| 8,564,657 B2 | 10/2013 | Michalke et al. |
| 8,570,530 B2 | 10/2013 | Liang |
| 8,571,281 B2 | 10/2013 | Wong et al. |
| 8,571,397 B2 | 10/2013 | Liu et al. |
| 8,625,854 B2 | 1/2014 | Valkenburg et al. |
| 8,675,207 B2 | 3/2014 | Babayoff |
| 8,743,114 B2 | 6/2014 | Kim et al. |
| 8,828,287 B2 | 9/2014 | Van Der Zel |
| 8,848,991 B2 | 9/2014 | Tjioe et al. |
| 8,867,820 B2 | 10/2014 | Peeper et al. |
| 8,878,905 B2 | 11/2014 | Fisker et al. |
| 8,885,175 B2 | 11/2014 | Babayoff |
| 8,897,526 B2 | 11/2014 | Macleod et al. |
| 8,903,476 B2 | 12/2014 | Brennan et al. |
| 8,903,746 B2 | 12/2014 | Kudritskiy |
| 8,914,245 B2 | 12/2014 | Hopkins |
| 8,998,608 B2 | 4/2015 | Imgrund et al. |
| 9,084,568 B2 | 7/2015 | Katsumata et al. |
| 9,101,433 B2 | 8/2015 | Babayoff |
| 9,107,723 B2 | 8/2015 | Hall et al. |
| 9,173,727 B2 | 11/2015 | Yamamoto et al. |
| 9,185,388 B2 | 11/2015 | Mcnamer et al. |
| 9,208,531 B2 | 12/2015 | Boerjes et al. |
| 9,208,612 B2 | 12/2015 | Frahm et al. |
| 9,262,864 B2 | 2/2016 | Rohaly et al. |
| 9,299,192 B2 | 3/2016 | Kopelman |
| 9,322,646 B2 | 4/2016 | Pochiraju et al. |
| 9,329,675 B2 | 5/2016 | Öjelund et al. |
| 9,402,601 B1 | 8/2016 | Berger et al. |
| 9,404,740 B2 | 8/2016 | Babayoff |
| 9,456,963 B2 | 10/2016 | Lee |
| 9,554,692 B2 | 1/2017 | Levy |
| 9,554,857 B2 | 1/2017 | Toledo-crow et al. |
| 9,566,138 B2 | 2/2017 | Fisker |
| 9,629,551 B2 | 4/2017 | Fisker et al. |
| 9,662,188 B2 | 5/2017 | Laubersheimer et al. |
| 9,675,432 B2 | 6/2017 | Lee et al. |
| 9,707,061 B2 | 7/2017 | Morales et al. |
| 9,827,076 B2 | 11/2017 | Korten et al. |
| 9,844,430 B2 | 12/2017 | Morales et al. |
| 9,845,745 B2 | 12/2017 | Dudar |
| 9,861,457 B2 | 1/2018 | Fisker et al. |
| 9,962,246 B2 | 5/2018 | Miller |
| 10,010,387 B2 | 7/2018 | Esbech et al. |
| 10,064,553 B2 | 9/2018 | Fisker et al. |
| 10,097,815 B2 | 10/2018 | Fisker et al. |
| 10,111,714 B2 | 10/2018 | Kopelman et al. |
| 10,326,982 B2 | 6/2019 | Fisker et al. |
| 10,349,041 B2 | 7/2019 | Fisker et al. |
| 10,349,042 B1 | 7/2019 | Fisker et al. |
| 10,595,010 B2 | 3/2020 | Fisker et al. |
| 10,695,151 B2 | 6/2020 | Esbech et al. |
| RE48,221 E | 9/2020 | Öjelund et al. |
| 10,835,361 B2 | 11/2020 | Fisker et al. |
| 11,051,002 B2 | 6/2021 | Fisker et al. |
| 11,076,146 B1 | 7/2021 | Fisker et al. |
| 11,368,667 B2 | 6/2022 | Fisker et al. |
| 2001/0030748 A1 | 10/2001 | Jung et al. |
| 2001/0038705 A1 | 11/2001 | Rubbert et al. |
| 2003/0035107 A1 | 2/2003 | Overbeck et al. |
| 2003/0043089 A1 | 3/2003 | Hanson et al. |
| 2003/0096210 A1 | 5/2003 | Rubbert et al. |
| 2003/0156283 A1 | 8/2003 | Jung et al. |
| 2003/0158482 A1 | 8/2003 | Poland et al. |
| 2003/0164952 A1 | 9/2003 | Deichmann et al. |
| 2003/0189650 A1* | 10/2003 | Gindele ............... H04N 23/88 348/223.1 |
| 2004/0080754 A1 | 4/2004 | Tobiason et al. |
| 2004/0111029 A1* | 6/2004 | Bates ............... H01R 13/5224 600/437 |
| 2004/0125103 A1 | 7/2004 | Kaufman et al. |
| 2004/0151369 A1 | 8/2004 | Schwotzer |
| 2004/0155975 A1 | 8/2004 | Hart et al. |
| 2004/0185422 A1 | 9/2004 | Orth et al. |
| 2004/0204787 A1 | 10/2004 | Kopelman et al. |
| 2004/0254476 A1 | 12/2004 | Quadling et al. |
| 2005/0020910 A1 | 1/2005 | Quadling et al. |
| 2005/0057745 A1 | 3/2005 | Bontje |
| 2005/0074718 A1 | 4/2005 | Graham et al. |
| 2005/0088529 A1 | 4/2005 | Geng |
| 2005/0090749 A1 | 4/2005 | Rubbert |
| 2005/0099693 A1 | 5/2005 | Schofield et al. |
| 2005/0142517 A1 | 6/2005 | Frysh et al. |
| 2005/0212753 A1 | 9/2005 | Marvit et al. |
| 2005/0212756 A1 | 9/2005 | Marvit et al. |
| 2005/0232509 A1 | 10/2005 | Blake et al. |
| 2005/0237581 A1 | 10/2005 | Knighton et al. |
| 2005/0243330 A1 | 11/2005 | Magarill et al. |
| 2005/0283065 A1* | 12/2005 | Babayoff ............... H04N 13/15 600/407 |
| 2006/0001739 A1 | 1/2006 | Babayoff |
| 2006/0020204 A1 | 1/2006 | Serra et al. |
| 2006/0025684 A1 | 2/2006 | Quistgaard et al. |
| 2006/0072123 A1 | 4/2006 | Wilson et al. |
| 2006/0072189 A1 | 4/2006 | Dimarzio et al. |
| 2006/0092133 A1 | 5/2006 | Touma et al. |
| 2006/0127852 A1 | 6/2006 | Wen |
| 2006/0146009 A1 | 7/2006 | Syrbe et al. |
| 2006/0158665 A1 | 7/2006 | Babayoff et al. |
| 2006/0212260 A1 | 9/2006 | Kopelman et al. |
| 2006/0251408 A1 | 11/2006 | Konno et al. |
| 2007/0016025 A1 | 1/2007 | Arenson et al. |
| 2007/0026363 A1 | 2/2007 | Lehmann et al. |
| 2007/0031774 A1 | 2/2007 | Cinader et al. |
| 2007/0041729 A1 | 2/2007 | Heinz et al. |
| 2007/0064242 A1 | 3/2007 | Childers |
| 2007/0078340 A1 | 4/2007 | Wilcox et al. |

(56) References Cited

U.S. PATENT DOCUMENTS

| | | |
|---|---|---|
| 2007/0081718 A1 | 4/2007 | Rubbert et al. |
| 2007/0103460 A1 | 5/2007 | Zhang et al. |
| 2007/0109559 A1 | 5/2007 | Babayoff et al. |
| 2007/0134615 A1 | 6/2007 | Lovely |
| 2007/0140539 A1 | 6/2007 | Katsumata et al. |
| 2007/0146726 A1 | 6/2007 | Quadling et al. |
| 2007/0171220 A1 | 7/2007 | Kriveshko |
| 2007/0172101 A1 | 7/2007 | Kriveshko et al. |
| 2007/0172112 A1 | 7/2007 | Paley et al. |
| 2007/0182812 A1 | 8/2007 | Ritchey |
| 2007/0194214 A1 | 8/2007 | Pfeiffer |
| 2007/0212667 A1 | 9/2007 | Jung et al. |
| 2007/0252074 A1 | 11/2007 | Ng et al. |
| 2008/0018598 A1 | 1/2008 | Marsden |
| 2008/0024768 A1 | 1/2008 | Babayoff |
| 2008/0058783 A1 | 3/2008 | Altshuler et al. |
| 2008/0063998 A1 | 3/2008 | Liang et al. |
| 2008/0070684 A1 | 3/2008 | Haigh-hutchinson |
| 2008/0071143 A1 | 3/2008 | Gattani et al. |
| 2008/0118886 A1 | 5/2008 | Liang et al. |
| 2008/0131028 A1 | 6/2008 | Pillman et al. |
| 2008/0132886 A1 | 6/2008 | Cohen et al. |
| 2008/0194928 A1 | 8/2008 | Bandic et al. |
| 2008/0194950 A1 | 8/2008 | Mejia et al. |
| 2008/0316898 A1 | 12/2008 | Itoh et al. |
| 2009/0021745 A1 | 1/2009 | Tamura |
| 2009/0040175 A1 | 2/2009 | Xu et al. |
| 2009/0061381 A1 | 3/2009 | Durbin et al. |
| 2009/0076321 A1 | 3/2009 | Suyama et al. |
| 2009/0087050 A1 | 4/2009 | Gandyra |
| 2009/0092955 A1 | 4/2009 | Hwang |
| 2009/0097108 A1 | 4/2009 | Fox et al. |
| 2009/0103103 A1 | 4/2009 | Berner |
| 2009/0133260 A1 | 5/2009 | Durbin et al. |
| 2009/0160858 A1 | 6/2009 | Chen et al. |
| 2009/0167948 A1 | 7/2009 | Berman et al. |
| 2009/0177050 A1 | 7/2009 | Griffiths et al. |
| 2009/0217207 A1 | 8/2009 | Kagermeier et al. |
| 2009/0231649 A1 | 9/2009 | Sirat |
| 2009/0233253 A1 | 9/2009 | Mrazek |
| 2009/0279103 A1 | 11/2009 | Thiel et al. |
| 2009/0291417 A1 | 11/2009 | Rubbert et al. |
| 2009/0298017 A1 | 12/2009 | Boerjes et al. |
| 2009/0322676 A1 | 12/2009 | Kerr et al. |
| 2010/0009308 A1 | 1/2010 | Wen et al. |
| 2010/0014689 A1* | 1/2010 | Kassayan ............ H04R 25/407 381/151 |
| 2010/0079581 A1 | 4/2010 | Russell et al. |
| 2010/0085636 A1 | 4/2010 | Berner |
| 2010/0108873 A1 | 5/2010 | Schwertner |
| 2010/0156901 A1 | 6/2010 | Park et al. |
| 2010/0157086 A1 | 6/2010 | Segale et al. |
| 2010/0201986 A1 | 8/2010 | Inglese et al. |
| 2010/0231509 A1 | 9/2010 | Boillot et al. |
| 2010/0239136 A1 | 9/2010 | Gandyra et al. |
| 2010/0253773 A1 | 10/2010 | Oota et al. |
| 2010/0268069 A1* | 10/2010 | Liang .................. A61B 5/1079 600/425 |
| 2010/0284589 A1* | 11/2010 | Thiel ...................... A61C 9/006 348/66 |
| 2010/0311005 A1* | 12/2010 | Liang ................. G01B 11/2527 433/29 |
| 2011/0125304 A1 | 5/2011 | Schneider et al. |
| 2011/0188726 A1 | 8/2011 | Nathaniel et al. |
| 2011/0200249 A1 | 8/2011 | Minear et al. |
| 2011/0310449 A1 | 12/2011 | Kim et al. |
| 2011/0316978 A1 | 12/2011 | Dillon et al. |
| 2012/0015316 A1 | 1/2012 | Sachdeva et al. |
| 2012/0062557 A1 | 3/2012 | Dillon et al. |
| 2012/0141949 A1 | 6/2012 | Bodony et al. |
| 2012/0179035 A1 | 7/2012 | Boudier |
| 2012/0195471 A1 | 8/2012 | Newcombe et al. |
| 2013/0034823 A1 | 2/2013 | Liang et al. |
| 2013/0110469 A1 | 5/2013 | Kopelman |
| 2013/0158694 A1 | 6/2013 | Rubbert et al. |
| 2013/0218530 A1 | 8/2013 | Deichmann et al. |
| 2013/0218531 A1 | 8/2013 | Deichmann et al. |
| 2013/0244197 A1 | 9/2013 | Tjioe et al. |
| 2013/0260340 A1 | 10/2013 | Stegall et al. |
| 2013/0335417 A1 | 12/2013 | McQueston et al. |
| 2014/0022352 A1 | 1/2014 | Fisker et al. |
| 2014/0022356 A1 | 1/2014 | Fisker et al. |
| 2014/0071258 A1 | 3/2014 | Gandyra |
| 2014/0146142 A1 | 5/2014 | Duret et al. |
| 2014/0255878 A1 | 9/2014 | Jesenko et al. |
| 2014/0377718 A1 | 12/2014 | Korten et al. |
| 2015/0054922 A1 | 2/2015 | Fisker et al. |
| 2016/0022389 A1 | 1/2016 | Esbech et al. |
| 2016/0067018 A1 | 3/2016 | Korten et al. |
| 2018/0153664 A1 | 6/2018 | Esbech et al. |
| 2018/0255293 A1 | 9/2018 | Fisker et al. |
| 2019/0124323 A1 | 4/2019 | Fisker et al. |
| 2019/0200006 A1 | 6/2019 | Fisker et al. |
| 2019/0289283 A1 | 9/2019 | Fisker et al. |
| 2020/0169722 A1 | 5/2020 | Fisker et al. |
| 2020/0352688 A1 | 11/2020 | Esbech et al. |
| 2021/0211638 A1 | 7/2021 | Fisker et al. |
| 2021/0306617 A1 | 9/2021 | Fisker et al. |
| 2022/0086418 A1 | 3/2022 | Fisker et al. |
| 2022/0265402 A1 | 8/2022 | Esbech et al. |
| 2022/0265403 A1 | 8/2022 | Esbech et al. |
| 2022/0272316 A1 | 8/2022 | Fisker et al. |
| 2022/0272317 A1 | 8/2022 | Fisker et al. |
| 2023/0058298 A1 | 2/2023 | Fisker et al. |
| 2023/0403387 A1 | 12/2023 | Fisker et al. |

FOREIGN PATENT DOCUMENTS

| | | |
|---|---|---|
| CN | 1934481 A | 3/2007 |
| CN | 101426085 A | 5/2009 |
| CN | 101513350 A | 8/2009 |
| DE | 19524855 A1 | 1/1997 |
| DE | 19642247 C1 | 1/1998 |
| DE | 10321863 A1 | 12/2004 |
| DE | 10321883 A1 | 12/2004 |
| DE | 102007005726 A1 | 8/2008 |
| DE | 102009023952 A1 | 12/2010 |
| EP | 0837659 A1 | 4/1998 |
| EP | 2200332 A1 | 6/2010 |
| EP | 2325771 A2 | 5/2011 |
| EP | 2620733 A1 | 7/2013 |
| EP | 2664272 A1 | 11/2013 |
| EP | 2799032 A1 | 11/2014 |
| JP | 62100716 A | 5/1987 |
| JP | H06505096 A | 6/1994 |
| JP | H06201337 A | 7/1994 |
| JP | 3321866 B2 | 9/2002 |
| JP | 2004029685 A | 1/2004 |
| JP | 2005098833 A | 4/2005 |
| JP | 2007072103 A | 3/2007 |
| JP | 2008194108 A | 8/2008 |
| JP | 2009098146 A | 5/2009 |
| JP | 2009238245 A | 10/2009 |
| WO | 8807695 A1 | 10/1988 |
| WO | 9214118 A1 | 8/1992 |
| WO | 9215034 A1 | 9/1992 |
| WO | 9702788 A1 | 1/1997 |
| WO | 9714932 A1 | 4/1997 |
| WO | 9845745 A1 | 10/1998 |
| WO | 9947964 A1 | 9/1999 |
| WO | 0008415 A1 | 2/2000 |
| WO | 0111193 A1 | 2/2001 |
| WO | 0184479 A1 | 11/2001 |
| WO | 02076327 A1 | 10/2002 |
| WO | 03060587 A1 | 7/2003 |
| WO | 03073457 A2 | 9/2003 |
| WO | 2004066615 A1 | 8/2004 |
| WO | 2005067389 A2 | 7/2005 |
| WO | 2006065955 A2 | 6/2006 |
| WO | 2007084727 A1 | 7/2007 |
| WO | 2008125605 A2 | 10/2008 |
| WO | 2009026645 A1 | 3/2009 |
| WO | 2009034157 A1 | 3/2009 |
| WO | 2009063088 A2 | 5/2009 |

(56) References Cited

FOREIGN PATENT DOCUMENTS

| | | |
|---|---|---|
| WO | 2009089126 A1 | 7/2009 |
| WO | 2010064156 A1 | 6/2010 |
| WO | 2010106379 A1 | 9/2010 |
| WO | 2010145669 A1 | 12/2010 |
| WO | 2011011193 A1 | 1/2011 |
| WO | 2011047731 A1 | 4/2011 |
| WO | 2011120526 A1 | 10/2011 |
| WO | 2012000511 A1 | 1/2012 |
| WO | 2012007003 A1 | 1/2012 |
| WO | 2012076013 A1 | 6/2012 |
| WO | 2012083960 A1 | 6/2012 |
| WO | 2012115862 A2 | 8/2012 |
| WO | 2013010910 A1 | 1/2013 |
| WO | 2013122662 A1 | 8/2013 |
| WO | 2014125037 A1 | 8/2014 |

OTHER PUBLICATIONS

"221 Patent in View of Knighton U.S. Pat. No. RE48,221", D-2 Preliminary Invalidity Contentions, 15 pages.
"221 Patent in View of Quadling U.S. Pat. No. RE48,221", D-3 Preliminary Invalidity Contentions, 17 pages.
"221 Patent in View of Serra U.S. Pat. No. RE48,221", D-4 Preliminary Invalidity Contentions, 12 pages.
"3Shape A/S Markman Hearing Presentation", Case No. 1:18-886-LPS, Apr. 21, 2020, 104 pages.
"*3Shape A/S* v. *Align Technology, Inc.*, IPR2021-01383, Petition for Inter Partes Review", U.S. Pat. No. 10,728,519, Aug. 20, 2021, 112 pages.
"Amended Complaint for Patent Infringement", *3SHAPE A/S* v. *Align Technology, Inc.*, Case No. 18-886-LPS, Aug. 30, 2019, 166 pages.
"Answer, Affirmative Defenses, and Counterclaims of Align Technology, Inc.", *3SHAPE A/S* v. *Align Technology, Inc.*, C.A. No. 18-886-LPS, Oct. 21, 2019, 46 pages.
"Bajaj, C. L", Align EX1004, *Align* v. *3Shape*, IPR2022-00144, Exhibit. 1004, 42 pages.
"Complaint", *3Shape A/S* v. *Carestream Dental, LLC*, Civil Action No. 6:21-cv-1110, 59 pages.
"Corrected Petition for Inter Partes Review", U.S. Pat. No. 11,368,667; U.S. Patent & Trademark Office IPR2023-00411, *Dental Imaging Technologies Corporation* (Petitioner) v. *3Shape A/S* (Patent Owner, 88 pages.
"Curriculum Vitae of Dr. Chandrajit L. Bajaj", (IPR2018-00197, Ex. 1004) (IPR2018-00198, Ex. 1004), 49 pages.
"Curriculum Vitae of Dr. James L. Mullins".
"Curriculum Vitae of Dr. Ioannis A. Kakadiaris".
"Curriculum Vitae of Dr. Mohit Gupta".
"Curriculum Vitae of Ravin Balakrishanan", (IPR2018-00197, EX2012), 30 pages.
"Curriculum Vitae of Ravin Balakrishanan Ph.D", (IPR2018-00197, EX.2012), 30 pages.
"Decision Denying Institution entered May 30, 2018 in IPR20198-00198", , May 30, 2018.
"Decision Denying Petitioner's Request for Rehearing in IPR20198-00198", U.S. Pat. No. 9,329,675, Dec. 4, 2018, 8 pages.
"Declaration of Dr. Chandrajit Bajaj ("Bajaj Decl.") in support of Petition for Inter Partes Review", U.S. Pat. No. RE48,221, 377 pages.
"Declaration of Dr. Chandrajit L. Bajaj", (IPR2018-00197, Ex. 1003), Jul. 25, 2018, 142 pages.
"Declaration of Dr. James L. Mullins".
"Declaration of Dr. Mohit Gupta for U.S. Pat. No. 11,076,146, executed on Oct. 26, 2022".
"Declaration of James L. Mullins", *Dental Imaging Technologies Corporation* (Petitioner) v. *3Shape A/S* (Patent Owner), 78 pages.
"Declaration of Ioannis A. Kakadiaris".
"Declaration of Mohit Gupta, Ph.D.", U.S. Pat. No. 11,368,667, *Dental Imaging Technologies Corporation* (Petitioner) v. *3Shape A/S* (Patent Owner)., 83 pages.
"Declaration of Ravin Balakrishanan", (IPR2018-00197, EX.2011), 55 pages.
"Defendant Align Technology, Inc.'s Initial Invalidity Contentions", *3Shape A/S* v. *Align Technology, Inc.*, C.A. No. 1:18-cv-00886-LPS, Nov. 21, 2017, 393 pages.
"Defendant Align Technology, Inc.'s Stipulation of Invalidity Contentions", *3Shape A/S* v. *Align Technology, Inc.*, C.A. No. 18-886-LPS, Exhibit 1053, Nov. 13, 2020, 3 pages.
"Defendants' First Supplemental Invalidity Contentions", (NDGA—Civil Action No. 1:22-cv-01829-WMR), , Nov. 7, 2022, 101 pages.
"Defendants' First Supplemental Invalidity Contentions (NDGA—Civil Action No. 1:22-cv-01829-WMR)", In the United States District Court for the Northern District of Georgia, *3Shape A/S*, Plaintiff, v. *Carestream Dental, LLC*, Dental Imaging Technologies Corp., Nov. 7, 2022, 101 pages.
"Defendant's Identification of Invalidity References", *3SHAPE A/S et al.* v. *Align Technology, Inc.*, C. A. No. 1:18-cv-00886-LPS, 72 pages.
"Defendants Initial Invalidity Contentions", (NDGA—Civil Action No. 1:22-cv-01829-WMR), , Sep. 12, 2022, 92 pages.
"Defendants Initial Invalidity Contentions (NDGA—Civil Action No. 1:22-cv-01829-WMR)", , Sep. 12, 2022.
"Dentistry Application of CAD/CAM System", Dentistry Artisan, vol. 21, Oct. 1, 1993.
"Deposition Transcript of Chandrajit Bajaj, Ph.D with Errata Sheet", (IPR2018-00197 Ex-2008), Jul. 25, 2018, 142 pages.
"Deposition Transcript of Dr. Ravin Balakrishnan", , Nov. 5, 2018.
"Exhibit 6—Latest Optical 3D Measurementai", , Nov. 20, 2006.
"File History", U.S. Pat. No. RE48,221, 1004 pages.
"File History (IPR2018-00197, Ex. 1002) (IPR2018-00198, Ex. 1002)", U.S. Pat. No. 9,329,675, 625 pages.
"Final Written Decision—Termination Decision Document from IPR2018-00197", U. S. Pat. No. 9,329,675 B2, May 29, 2019, 64 pages.
"IEEE Xplore Search Results", Accessed Mar. 2, 2018; this document was made of record by the Examiner on Mar. 13, 2018, in the parent application (U.S. Appl. No. 15/117,078), 4 pages.
"Institution Decision entered in IPR20198-00197", U.S. Pat. No. 9,329,675, May 30, 2018, 32 pages.
"Introducing Wii MotionPlus, Nintendo's upcoming accessory for the revolutionary Wii Remote", Nintendo, The Wayback Machine, Jul. 14, 2008, 2 pages.
"Memorandum Order", *3Shape A/S* v. *Align Technology, Inc.*, C.A. No. 18-886-LPS, Exhibit 2022, Dec. 28, 2020, 3 pages.
"Optical System for a Confocal Microscope", Certified English Translation of Application No. 01580/08, Oct. 6, 2008, 40 pages.
"Order", *Lipocine Inc.* v. *Clarus Therapeutics, Inc.*, C.A. No. 19-622 (WCB), Exhibit 1052, Nov. 12, 2020, 2 pages.
"Patent Owner's Preliminary Response to the Petition for Inter Partes Review in IPR2018-00198", U.S. Pat. No. 9,329,675, Mar. 3, 2018, 66 pages.
"Patent Owner's Preliminary Response to the Petition for Inter Parties Review in IPR2018-00197", U.S. Pat. No. 9,329,675, Mar. 3, 2018, 66 pages.
"Patent Owner's Response to the Petition for Inter Partes Review in IPR2018-00197", U.S. Pat. No. 9,329,675, Aug. 20, 2018, 57 pages.
"Patent Owner's Submission of Demonstratives for Oral Argument in IPR2018-00197", U.S. Pat. No. 9,329,675, Jan. 31, 2019, , 42 pages.
"Petition for Inter Partes Review", U.S. Pat. No. 9,329,675, Nov. 22, 2017, 67 pages.
"Petition for Inter Partes Review", U.S. Pat. No. 11,076,146, 89 pages.
"Petition for Inter Partes Review of U.S. Pat. No. 11,368,667", , , Dec. 23, 2022.
"Petitioner Align Technology, Inc.'s Demonstratives in IPR2018-00197", U.S. Pat. No. 9,329,675, Jan. 31, 2019, , 30 pages.
"Petitioner Align Technology, Inc.'s Reply to Patent Owner Response in IPR2018-00197", U.S. Pat. No. 9,329,675, Nov. 14, 2018, , 35 pages.

(56) References Cited

OTHER PUBLICATIONS

"Petitioner's Align Technology, Inc's Request For Rehearing in IPR20198-00198", U.S. Pat. No. 9,329,675, Jun. 29, 2018, 14 pages.
"Plaintiff and Counterclaim Defendant Align Technology, Inc.'s Stipulation Regarding IPR2022-00144 and IPR2022-00145,", Case No. 6:20-cv-00979 (W.D. Tex.), Dec. 16, 2021, 4 pages.
"Prosecution History of U.S. Pat. No. 11,076,146".
"Prosecution History of U.S. Pat. No. 11,368,667".
"Record of Oral Hearing in IPR2018-00197", U.S. Pat. No. 9,329,675, Feb. 4, 2019, 67 pages.
"Report and Recommendation", *3SHAPE A/S* v. *Align Technology, Inc.*, Case No. 18-886-LPS, May 6, 2020, 24 pages.
"Taxonomies of Input in Developing a Taxonomy of Input", (IPR2018-00197, Ex. 2010) Available at https:/iwww.billbuxton.com/input04.Taxonomies.pdf., Jan. 4, 2009, 16 pages.
"Transcript of Alexander V. Sergienko, Ph.D.", *Align Technology, Inc.* v. *3Shape A/S et al.*, Exhibit 1056, Jul. 16, 2021, 212 pages.
"Transcript of Video Claim Construction Hearing", *3Shape A/S* v. *Align Technology, Inc.*, Case No. 18-886-LPS, Apr. 21, 2020, 137 pages.
"U.S. Appl. No. 10/744,869", (IPR2018-00197, Ex. 2005), 69 pages.
"VISTACAM, Installation and Operating Instructions", Durr Vistacam, Vistacam CI 2016, Nov. 1, 2004, 31 pages.
"VIVID 910: Non-Contact 3-D Digitizer", www.minolta.com, 3 pages.
01580/08, "Swiss Priority Document", English Translation, Oct. 6, 2008.
01580/08, "Optical System for a Confocal Microscope", , 20 pages.
U.S. Pat. No. 10,349,042, "Petition for Inter Partes Review", . IPR2020-01089.
U.S. Pat. No. 10,349,042, , "Patent Owner's Preliminary Response to the Petition for Inter Partes Review", IPR2020-01088 Exhibit 1062, Oct. 23, 2020).
U.S. Pat. No. 10,695,151, "Petition for Inter Partes Review of U.S. Pat. No.", , 87 pages.
U.S. Appl. No. 15/117,078, "IEEE Xplore Search Results", , 4 pages.
201080027248.7, "Office Action issued", , 30 pages.
2014-234653, "Information Statement", , 25 pages.
2014-234653, "Notification of Information Statemen", , 2 pages.
201510098304.0, "Office Action(First Office Action)", , 18 pages.
Agrawal, et al., "Color and Shade Management in Esthetic Dentistry", Universal Research Journal of Dentistry, vol. 3, No. 3, Dec. 2013, pp. 120-127.
Ahn, et al., "Development of Three-Dimensional Dental Scanning Apparatus Using Structured Illumination", Sensors, vol. 17, Issue 7, 1634 (IPR2018-00197, Ex. 2004) (IPR2018-00198, Ex. 2002), 2017, 9 pages.
Align Technology, Inc., , "Petition for Inter Partes Review of U.S. Pat. No. 10,349,042, Case No. IPR2020-01087".
Atieh, Mohammad A, "Accuracy Evlaution of Intral-Oral Optical Impressions: A Novel Approach", Thesis, University of North Carolina at Chapel Hill, 2016, 87 pages.
Atieh, "Accuracy Evaluation of Intral-Oral Optical Impressions: A Novel Approach", 87 pages.
Baltzer, et al., "The Determination of the Tooth Colors", Quintessenz Zahntechnik, vol. 30., No. 7, 2004, pp. 726-740.
Bernardini, et al., "High-Quality Texture Reconstruction from Multiple Scans", IEEE Transactions on Visualization and Computer Graphics, vol. 7, No. 4, Oct.-Dec. 2001, pp. 318-332.
Birnbaum, et al., "Dental Impressions Using 3D Digital Scanners: Virtual Becomes Reality", Compendium of Continuing Education in Dentistry, vol. 29, No. 8, Oct. 2008, 18 pages.
Bornik, et al., "A Hybrid User Interface for Manipulation of Volumetric Medical Data", 3D User Interfaces, 2006, pp. 29-36 (8 pages).
Borse, et al., "Tooth Shade Analysis and Selection in Prosthodontics: A Systematic Review and Meta-Analysis", The Journal of Indian Prosthodontic Society, vol. 20, No. 2, 2020, pp. 131-140.
Bowman, et al., 3D User Interfaces Theory and Practice § 4.1.1 "Input Device Characteristics" pp. 88-89; § 4.2.2 "2D Mice and Trackballs" pp. 91-92; § 4.8.2 "Input Device Taxonomies" pp. 128-132, Addison Wesley (IPR2018-00197, Ex. 2013), 2005, 20 pages.
Bowman, et al., "3D User Interfaces: Theory and Practice", Addison-Wesley, 2004, pp. 96-101 (9 pages).
Broadbent, B Holly, "A New X-Ray Technique and Its Application to Orthodontia", The Angle Orthodontist, vol. 1, No. 2, Apr. 1931, pp. 45-66.
Broadhurst, et al., "A Probabilistic Framework for Space Carving", Proceedings Eighth IEEE International Conference on Computer Vision, vol. 1, 2001, 6 pages.
Callier, et al., "Reconstructing Textured Meshes From Multiple Range+rgb Maps", 7th International Fall Workshop on Vision, Modeling, and Visualization, Nov. 2002, , 8 pages.
Callieri, et al., "Reconstructing Textured Meshes From Multiple Range+rgb Maps", Vision, Modeling, and Visualization, Nov. 2002, 8 pages.
Chen, et al., "A Volumetric Stereo Matching Method: Application to Image-Based Modeling", IEEE Computer Society Conference on Computer Vision and Pattern Recognition (Cat. No PR00149). vol. 1, 1999, 6 pages.
Chen, et al., "Miniaturized 3D Surface Profilometer Using Digital Fringe Projection", Measurement Science and Technology, vol. 16, No. 5, Mar. 22, 2005, pp. 1061-1068.
Cherry, Richard J, "New Techniques of Optical Microscopy and Micro spectroscopy", Springer, 1991, 3 pages.
Cherry, Richard J, "New Techniques of Optical Microscopy and Microspectroscopy", The Macmillan Press Ltd., 1991, 3 pages.
Chu, et al., "Dental Color Matching Instrument and Systems. Review of Clinical and Research Aspects", Journal of Dentistry, vol. 38, Suppl. 2, 2010, pp. e2-e16.
Chua, et al., "SonoDEX: 3D Space Management and Visualization of Ultrasound Data", International Congress Series, vol. 1281, (I PR2018-00197, Ex. 2006), May 2005, pp. 143-148.
CN 201080027248.7, "First Office Action", English Translation, Feb. 20, 2014, 22 pages.
CN 201180066956.6, "First Office Action", English Translation, Apr. 3, 2015, 13 pages.
CN 201180066956.6, "Second Office Action", English Translation, Nov. 18, 2015, , 27 pages.
CN 201510098304.0, "First Office Action", English Translation, Dec. 2, 2016, 15 pages.
Complaint, "*3Shape MS* v_ *Carestream Dental, LLC*", Civil Action No. 6:21-cv-1110, WDTX, Oct. 26, 2021, 59 pages.
Corcodel, et al., "Metameric Effect Between Natural Teeth and the Shade Tabs of a Shade Guide", European Journal of Oral Sciences, vol. 118, No. 3, Jun. 2010, pp. 311-316.
Darrell, et al., "Pyramid Based Depth from Focus", Proceedings CVPR '88: The Computer Society Conference on Computer Vision and Pattern Recognition, 1988, pp. 504-509.
Douglas, et al., "Intraoral Determination of the Tolerance of Dentists for Perceptibility and Acceptability of Shade Mismatch", Journal of Prosthetic Dentistry, vol. 97, No. 4, Apr. 2007, pp. 200-208.
Eisert, et al., "Automatic Reconstruction of Stationary 3-D Objects from Multiple Uncalibrated Camera Views", IEEE Transactions On Circuits and Systems for Video Technology, vol. 10, No. 2, Mar. 2000, pp. 261-277.
Eisert, et al., "Multi-Hypothesis, Volumetric Reconstruction Of 3-D Objects From Multiple Calibrated Camera Views", CASSP'99, Phoenix, USA, Mar. 1999, pp. 3509-3512.
Eisert, Peter, "Reconstruction of Volumetric 3D Models", 3D Video Communication: Algorithms, Concepts and Real-Time Systems in Human Centred Communication, pp. 1-20.
Elgammal, "CS 534: Computer Vision Texture,", , 22 pages.
Elgammal, Ahmed, "CS 534: Computer Vision Texture", , 2003, 22 pages.
EP 11847582.1, "~PO Prosecution History received".

(56) References Cited

OTHER PUBLICATIONS

EP 11847582.1 , "EPO Prosecution History", , 180 pages.
EP 2442720, "Interlocutory Decision in Opposition Proceedings", 15 pages.
EP 2442720, "Notice of Opposition", , 23 pages.
EP 2442720, "Notice of Opposition", , 41 pages.
EP 2442720, "Notice of Opposition", , 5 pages.
EP 2442720, "Notice of Opposition", , 6 pages.
Ferreira , et al. , "Tele-3D—Developing a Handheld Scanner Using Structured Light Projection" , Proceedings of the First International Symposium on 3D Data Processing Visualization and Transmission (3DPVTí02) , Jan. 30, 2023 , 4 pages.
Fisher , et al. , "Dictionary of Computer Vision & Image Processing" , Wiley, Second Edition , 2014 , 386 pages.
Fisker , et al. , "Focus Scanning Apparatus" , U.S. Appl. No. 61/231,118, filed Aug. 4, 2009 , 127 pages.
Fisker , et al. , "Focus Scanning Apparatus" , U.S. Appl. No. 61/187,744, filed Jun. 17, 2009 , 90 pages.
Foley , et al. , "Introduction to Computer Graphics" , Addison-Wesley, Chapter 2.2: Basic Interaction Handling, "Chapter 6: Viewing in 3D," and Chapter 8: Input Devices, Interaction Techniques, and Interaction Tasks , 1994 , 66 pages.
Forne, Christopher J , "3-D Scene Reconstruction From Multiple Photometric Images" , PhD Thesis in Electrical and Computer Engineering at the University of Canterbury, Christchurch, New Zealand , Apr. 30, 2007 , 179 pages.
Fraser , et al. , "Zoom-Dependent Camera Calibration in Digital Close-Range Photogrammetry" , Photogrammetric Engineering & Remote Sensing, vol. 72, No. 9, Exhibit 1064 , Sep. 2006 , pp. 1017-1026.
Gao , et al. , "3D Shape Reconstruction of Teeth by Shadow Speckle Correlation Method" , Optics and Lasers in Engineering, vol. 44 , 2006 , pp. 455-465.
Gehrung , et al. , "An Approach to Extract Moving Objects From MLS Data Using a Volumetric Background Representation", ISPRS Annals of the Photogrammetry, Remote Sensing and Spatial Information Sciences, vol. IV-1/W1 , Jun. 2017 , pp. 107-114.
Giammanco , et al. , "Using 3D Laser Scanning Technology to Create Digital Models of Hailstones" , American Meteorological Society , Jul. 2017 , pp. 1341-1347 (8 pages).
Gmitro , et al. , "Confocal Microscopy through a Fiber-Optic Imaging Bundle" , Optics Letters, vol. 18, No. 8 , Apr. 15, 1993 , pp. 565-567 (4 pages).
Gonzalez , et al. , "Digital Image Processing, Pearson Prentice Hall," , Third Edition , 2008 , 977 pages.
Graetzel , et al. , "A Non-Contact Mouse for Surgeon-Computer Interaction" , Technology and Health Care, vol. 12, No. 3 , 2004 , pp. 245-257.
Grant , et al. , "Glossary of Digital Dental Terms: American College of Prosthodontists" , Journal of Prosthodontics, vol. 25, Suppl. 2 , Oct. 2016 , pp. S2-S9.
Guan , et al. , "Multi-view Occlusion Reasoning for Probabilistic Silhouette-Based Dynamic Scene Reconstruction", International Journal of Computer Vision, vol. 90 , 2010 , pp. 283-303.
Guehring , et al. , "Dense 3D surface acquisition by structured light using off-the-shelf components," , vol. 4309 , Dec. 22, 2000) , 13 pages.
Guehring, Jens , "Dense 3D Surface Acquisition By Structured Light using off-the-Shelf Components" , Proceedings SPIE 4309, Videometrics and Optical Methods for 3D Shape Measurement , pp. 220-231 (13 pages).
Hajeer, et al., "Current Products and Practices Applications of 3D Imaging in Orthodontics: Part II", Journal of Orthodontics, vol. 31, 2004, pp. 154-162.
Hale , et al. , "Measuring Free-Living Physical Activity in Adults with and Without Neurologic Dysfunction with a Triaxial Accelerometer" , Archives of Physical Medicine and Rehabilitation, vol. 89, No. 9, Sep. 2008 , pp. 1765-1771.
Havemann , et al. , "Seven Research Challenges of Generalized 3D Documents" , IEEE Computer Graphics and Applications, vol. 27, No. 3 , May-Jun. 2007 , pp. 70-76.
Hearn , et al. , "Computer Graphics" , 2d. Ed., Prentice Hall, Chapter 2: Overview of Graphics Systems, "Chapter 8: Graphical User Interfaces and Interactive Input Methods," and "Chapter 9: Three-Dimensional Concepts" , 1994 , 83 pages.
Horn , et al. , "Calculating the Reflectance Map" , Applied Optic, vol. 18, No. 11 , Jun. 1979 , pp. 1770-1779.
Horn , et al. , "Calculating the Reflectance Map" , Applied Optics, vol. 18, No. 11 , Jun. 1, 1979 , pp. 1770-1779 (11 pages).
IPR2018-00197 , "PTAB Trial Certificate Inter Partes Review Certificate" , U.S. Pat. No. 9,329,675, , Oct. 25, 2019 , 2 pages.
Ipr2019-00118, , "Petition for Inter Partes Review" , U.S. Pat. No. 9,962,244, , Nov. 5, 2018, , 93 pages.
IPR2019-00157 , "Petition for Inter Partes Review of U.S. Pat. No. 8,363,228" , 3Shape A/S et al. v. Align Technology, Inc. Exhibit 1063 , Nov. 8, 2018.
Ireland, et al., "3D Surface Imaging in Dentistry—What we are Looking at", British Dental Journal, vol. 205, No. 7, Oct. 11, 2008, pp. 387-392.
Ishikawa-Nagai, et al., "Reproducibility of Tooth Color Gradation Using A Computer Color-Matching Technique Applied to Ceramic Restorations", J. Prosthetic Dentistr, Feb. 2005, pp. 129-137.
Ishikawa-Nagai , et al. , "Reproducibility of Tooth Color Gradation Using A Computer Color-Matching Technique Applied to Ceramic Restorations", Journal of Prosthetic Dentistry, vol. 93, Issue 2 , Feb. 2005 , pp. 129-137.
Jahne, et al., "Handbook of Computer Vision and Applications", System and Applications, vol. 3, Academic press, 1999, 955 pages.
Jahne, et al., "Handbook of Computer Vision and Applications", Sensors and Imaging, vol. 1, Academic Press, 1999, 657 pages.
Jahne, et al., "Handbook of Computer Vision and Applications", Signal Processing and Pattern Recognition, Academic Press, vol. 2, 1999, 967 pages.
Jerald, Jason, "The VR Book: Human-Centered Design for Virtual Reality", (IPR2018-00197 Ex-2014), 4 pages.
Jethwa, Manish, "Efficient Volumetric Reconstruction from Multiple Calibrated Cameras", PhD Thesis in Electrical Engineering and Computer Science at MIT, 143 pages.
Johnstone, Bob, et al., "Cameras Give Semiconductor Industry a Boost", , Nov. 7, 1985, 1 page.
JP 2014-234653, "Information Statement", English Translation, Jul. 28, 2016, 25 pages.
JP 2014-234653 , "Notification of Information Statement", English Translation, Aug. 2, 2016 2 pages.
JP 2014-234653, "Notification of Third Party Observations", , 31 pages.
JP 2014-234653, "notification of third party observations Received", 31 pages.
Kang, Henry R, "Three-Dimensional Lookup Table with Interpolation", Computational Color Technology, Chapter 9, 2006, pp. 151-159.
Karatas, et al., "Three-dimensional imaging techniques: A literature review", European Journal of Dentistry, vol. 8, Issue 1, 2014; (IPR2018-00197, Ex. 1016) (IPR2018-00198, Ex. 1016), 2014, pp. 132-140.
Karatas, et al., "Three-Dimensional Imaging Techniques: A Literature Review", European Journal of Dentistry, vol. 8, Issue 1, Jan.-Mar. 2014, pp. 132-140.
Kaufmann, Hannes, "Applications of Mixed Reality", Thesis, Vienna University of Technology, 95 pages.
Keating, Michael P, "Geometric, Physical, and Visual Optics", , 1988, 3 pages.
Kuhmstedt, et al., "Intraoral 3D Scanner", Proceedings of SPIE, vol. 6762, Oct. 10, 2007, 10 pages.
Lagouvardos, et al., "Repeatability and Interdevice Reliability of Two Portable Color Selection Devices in Matching and Measuring Tooth Color", The Journal of Prosthetic Dentistry, vol. 101, Issue 1, Jan. 2009, pp. 40-45.
Li, et al., "Empty Space Skipping and Occlusion Clipping for Texture-based Volume Rendering", IEEE Visualization, 2003, 8 pages.

(56) References Cited

OTHER PUBLICATIONS

Litomisky, et al., "Removing Moving Objects from Point Cloud Scenes", Advances in Depth Image Analysis and Applications, Jan. 2013, pp. 1-10.
Liu, et al., "A Complete Statistical Inverse Ray Tracing Approach to Multi-View Stereo", Conferences, CVPR, 2011, pp. 913-920.
Logozzo, et al., "Recent Advances in Dental Optics—Part I: 3D Intraoral Scanners for Restorative Denistry", Optics and Lasers in Engineering, vol. 54, Mar. 2014, pp. 203-221 (1-19).
Lovi, David Israel, "Incremental Free-Space Carving for Real-Time 3D Reconstruction", Master of Science Thesis in Computer Science at University of Alberta, 2011, 74 pages.
MacKinlay, et al., "A Semantic Analysis of the Design Space of Input Devices", Human Computer Interaction, vol. 5, 1990, pp. 145-190.
Montes, et al., "An Overview of BRDF Models", University of Granada, 2012, 26 pages.
Montes, et al., "An Overview of BRDF Models", University of Granada, 2012, pp. 1-26.
Moran, et al., "A Comparison of the Imaging Performance of High Resolution Ultrasound Scanners for Preclinical Imaging", Ultrasound in Medicine & Biology, vol. 37, No. 3, Mar. 2011, pp. 493-501.
Myers, Brad A, "Graphical User Interface Programming", CRC Handbook of Computer Science and Engineering, 2d. Ed., Allen B. Tucker, Jan. 27, 2003, 30 pages.
Nasiri, Steven, "A Critical Review of MEMS Gyroscopes Technology and Commercialization Status", InvenSense, 8 pages.
Neil, et al., "Method of Obtaining Optical Sectioning by Using Structured Light in a Conventional Microscope", Optics Letters, vol. 22, No. 24, Dec. 15, 1997, pp. 1905-1907.
Netravali, et al., "Digital Pictures: Representation, Compression, and Standards (Applications of Communications Theory)", , 701 pages.
Nioguch, et al., "Microscopic Shape from Focus Using a Projected Illumination Pattern", vol. 24, No. 5/6, Sep. 1996, pp. 31-48.
Nitschke, et al., "Real-Time Space Carving Using Graphics Hardware", IEICE Transactions on Information and Systems, Aug. 2007, pp. 1175-1184 (11 pages).
Noguchi, et al., "Microscopic Shape from Focus Using a Projected Illumination Pattern", Mathematical and Computer Modelling, vol. 24, No. 5/6, Sep. 1996, pp. 31-48.
Notni, et al., "The Concept of Virtual Landmarks in 3D-multi-view Fringe Projection", Proceedings of SPIE, vol. 6782, Oct. 11, 2007, 11 pages.
Ogami, Moria, "Exhibit 2-3D Imagery Handbook", , Feb. 20, 2006, 4 pages.
Ogami, Moria, "Exhibit 2-3D Imagery Handbook", First Edition, pp. 1-4.
Ojelund, et al., "Inter Partes Review Certificate", U.S. Pat. No. 9,329,675 K1.
PA 201470066, "DK priority document for Patent Application No." Paris, et al., "A Surface Reconstruction Method using Global Graph Cut Optimization", International Journal of Computer Vision, vol. 66, No. 2, 2010, pp. 141-161.
PCT/DK2010/050., "Notification Concerning Transmittal of International Preliminary Report on Patentability and the Written Opinion".
PCT/DK2010/050148, "International Preliminary Report on Patentability Received", , 10 pages.
PCT/DK2010/050148, "International Search Report and Written Opinion", , 13 pages.
PCT/DK2010/050148, "International Search Report Received", , 5 pages.
PCT/DK2010/050148, "Notification Concerning Transmittal of International Preliminary Report".
PCT/DK2010/050148, "Witten Opinion".
PCT/DK2010/050148, "Written Opinion Received", , 8 pages.
PCT/DK2011/050461, "International Search Report (PCT/ISA/210)", , 6 pages.
PCT/EP2015/052537, "International Preliminary Report on Patentability", , 11 pages.
PCT/EP2015/052537, "International Search Report (PCT/ISA/210)", , 5 pages.
PCT/EP2015/052537, "International Search Report and Written Opinion", , 14 pages.
PCT/EP2015/052537, "Written Opinion (PCT/ISA/237)", , 9 pages.
Pollard, et al., "Change Detection in a 3-D World", , 6 pages.
Pollard, et al., "Change Detection in a 3-D World", IEEE Conference on Computer Vision and Pattern Recognition, Jun. 1, 2007, 6 pages.
Pulli, et al., "Surface Reconstruction and Display from Range and Color Data", Graphical Models, vol. 62, Issue 3, 2000, pp. 165-201.
Pulli, et al., "View-based Rendering: Visualizing Real Objects From Scanned Range and Color Data", Rendering Techniques'97, Springer, Vienna, 1997, 12 pages.
Remondino, et al., "Image-Based 3D Modelling: A Review", The Photogrammetric Record, vol. 21, No. 115, Sep. 2006, pp. 269-291.
Richert, et al., "Intraoral Scanner Technologies: A Review to Make a Successful Impression", Journal of Healthcare Engineering, vol. 2017, Article No. 8427595, 2017, 9 pages.
Sato, "Object Shape and Reflectance Modeling from Color Image Sequence", The Robotics Institute: Carnegie Mellon University, Jan. 1997, 158 pages.
Sato, Yoichi, "Object Shape and Reflectance Modeling from Color Image Sequence", The Robotics Institute: Carnegie Mellon University, 158 pages.
Savarese, et al., "3D Reconstruction by Shadow Carving: Theory and Practical Evaluation", International Journal of Computer Vision, vol. 71, No. 3, Mar. 2007, pp. 1-48.
Schendel, et al., "3D Orthognathic Surgery Simulation Using Image Fusion", Seminars in Orthodontics, vol. 15, No. 1, Mar. 2009, pp. 48-56 (11 pages).
Schropp, Lars, "Shade Matching Assisted by Digital Photography and Computer Software", Journal of Prosthodontics, vol. 18, No. 3, pp. 235-241.
Sinescu, et al., "Laser Beam Used in Dental Scanning for CAD/CAM Technologies", TMJ, vol. 57, No. 2-3, 2007, pp. 187-191 (6 pages).
Slabaugh, et al., "Methods for Volumetric Reconstruction of Visual Scenes", International Journal of Computer Vision, vol. 57, 2004, pp. 179-199 (21 pages).
Slabaugh, Gregory Gibran, "Novel Volumetric Scene Reconstruction Methods for New View Synthesis", PHD Thesis in Electrical and Computer Engineering at Georgia Institute of Technology, Nov. 2002, 209 pages.
Smith, et al., "Digital Signal Processing", , pp. 307-308.
Smith, Steven W, "Digital Signal Processing: A Practical Guide for Engineers and Scientists", , 1998, 5 pages.
Smith, Warren J, "Modern Optical Engineering: The Design of Optical Systems", Third Edition, Exhibit 1065, 2000, 105 pages.
Smith, , "Digital Signal Processing: A Practical Guide for Engineers and Scientists", Demystifying Technology Series, 1998, pp. 307-308.
Spencer, et al., "General Ray-Tracing Procedure", Journal of the Optical Society of America, vol. 52, No. 6, Jun. 1962, pp. 672-678.
Steele, et al., "Bodies in Motion: Monitoring Daily Activity and Exercise with Motion Sensors in People with Chronic Pulmonary Disease", Journal of Rehabilitation Research & Development, vol. 40, No. 5, Suppl. 2, Oct. 2003, pp. 45-58.
Steinbach, et al., "3-D Object Reconstruction Using Spatially Extended Voxels and Multi-Hypothesis Voxel Coloring", Proceedings 15th International Conference on Pattern Recognition, ICPR, vol. 1, 2000, 4 pages.
Tam, et al., "Dental Shade Matching Using a Digital Camera", Journal of Dentistry, vol. 40, Suppl. 2, Dec. 2012, pp. e3-e10.
Tang, et al., "Automatic Reconstruction of as-built Building Information Models from Laser-Scanned Point Clouds: A Review of Related Techniques", Automation in Construction, vol. 19, No. 7, Nov. 1, 2010, pp. 829-843.

(56) References Cited

OTHER PUBLICATIONS

Tiziani, et al., "Theoretical Analysis of Confocal Microscopy with Microlenses", Applied Optics vol. 35, Issue 1, Jan. 1, 1996, pp. 120-125 (7 pages).
Toriwaki, et al., "Fundamentals of Three-Dimensional Digital Image Processing, Springer,", Springer, 2009, 278 pages.
Trevor Darrell and Kwangyoen Woh, "Pyramid Based Depth from Focus", (Darrell), Exhibit 2028., Jun. 1988, pp. 504-509.
Tsukizawa, et al., "3D Digitization of a Hand-held Object with a Wearable Vision Sensor", International Workshop on Computer Vision in Human-Computer Interaction, CVHCI 2004: Computer Vision in Human-Computer Interaction, 2004, pp. 129-141 (11 pages).
Tung, et al., "The Repeatability of an Intraoral Dental Colorimeter", Journal of Prosthetic Dentistry, vol. 88, Issue 6, Dec. 2002, pp. 585-590.
Turner, Daniel, "Hack: The Nintendo Wii", MIT Technology Review, 3 pages.
U.S. Pat. No. 9,962,244, "Declaration of Dr. Chandrajit L. Bajaj, Ph.D. in Support of Post-Grant Review", *Align Technology, Inc.* Petitioner v. *3SHAPE A/S* Patent Owner, Case Nos. PGR2018-00103, Oct. 30, 2018, 1272 pages.
U.S. Appl. No. 15/888,764, "Non-Final Office Action", , 8 pages.
U.S. Pat. No. 10,349,042, "Declaration of Alexander Sergienko, Ph.D.", *Align Technology, Inc.* v. *3Shape A/S*, Case No. IPR2020-01087, Exhibit 2019.
U.S. Pat. No. 10,349,042, "Declaration of Lambertus Hesselink, Ph.D.", *Align Technology, Inc.* v. *3Shape A/S*, Case No. IPR2020-01087, Exhibit 1002.
U.S. Pat. No. 10,349,042, "Declaration of Sylvia D. Hall-Ellis, Ph.D.", *Align Technology, Inc.* v. *3Shape A/S*, Case No. IPR2020-01087, Exhibit 2029.
U.S. Pat. No. 10,349,042, "Deposition Transcript of Dr. Lambertus Hesselink", *Align Technology, Inc.* v. *3Shape A/S*, IPR2020-01087, Exhibit 2030, Sep. 10, 2021, 30 pages.
U.S. Pat. No. 10,349,042, "Deposition Transcript of Dr. Lambertus Hesselink", *Align Technology, Inc.* v. *3Shape A/S*, IPR2020-01087, Exhibit 2023, Apr. 2, 2021 , 82 pages.
U.S. Pat. No. 10,349,042 , "Patent Owner's Preliminary Response to the Petition for Inter Partes Review" , *Align Technology, Inc.* v. *3Shape A/S*, Case No. IPR2020-01088, Exhibit 1062.
U.S. Pat. No. 10,349,042 , "Petition for Inter Partes Review" , *Align Technology, Inc.* Petitioner, v. *3Shape NS*, Patent Owner, Case No. IPR2020-01089.
U.S. Pat. No. 10,349,042 , "Petition for Inter Partes Review" , *Align Technology, Inc.* Petitioner, v. *3SHAPE NS*, Patent Owner, Case No. IPR2020-01088.
U.S. Pat. No. 10,349,042 , "Petition for Inter Partes Review" , *Align Technology, Inc.* Petitioner, v. *3SHAPE NS*, Patent Owner, Case No. IPR2020-01087.
U.S. Pat. No. 10,349,042 , "Reply Declaration of Lambertus Hesselink" , *Align Technology, Inc.* v. *3Shape A/S*, Case No. IPR2020-01087, Exhibit 1057.
U.S. Pat. No. 10,349,042 B1 , "Final Written Decision" , *Align Technology, Inc.* v. *3Shape A/S*, IPR2020-01087 , Jan. 19, 2022 , 59 pages.
U.S. Pat. No. 10,695,151 , "Petition for Inter Partes Review" , , 87 pages.
U.S. Pat. No. 10,728,519 , "Petition for Inter Partes Review" , Align EX1047 *Align* v. *3Shape* IPR2022-00144, Exhibit 1047 , Aug. 20, 2021 , 112 pages.
U.S. Appl. No. 61/420,138 , "Ojelund Provisional", , 45 pages.
U.S. Pat. No. 8,363,228 , "Petition for Inter Partes Review" , *3SHAPE A/S et al.* v. *Align Technology, Inc.*, Case No. IPR2019-00154 , Nov. 10, 2018 , 100 pages.
U.S. Pat. No. 8,363,228 , "Petition for Inter Partes Review", *3Shape A/S et al.* v. *Align Technology, Inc.*, Case No. IPR2019-00157, Exhibit 1063 , Nov. 8, 2018 , 81 pages.

U.S. Pat. No. 9,329,675 , "Decision Denying Institution of Inter Partes Review" , *Align Technology, Inc.*, Petitioner v. *3Shape A/S* Patent Owner, Case IPR2018-00198 , May 30, 2018 , 15 pages.
U.S. Pat. No. 9,329,675 , "Decision Denying Institution of Inter Parties Review" , *Align Technology, Inc.* Petitioner v. *3Shape A/S* Patent Owner, Case IPR2018-00198 , May 30, 2018 , 15 pages.
U.S. Pat. No. 9,329,675 , "Decision Institution of Inter Partes Review", *Align Technology, Inc.*, Petitioner v. *3Shape A/S* Patent Owner, Case IPR2018-00197, May 30, 2018, 32 pages.
U.S. Pat. No. 9,329,675, "Decision Institution of Inter Parties Review", *Align Technology, Inc.*, Petitioner v. *3Shape A/S* Patent Owner, Case IPR2018-00197, May 30, 2018, 32 pages.
U.S. Pat. No. 9,329,675, "Declaration of Dr Chandrajit L Bajaj, Phd. In Support of Inter Partes Review", *Align Technology, Inc.*, Petitioner v. *3Shape A/S* Patent Owner, Case IPR2018-00197.
U.S. Pat. No. 9,329,675, "Declaration of Dr. Chandrajit L. Bajaj, Ph.D. in Support of Inter Partes Review", *Align Technology, Inc.*, Petitioner v. *3SHAPE A/S* Patent Owner, Case IPR2018-00198, Ex. 1003.
U.S. Pat. No. 9,329,675, "Petition for Inter Partes Review", *Align Technology, Inc.*, Petitioner v. *3Shape A/S* Patent Owner, Case IPR2018-00197, Nov. 22, 2017, 67 pages.
U.S. Pat. No. 9,329,675, "Petition for Inter Partes Review", *Align Technology, Inc.*, Petitioner v. *3Shape A/S* Patent Owner, Case IPR2018-00198, Nov. 22, 2017, 78 pages.
U.S. Pat. No. 9,329,675, "PTAB Trial Certificate Inter Partes Review Certificate", IPR Trial No. IPR2018-00197, Oct. 25, 2019, 2 pages.
U.S. Pat. No. 9,675,430, "Declaration of Alexander Sergienko, Ph.D.", *3Shape A/S et al.* v. *Align Technology, Inc.*, Case No. IPR2020-01622, Exhibit 1061.
U.S. Pat. No. 9,962,244, "Corrected Petition for Post-Grant Review", *Align Technology, Inc.*, Petitioner v. *3SHAPE A/S* Patent Owner, Case No. PGR2018-00103, Oct. 30, 2018, 119 pages.
U.S. Pat. No. 9,962,244, "Declaration of Dr. Chandrajit L. Bajaj, Ph.D. in Support of Inter Partes Review", *Align Technology, Inc.*, Petitioner v. *3SHAPE A/S* Patent Owner, Case No. IPR2019-00118, Nov. 5, 2018, 316 pages.
U.S. Pat. No. 9,962,244, "Declaration of Dr. Chandrajit L. Bajaj, Ph.D. In Support Of Inter Partes Review", *Align Technology, Inc.*, Petitioner v. *3SHAPE A/S* Patent Owner, Case No. IPR2019-00117, Nov. 5, 2018, 316 pages.
U.S. Pat. No. 9,962,244, "Declaration of Dr. Chandrajit L. Bajaj, Ph.D. in Support of Post-Grant Review", *Align Technology, Inc.*, Petitioner v. *3SHAPE A/S* Patent Owner, Case No. PGR2018-00104, Oct. 26, 2018, 318 pages.
U.S. Pat. No. 9,962,244, "Declaration of Dr. Chandrajit L. Bajaj, Ph.D. in Support of Post-Grant Review", *Align Technology, Inc.*, Petitioner v. *3SHAPE A/S* Patent Owner, Case Nos. PGR2018-00103, Oct. 30, 2018, 318 pages.
U.S. Pat. No. 9,962,244, "Patent Owner's Preliminary Response to the Petition for Inter Partes Review", *Align Technology, Inc.*, Petitioner v. *3Shape A/S*, Patent Owner, Case No. IPR2019-00118, Mar. 4, 2019, 62 pages.
U.S. Pat. No. 9,962,244, "Patent Owner's Preliminary Response to the Petition for Inter Partes Review", *Align Technology, Inc.*, Petitioner v. *3Shape A/S*, Patent Owner, Case No. IPR2019-00117 , Mar. 4, 2019 , 63 pages.
U.S. Pat. No. 9,962,244, "Patent Owner's Preliminary Response to the Petition for Post-Grant Review", *Align Technology, Inc.*, Petitioner v. *3Shape A/S* Patent Owner, Case No. PGR2018-00103, Feb. 19, 2019, 64 pages.
U.S. Pat. No. 9,962,244, "Patent Owner's Preliminary Response to the Petition for Post-Grant Review", *Align Technology, Inc.*, Petitioner v. *3Shape A/S*, Patent Owner, Case No. PGR2018-00104, Feb. 19, 2019, 64 pages.
U.S. Pat. No. 9,962,244 , "Petition for Inter Partes Review", *Align Technology, Inc.*, Petitioner v. *3Shape, A/S* Patent Owner, Case No. IPR2019-00118, Nov. 5, 2018, 93 pages.
U.S. Pat. No. 9,962,244, "Petition for Inter Partes Review", *Align Technology, Inc.*, Petitioner v. *3Shape A/S*, Patent Owner-Case No. IPR2019-00117, Nov. 5, 2018, 98 pages.

(56) References Cited

OTHER PUBLICATIONS

U.S. Pat. No. 9,962,244, "Petition for Post-Grant Review", *Align Technology, Inc.*, Petitioner v. *3Shape A/S,* Case No. PGR2018-00104, Oct. 26, 2018, 107 pages.
U.S. Pat. No. 9,962,244, "Petition for Post-Grant Review", *Align Technology, Inc.*, Petitioner v. *3SHAPE A/S* Patent Owner, Petitioner, Case No. PGR2018-00103, Oct. 30, 2018, 119 pages.
U.S. Pat. No. 9,962,244, "Second Corrected Declaration of Dr. Chandrajit L. Bajaj, Ph.D. in Support of Post-Grant Review", *Align Technology, Inc.*, Petitioner v. *3SHAPE A/S* Patent Owner, Case No. PGR2018-00103, Oct. 30, 2018, 318 pages.
U.S. Pat. No. 9,962,244, "Second Corrected Petition for Post-Grant Review", *Align Technology, Inc.*, Petitioner v. *3Shape A/S* Patent Owner, Case No. PGR2018-00103, Oct. 30, 2018, 119 pages.
US RE48,221, "Declaration of Dr. Chandrajit L. Bajaj, Ph.D. in Support of Inter Partes Review", Align Technology, Inc., Case IPR2022-00144, Exhibit. 1003.
US RE48,221 , "Petition (1 of 2) for Inter Partes Review", *Align Technology, Inc.*, Petitioner v. *3SHAPE A/S,* Patent Owner, Case No. IPR2022-00144.
US RE48,221 , "Petition (2 of 2) for Inter Partes Review", *Align Technology, Inc.*, Petitioner v. *3SHAPE A/S,* Patent Owner, Case No. IPR2022-00145.
Vadher , et al. , "Basics of Color in Dentistry: A Review", IOSR Journal of Dental and Medical Sciences, vol. 13, Issue 9, Sep. 1, 2014, pp. 78-85.
Vedula , et al. , "Shape and Motion Carving in 6D", Proceedings of the IEEE Conference on Computer Vision and Pattern Recognition, 2000, pp. 1-7.
VIVID 910, "Non-Contact 3-D Digitizer", www.minolta.com.
Vogt, et al. , "An AR System With Intuitive User Interface For Manipulation and Visualization of 3D Medical Data", Studies in Health Technology and Informatics, vol. 98 , 2004., pp. 397-403.
Watanabe, et al. , "Telecentric Optics for Constant-Magnification Imaging", Department of Computer Science, Columbia University, Sep. 1995, 22 pages.
Welch, et al., "High-Performance Wide-Area Optical Tracking The HiBall Tracking System", Presence: Teleoperators and Virtual Environments, vol. 10, No. 1, Feb. 2001, pp. 1-22.
Welch, et al., "Motion Tracking: No Silver Bullet, but a Respectable Arsenal", IEEE Computer Graphics and Applications, vol. 22, No. 6, Dec. 10, 2002, pp. 24-38.
Westphal, et al., "Correction of Geometric and Refractive Image Distortions in Optical Coherence Tomography Applying Fermat's Principle", Optics Express, vol. 10, No. 9, May 6, 2002, pp. 397-404.

Wilson, et al. , "Confocal Microscopy by Aperture Correlation", Optics Letters vol. 21, Issue 23, 1996, pp. 1879-1881 (4 pages).
Wilson, et al. , "Dynamic Lens Compensation for Active Color Imaging and Constant Magnification Focusing", The Robotics Institute, Carnegie Mellon University, Pittsburgh, Pennsylvania 15213, Exhibit 2027, Nov. 1991 , 52 pages.
Wilson, et al., "Real-Time Three-Dimensional Imaging of Macroscopic Structures", Journal of Microscopy, vol. 191, No. 2 , Aug. 1998, pp. 116-118.
Xia, et al., "Three-Dimensional Virtual-Reality Surgical Planning and Soft-Tissue Prediction for Orthognathic Surgery", IEEE Transactions on Information Technology in Biomedicine, vol. 5, No. 2, Jun. 2001 , pp. 97-107.
Xiao, et al., "Efficient Partial-Surface Registration for 3D Objects", Computer Vision and Image Understanding, vol. 98, No. 2, 2005, pp. 271-294.
Yamany, et al., "Free-Form Surface Registration Using Surface Signatures", The Proceedings of the Seventh IEEE International Conference on Computer Vision, vol. 2, Sep. 1999, 7 pages.
Yang, et al., "Dealing with Textureless Regions and Specular Highlights—A Progressive Space Carving Scheme Using a Novel Photo-Consistency Measure", Proceedings of the Ninth IEEE International Conference on Computer Vision (ICCV 2003) 2-vol. Set, Oct. 2003, 9 pages.
Yoshida, et al., "Intraoral Ultrasonic Scanning as a Diagnostic Aid", Journal of Cranio-Maxillofacial Surgery, vol. 15, Dec. 1987, pp. 306-311.
Yoshizawa, Toru, "Exhibit 6—Latest Optical 3D Measurement", Nov. 20, 2006, 16 pages.
Yoshizawa, Toru, "Handbook of Optical Metrology Principles and Application", Second Edition, 15 pages.
Yoshizawa,, Toru , "Handbook of Optical Metrology Principles and Application", , Feb. 25, 2009 , pp. 135-153.
Yuan , et al. , "Inferring 3D Volumetric Shape of Both Moving Objects and Static Background Observed by a Moving Camera", IEEE Conference on Computer Vision and Pattern Recognition , Jun. 2007 , 8 pages.
Zhang , et al. , "A 3-dimensional Vision System for Dental Applications" , Proceedings of the 29th Annual International , Aug. 23-26, 2007 , pp. 3369-3372.
Zhang , et al. , "Projection Defocus Analysis for Scene Capture and Image Display" , ACM SIGGRAPH , Jul. 1, 2006 , pp. 907-915.
Office Action issued on Feb. 21, 2025, by the U.S. Patent and Trademark Office in co-pending U.S. Appl. No. 18/455,708. (11 pages).

* cited by examiner

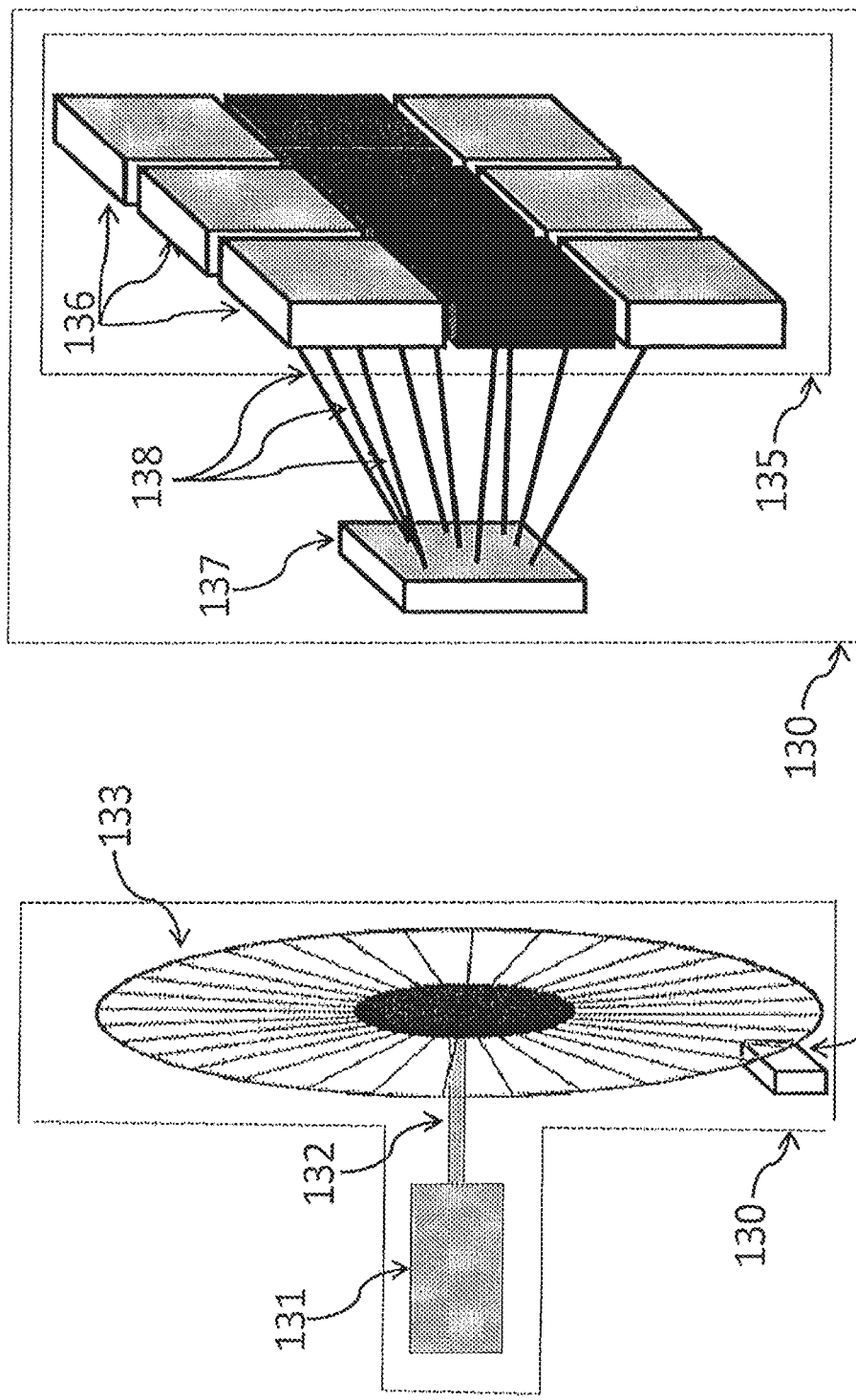

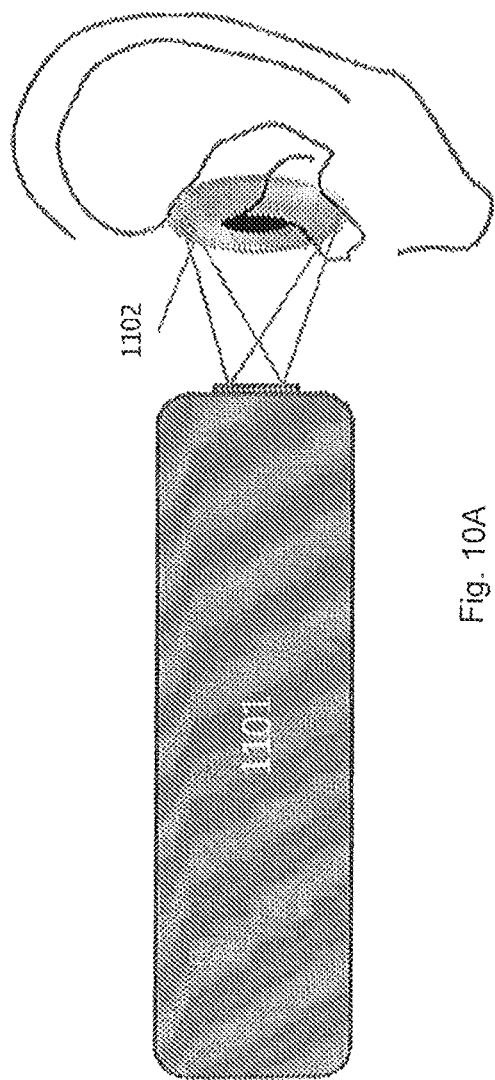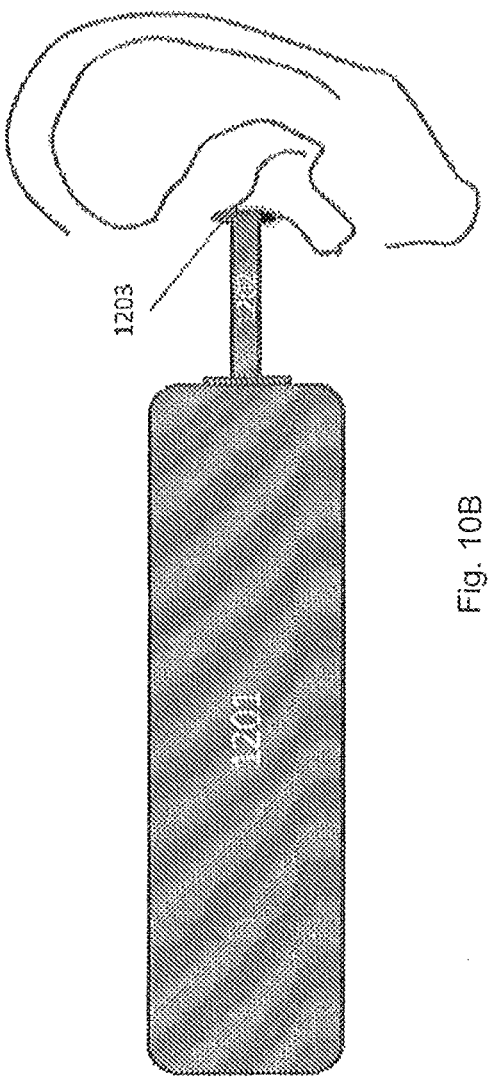

INTRAORAL SCANNING APPARATUS

CROSS-REFERENCE TO RELATED APPLICATIONS

The present application is a continuation of U.S. Ser. No. 18/455,708, filed on Aug. 25, 2023, which is a continuation of U.S. Ser. No. 17/892,397, filed Aug. 22, 2022, which is a continuation of U.S. Ser. No. 17/742,115, filed on May 11, 2022, which is a continuation of U.S. Ser. No. 17/533,403, filed on Nov. 23, 2021, which is a continuation of U.S. Ser. No. 17/340,806, filed Jun. 7, 2021, which is a continuation of U.S. Ser. No. 17/206,581, filed on Mar. 19, 2021, now U.S. Pat. No. 11,076,146, which is a continuation of U.S. Ser. No. 16/774,843, filed on Jan. 28, 2020, now U.S. Pat. No. 11,051,002, which is a continuation of U.S. Ser. No. 16/433,369, filed on Jun. 6, 2019, now U.S. Pat. No. 10,595,010, which is a continuation of U.S. Ser. No. 16/217,943, filed on Dec. 12, 2018, now U.S. Pat. No. 10,326,982, which is a continuation of U.S. Ser. No. 15/974,105, filed on May 8, 2018, now U.S. Pat. No. 10,349,041, which is a continuation of U.S. Ser. No. 14/502,230, filed on Sep. 30, 2014, now U.S. Pat. No. 10,097,815, which in turn is a continuation of U.S. Ser. No. 13/376,427, filed on Dec. 6, 2011, now U.S. Pat. No. 8,878,905, which is a national stage application of PCT/DK2010/050148, filed on Jun. 17, 2010, and which claims the benefit of U.S. 61/187,744, filed on Jun. 17, 2009, and U.S. 61/231,118, filed on Aug. 4, 2009, the contents of all of which are incorporated herein by reference in their entirety.

FIELD OF THE INVENTION

The present disclosure relates to an apparatus and a method for optical 3D scanning of surfaces. The principle of the apparatus and method according to the disclosure may be applied in various contexts. One specific embodiment of the invention is particularly suited for intraoral scanning, i.e. direct scanning of teeth and surrounding soft-tissue in the oral cavity. Other dental related embodiments of the invention are suited for scanning dental impressions, gypsum models, wax bites, dental prosthetics and abutments. Another embodiment of the invention is suited for scanning of the interior and exterior part of a human ear or ear channel impressions. The disclosure may find use within scanning of the 3D structure of skin in dermatological or cosmetic/cosmetological applications, scanning of jewelry or wax models of whole jewelry or part of jewelry, scanning of industrial parts and even time resolved 3D scanning, such as time resolved 3D scanning of moving industrial parts.

BACKGROUND

The disclosure relates to three dimensional (3D) scanning of the surface geometry of objects. Scanning an object surface in 3 dimensions is a well-known field of study and the methods for scanning can be divided into contact and non-contact methods. An example of contact measurements methods are Coordinate Measurement Machines (CMM), which measures by letting a tactile probe trace the surface. The advantages include great precision, but the process is slow and a CMM is large and expensive. Non-contact measurement methods include x-ray and optical probes.

Confocal microscopy is an optical imaging technique used to increase micrograph contrast and/or to reconstruct three-dimensional images by using a spatial pinhole to eliminate out-of-focus light or flare in specimens that are thicker than the focal plane.

A confocal microscope uses point illumination and a pinhole in an optically conjugate plane in front of the detector to eliminate out-of-focus information. Only the light within the focal plane can be detected. As only one point is illuminated at a time in confocal microscopy, 2D imaging requires raster scanning and 3D imaging requires raster scanning in a range of focus planes.

In WO 00/08415 the principle of confocal microscopy is applied by illuminating the surface with a plurality of illuminated spots. By varying the focal plane in-focus spot-specific positions of the surface can be determined. However, determination of the surface structure is limited to the parts of the surface that are illuminated by a spot.

WO 2003/060587 relates to optically sectioning of a specimen in microscopy wherein the specimen is illuminated with an illumination pattern. Focus positions of the image plane are determined by characterizing an oscillatory component of the pattern. However, the focal plane can only be adjusted by moving the specimen and the optical system relative to each other, i.e. closer to or further away from each other. Thus, controlled variation of the focal plane requires a controlled spatial relation between the specimen and the optical system, which is fulfilled in a microscope. However, such a controlled spatial relation is not applicable to e.g. a hand held scanner.

US2007/0109559 A1 describes a focus scanner where distances are found from the focus lens positions at which maximum reflective intensity of light beams incident on the object being scanned is observed. In contrast to the disclosure disclosed here, this prior art exploits no pre-determined measure of the illumination pattern and exploits no contrast detection, and therefore, the signal-to-noise ratio is sub-optimal.

In WO 2008/125605, means for generating a time-variant pattern composed of alternating split images are described. This document describes a scanning method to obtain an optical section of a scan object by means of two different illumination profiles, e.g. two patterns of opposite phases. These two images are used to extract the optical section, and the method is limited to acquisition of images from only two different illumination profiles.

Furthermore, the method relies on a predetermined calibration that determines the phase offset between the two illumination profiles.

SUMMARY

Thus, an object of the disclosure is to provide a scanner which may be integrated in a manageable housing, such as a handheld housing. Further objects of the disclosure are: discriminate out-of-focus information and provide a fast scanning time.

This is achieved by a method and a scanner for obtaining and/or measuring the 3D geometry of at least a part of the surface of an object, said scanner comprising:
  at least one camera accommodating an array of sensor elements,
  means for generating a probe light incorporating a spatial pattern,
  means for transmitting the probe light towards the object thereby illuminating at least a part of the object with said pattern in one or more configurations,
  means for transmitting at least a part of the light returned from the object to the camera, means for varying the position of the focus plane of the pattern on the object while maintaining a fixed spatial relation of the scanner and the object, means for obtaining at least one image from said array of sensor elements, means for evaluating a correlation measure at each focus plane position between at least one image pixel and a weight function, where the weight function is determined based on information of the configuration of the spatial pattern;

data processing means for:
a) determining by analysis of the correlation measure the in-focus position(s) of:
   each of a plurality of image pixels for a range of focus plane positions, or
   each of a plurality of groups of image pixels for a range of focus plane positions, and
b) transforming in-focus data into 3D real world coordinates.

The method and apparatus described in this disclosure is for providing a 3D surface registration of objects using light as a non-contact probing agent. The light is provided in the form of an illumination pattern to provide a light oscillation on the object. The variation/oscillation in the pattern may be spatial, e.g. a static checkerboard pattern, and/or it may be time varying, for example by moving a pattern across the object being scanned. The disclosure provides for a variation of the focus plane of the pattern over a range of focus plane positions while maintaining a fixed spatial relation of the scanner and the object. It does not mean that the scan must be provided with a fixed spatial relation of the scanner and the object, but merely that the focus plane can be varied (scanned) with a fixed spatial relation of the scanner and the object. This provides for a hand held scanner solution based on the present disclosure.

In some embodiments the signals from the array of sensor elements are light intensity.

One embodiment of the invention comprises a first optical system, such as an arrangement of lenses, for transmitting the probe light towards the object and a second optical system for imaging light returned from the object to the camera. In the preferred embodiment of the invention only one optical system images the pattern onto the object and images the object, or at least a part of the object, onto the camera, preferably along the same optical axis, however along opposite optical paths.

In the preferred embodiment of the invention an optical system provides an imaging of the pattern onto the object being probed and from the object being probed to the camera. Preferably, the focus plane is adjusted in such a way that the image of the pattern on the probed object is shifted along the optical axis, preferably in equal steps from one end of the scanning region to the other. The probe light incorporating the pattern provides a pattern of light and darkness on the object. Specifically, when the pattern is varied in time for a fixed focus plane then the in-focus regions on the object will display an oscillating pattern of light and darkness. The out-of-focus regions will display smaller or no contrast in the light oscillations.

Generally we consider the case where the light incident on the object is reflected diffusively and/or specularly from the object's surface. But it is understood that the scanning apparatus and method are not limited to this situation. They are also applicable to e.g. the situation where the incident light penetrates the surface and is reflected and/or scattered and/or gives rise to fluorescence and/or phosphorescence in the object. Inner surfaces in a sufficiently translucent object may also be illuminated by the illumination pattern and be imaged onto the camera. In this case a volumetric scanning is possible. Some planktic organisms are examples of such objects.

When a time varying pattern is applied a single sub-scan can be obtained by collecting a number of 2D images at different positions of the focus plane and at different instances of the pattern. As the focus plane coincides with the scan surface at a single pixel position, the pattern will be projected onto the surface point in-focus and with high contrast, thereby giving rise to a large variation, or amplitude, of the pixel value over time. For each pixel it is thus possible to identify individual settings of the focusing plane for which each pixel will be in focus. By using knowledge of the optical system used, it is possible to transform the contrast information vs. position of the focus plane into 3D surface information, on an individual pixel basis.

Thus, in one embodiment of the disclosure the focus position is calculated by determining the light oscillation amplitude for each of a plurality of sensor elements for a range of focus planes.

For a static pattern a single sub-scan can be obtained by collecting a number of 2D images at different positions of the focus plane. As the focus plane coincides with the scan surface, the pattern will be projected onto the surface point in-focus and with high contrast. The high contrast gives rise to a large spatial variation of the static pattern on the surface of the object, thereby providing a large variation, or amplitude, of the pixel values over a group of adjacent pixels. For each group of pixels it is thus possible to identify individual settings of the focusing plane for which each group of pixels will be in focus. By using knowledge of the optical system used, it is possible to transform the contrast information vs. position of the focus plane into 3D surface information, on an individual pixel group basis.

Thus, in one embodiment of the invention the focus position is calculated by determining the light oscillation amplitude for each of a plurality of groups of the sensor elements for a range of focus planes.

The 2D to 3D conversion of the image data can be performed in a number of ways known in the art. I.e. the 3D surface structure of the probed object can be determined by finding the plane corresponding to the maximum light oscillation amplitude for each sensor element, or for each group of sensor elements, in the camera's sensor array when recording the light amplitude for a range of different focus planes. Preferably, the focus plane is adjusted in equal steps from one end of the scanning region to the other. Preferably the focus plane can be moved in a range large enough to at least coincide with the surface of the object being scanned.

The present disclosure distinguishes itself from WO 2008/125605, because in the embodiments of the present invention that use a time-variant pattern, input images are not limited to two illumination profiles and can be obtained from any illumination profile of the pattern. This is because the orientation of the reference image does not rely entirely on a predetermined calibration, but rather on the specific time of the input image acquisition.

Thus WO 2008/125605 applies specifically exactly two patterns, which are realized physically by a chrome-on-glass mask as illuminated from either side, the reverse side being reflective. WO 2008/125605 thus has the advantage of using no moving parts, but the disadvantage of a comparatively poorer signal-to-noise ratio. In the present disclosure there is the possibility of using any number of pattern configurations, which makes computation of the light oscillation amplitude or the correlation measure more precise.

Definitions

Pattern: A light signal comprising an embedded spatial structure in the lateral plane. May also be termed "illumination pattern".

Time varying pattern: A pattern that varies in time, i.e. the embedded spatial structure varies in time. May also be termed "time varying illumination pattern". In the following also termed "fringes".

Static pattern: A pattern that does not vary in time, e.g. a static checkerboard pattern or a static line pattern.

Pattern configuration: The state of the pattern. Knowledge of the pattern configuration at a certain time amounts to knowing the spatial structure of the illumination at that time. For a periodic pattern the pattern configuration will include information of the pattern phase. If a surface element of the object being scanned is imaged onto the camera then knowledge of the pattern configuration amounts to knowledge of what part of the pattern is illuminating the surface element.

Focus plane: A surface where light rays emitted from the pattern converge to form an image on the object being scanned. The focus plane does not need to be flat. It may be a curved surface.

Optical system: An arrangement of optical components, e.g. lenses, that transmit, collimate and/or images light, e.g. transmitting probe light towards the object, imaging the pattern on and/or in the object, and imaging the object, or at least a part of the object, on the camera.

Optical axis: An axis defined by the propagation of a light beam. An optical axis is preferably a straight line. In the preferred embodiment of the invention the optical axis is defined by the configuration of a plurality of optical components, e.g. the configuration of lenses in the optical system. There may be more than one optical axis, if for example one optical system transmits probe light to the object and another optical system images the object on the camera. But preferably the optical axis is defined by the propagation of the light in the optical system transmitting the pattern onto the object and imaging the object onto the camera. The optical axis will often coincide with the longitudinal axis of the scanner.

Optical path: The path defined by the propagation of the light from the light source to the camera. Thus, a part of the optical path preferably coincides with the optical axis. Whereas the optical axis is preferably a straight line, the optical path may be a non-straight line, for example when the light is reflected, scattered, bent, divided and/or the like provided e.g. by means of beam splitters, mirrors, optical fibers and the like.

Telecentric system: An optical system that provides imaging in such a way that the chief rays are parallel to the optical axis of said optical system. In a telecentric system out-of-focus points have substantially same magnification as in-focus points. This may provide an advantage in the data processing. A perfectly telecentric optical system is difficult to achieve, however an optical system which is substantially telecentric or near telecentric may be provided by careful optical design. Thus, when referring to a telecentric optical system it is to be understood that it may be only near telecentric.

Scan length: A lateral dimension of the field of view. If the probe tip (i.e. scan head) comprises folding optics to direct the probe light in a direction different such as perpendicular to the optical axis then the scan length is the lateral dimension parallel to the optical axis.

Scan object: The object to be scanned and on which surface the scanner provides information. "The scan object" may just be termed "the object".

Camera: Imaging sensor comprising a plurality of sensors that respond to light input onto the imaging sensor. The sensors are preferably ordered in a 2D array in rows and columns.

Input signal: Light input signal or sensor input signal from the sensors in the camera. This can be integrated intensity of light incident on the sensor during the exposure time or integration of the sensor. In general, it translates to a pixel value within an image. May also be termed "sensor signal".

Reference signal: A signal derived from the pattern. A reference signal may also be denoted a weight function or weight vector or reference vector.

Correlation measure: A measure of the degree of correlation between a reference and input signal. Preferably the correlation measure is defined such that if the reference and input signal are linearly related to each other than the correlation measure obtains a larger magnitude than if they are not. In some cases the correlation measure is a light oscillation amplitude.

Image: An image can be viewed as a 2D array of values (when obtained with a digital camera) or in optics, an image indicates that there exists a relation between an imaged surface and an image surface where light rays emerging from one point on said imaged surface substantially converge on one point on said image surface.

Intensity: In optics, intensity is a measure of light power per unit area. In image recording with a camera comprising a plurality of individual sensing elements, intensity may be used to term the recorded light signal on the individual sensing elements. In this case intensity reflects a time integration of light power per unit area on the sensing element over the exposure time involved in the image recording.

Mathematical Notation

A A correlation measure between the weight function and the recorded light signal. This can be a light oscillation amplitude.

l Light input signal or sensor input signal. This can be integrated intensity of light incident on the sensor during the exposure time or integration of the sensor. In general, it translates to a pixel value within an image.

f Reference signal. May also be called weight value.

n The number of measurements with a camera sensor and/or several camera sensors that are used to compute a correlation measure.

H Image height in number of pixels

W Image width in number of pixels

Symbols are also explained as needed in the text.

DETAILED DESCRIPTION OF THE PREFERRED EMBODIMENTS

The scanner preferably comprises at least one beam splitter located in the optical path. For example, an image of the object may be formed in the camera by means of a beam splitter. Exemplary uses of beam splitters are illustrated in the figures.

In a preferred embodiment of the invention light is transmitted in an optical system comprising a lens system. This lens system may transmit the pattern towards the object and images light reflected from the object to the camera.

In a telecentric optical system, out-of-focus points have the same magnification as in-focus points. Telecentric projection can therefore significantly ease the data mapping of acquired 2D images to 3D images. Thus, in a preferred embodiment of the invention the optical system is substantially telecentric in the space of the probed object. The optical system may also be telecentric in the space of the pattern and camera.

Varying Focus

A pivotal point of the disclosure is the variation, i.e. scanning, of the focal plane without moving the scanner in relation to the object being scanned. Preferably the focal plane may be varied, such as continuously varied in a periodic fashion, while the pattern generation means, the camera, the optical system and the object being scanned is fixed in relation to each other. Further, the 3D surface acquisition time should be small enough to reduce the impact of relative movement between probe and teeth, e.g. reduce effect of shaking. In the preferred embodiment of the invention the focus plane is varied by means of at least one focus element. Preferably the focus plane is periodically varied with a predefined frequency. Said frequency may be at least 1 Hz, such as at least 2 Hz, 3, 4, 5, 6, 7, 8, 9 or at least 10 Hz, such as at least 20, 40, 60, 80 or at least 100 Hz.

Preferably the focus element is part of the optical system. I.e. the focus element may be a lens in a lens system. A preferred embodiment comprises means, such as a translation stage, for adjusting and controlling the position of the focus element. In that way the focus plane may be varied, for example by translating the focus element back and forth along the optical axis.

If a focus element is translated back and forth with a frequency of several Hz this may lead to instability of the scanner. A preferred embodiment of the invention thus comprises means for reducing and/or eliminating the vibration and/or shaking from the focus element adjustment system, thereby increasing the stability of the scanner. This may at least partly be provided by means for fixing and/or maintaining the centre of mass of the focus element adjustment system, such as a counter-weight to substantially counter-balance movement of the focus element; for example, by translating a counter-weight opposite to the movement of the focus element. Ease of operation may be achieved if the counter-weight and the focus element are connected and driven by the same translation means. This may however, only substantially reduce the vibration to the first order. If a counter-weight balanced device is rotated around the counter-weight balanced axis, there may be issues relating to the torque created by the counter-weights. A further embodiment of the invention thus comprises means for reducing and/or eliminating the first order, second order, third order and/or higher order vibration and/or shaking from the focus element adjustment system, thereby increasing the stability of the scanner.

In another embodiment of the invention more than one optical element is moved to shift the focal plane. In that embodiment it is desirable that these elements are moved together and that the elements are physically adjacent.

In the preferred embodiment of the invention the optical system is telecentric, or near telecentric, for all focus plane positions. Thus, even though one or more lenses in the optical system may be shifted back and forth to change the focus plane position, the telecentricity of the optical system is maintained.

The preferred embodiment of the invention comprises focus gearing. Focus gearing is the correlation between movement of the lens and movement of the focus plane position. E.g. a focus gearing of 2 means that a translation of the focus element of 1 mm corresponds to a translation of the focus plane position of 2 mm. Focus gearing can be provided by a suitable design of the optical system. The advantage of focus gearing is that a small movement of the focus element may correspond to a large variation of the focus plane position. In specific embodiments of the invention the focus gearing is between 0.1 and 100, such as between 0.1 and 1, such as between 1 and 10, such as between 2 and 8, such as between 3 and 6, such as least 10, such as at least 20.

In another embodiment of the invention the focus element is a liquid lens. A liquid lens can control the focus plane without use of any moving parts.

Camera

The camera may be a standard digital camera accommodating a standard CCD or CMOS chip with one A/D converter per line of sensor elements (pixels). However, to increase the frame rate the scanner according to the disclosure may comprise a high-speed camera accommodating multiple A/D converters per line of pixels, e.g. at least 2, 4, 8 or 16 A/D converters per line of pixels.

Pattern

Another central element of the disclosure is the probe light with an embedded pattern that is projected on to the object being scanned. The pattern may be static or time varying. The time varying pattern may provide a variation of light and darkness on and/or in the object. Specifically, when the pattern is varied in time for a fixed focus plane then the in-focus regions on the object will display an oscillating pattern of light and darkness. The out-of-focus regions will display smaller or no contrast in the light oscillations. The static pattern may provide a spatial variation of light and darkness on and/or in the object. Specifically, the in-focus regions will display an oscillating pattern of light and darkness in space. The out-of-focus regions will display smaller or no contrast in the spatial light oscillations.

Light may be provided from an external light source, however preferably the scanner comprises at least one light source and pattern generation means to produce the pattern. It is advantageous in terms of signal-to-noise ratio to design a light source such that the intensity in the non-masked parts of the pattern is as close to uniform in space as possible. In another embodiment the light source and the pattern generation means is integrated in a single component, such as a segmented LED. A segmented LED may provide a static pattern and/or it may provide a time varying pattern in itself by turning on and off the different segments in sequence. In one embodiment of the invention the time varying pattern is periodically varying in time. In another embodiment of the invention the static pattern is periodically varying in space.

Light from the light source (external or internal) may be transmitted through the pattern generation means thereby generating the pattern. For example the pattern generation means comprises at least one translucent and/or transparent pattern element. For generating a time varying pattern a wheel, with an opaque mask can be used. E.g. the mask comprises a plurality of radial spokes, preferably arranged in a symmetrical order. The scanner may also comprise means for rotating and/or translating the pattern element. For generating a static pattern a glass plate with an opaque mask can be used. E.g. the mask comprises a line pattern or checkerboard pattern. In general said mask preferably possesses rotational and/or translational periodicity. The pattern element is located in the optical path. Thus, light from the light source may be transmitted through the pattern element, e.g. transmitted transversely through the pattern element.

The time varying pattern can then be generated by rotating and/or translating the pattern element. A pattern element generating a static pattern does not need to be moved during a scan.

Correlation

One object of the disclosure is to provide short scan time and real time processing, e.g. to provide live feedback to a scanner operator to make a fast scan of an entire tooth arch. However, real time high resolution 3D scanning creates an enormous amount of data. Therefore data processing should be provided in the scanner housing, i.e. close to the optical components, to reduce data transfer rate to e.g. a cart, workstation or display. In order to speed up data processing time and in order to extract in-focus information with an optimal signal-to-noise ratio various correlation techniques may be embedded/implemented. This may for example be implemented in the camera electronics to discriminate out-of-focus information. The pattern is applied to provide illumination with an embedded spatial structure on the object being scanned. Determining in-focus information relates to calculating a correlation measure of this spatially structured light signal (which we term input signal) with the variation of the pattern itself (which we term reference signal). In general the magnitude of the correlation measure is high if the input signal coincides with the reference signal. If the input signal displays little or no variation then the magnitude of the correlation measure is low. If the input signal displays a large spatial variation but this variation is different than the variation in the reference signal then the magnitude of the correlation measure is also low. In a further embodiment of the invention the scanner and/or the scanner head may be wireless, thereby simplifying handling and operation of the scanner and increasing accessibility under difficult scanning situations, e.g. intra-oral or in the ear scanning. However, wireless operation may further increase the need for local data processing to avoid wireless transmission of raw 3D data.

The reference signal is provided by the pattern generating means and may be periodic. The variation in the input signal may be periodic and it may be confined to one or a few periods. The reference signal may be determined independently of the input signal. Specifically in the case of a periodic variation, the phase between the oscillating input and reference signal may be known independently of the input signal. In the case of a periodic variation the correlation is typically related to the amplitude of the variation. If the phase between the oscillating input and reference signals is not known it is necessary to determine both cosine and sinusoidal part of the input signal before the input signal's amplitude of variation can be determined. This is not necessary when the phase is known.

One way to define the correlation measure mathematically with a discrete set of measurements is as a dot product computed from a signal vector, $I=(I_1, \ldots, I_n)$, with $n>1$ elements representing sensor signals and a reference vector, $f=(f_1, \ldots, f_n)$, of same length as said signal vector of reference weights. The correlation measure A is then given by $$A = f \cdot I = \sum_{i=1}^{n} f_i I_i$$

The indices on the elements in the signal vector represent sensor signals that are recorded at different times and/or at different sensors. In the case of a continuous measurement the above expression is easily generalized to involve integration in place of the summation. In that case the integration parameter is time and/or one or more spatial coordinates.

A preferred embodiment is to remove the DC part of the correlation signal or correlation measure, i.e., when the reference vector elements sums to zero ($\Sigma_{i=1}^{n} f_i=0$). The focus position can be found as an extremum of the correlation measure computed over all focus element positions. We note that in this case the correlation measure is proportional to the sample Pearson correlation coefficient between two variables. If the DC part is not removed, there may exist a trend in DC signal over all focus element positions, and this trend can be dominating numerically. In this situation, the focus position may still be found by analysis of the correlation measure and/or one or more of its derivatives, preferably after trend removal.

Preferably, the global extremum should be found. However, artifacts such as dirt on the optical system can result in false global maxima. Therefore, it can be advisable to look for local extrema in some cases. If the object being scanned is sufficiently translucent it may be possible to identify interior surfaces or surface parts that are otherwise occluded. In such cases there may be several local extrema that corresponds to surfaces and it may be advantageous to process several or all extrema.

The correlation measure can typically be computed based on input signals that are available as digital images, i.e., images with a finite number of discrete pixels. Therefore conveniently, the calculations for obtaining correlation measures can be performed for image pixels or groups thereof. Correlation measures can then be visualized in as pseudo-images.

The correlation measure applied in this disclosure is inspired by the principle of a lock-in amplifier, in which the input signal is multiplied by the reference signal and integrated over a specified time. In this disclosure, a reference signal is provided by the pattern.

Temporal Correlation

Temporal correlation involves a time-varying pattern. The light signal in the individual light sensing elements in the camera is recorded several times while the pattern configuration is varied. The correlation measure is thus at least computed with sensor signals recorded at different times.

A principle to estimate light oscillation amplitude in a periodically varying light signal is taught in WO 98/45745 where the amplitude is calculated by first estimating a cosine and a sinusoidal part of the light intensity oscillation. However, from a statistical point of view this is not optimal because two parameters are estimated to be able to calculate the amplitude.

In this embodiment of the invention independent knowledge of the pattern configuration at each light signal recording allows for calculating the correlation measure at each light sensing element.

In some embodiments of the invention the scanner comprises means for obtaining knowledge of the pattern configuration. To provide such knowledge the scanner preferably further comprises means for registering and/or monitoring the time varying pattern.

Each individual light sensing element, i.e. sensor element, in the camera sees a variation in the light signal corresponding to the variation of the light illuminating the object.

One embodiment of the invention obtains the time variation of the pattern by translating and/or rotating the pattern element. In this case the pattern configuration may be obtained by means of a position encoder on the pattern element combined with prior knowledge of the pattern geometry that gives rise to a pattern variation across individual sensing elements. Knowledge of the pattern configuration thus arises as a combination of knowledge of the pattern geometry that results in a variation across different sensing elements and pattern registration and/or monitoring during the 3D scan. In case of a rotating wheel as the pattern element the angular position of the wheel may then be obtained by an encoder, e.g. mounted on the rim.

One embodiment of the invention involves a pattern that possesses translational and/or rotational periodicity. In this embodiment there is a well-defined pattern oscillation period if the pattern is substantially translated and/or rotated at a constant speed.

One embodiment of the invention comprises means for sampling each of a plurality of the sensor elements a plurality of times during one pattern oscillation period, preferably sampled an integer number of times, such as sampling 2, 3, 4, 5, 6, 7 or 8 times during each pattern oscillation period, thereby determining the light variation during a period.

The temporal correlation measure between the light variation and the pattern can be obtained by recording several images on the camera during one oscillation period (or at least one oscillation period). The number of images recorded during one oscillation period is denoted n. The registration of the pattern position for each individual image combined with the independently known pattern variation over all sensing element (i.e. obtaining knowledge of the pattern configuration) and the recorded images allows for an efficient extraction of the correlation measure in each individual sensing element in the camera. For a light sensing element with label j, the n recorded light signals of that element are denoted $1_{1,j}, \ldots 1_{n,j}$. The correlation measure of that element, $A_j$, may be expressed as $$A_j = \sum_{i=1}^{n} f_{i,j} I_{i,j}$$

Here the reference signal or weight function $f$ is obtained from the knowledge of the pattern configuration. $f$ has two indices i,j. The variation of $f$ with the first index is derived from the knowledge of the pattern position during each image recording. The variation of $f$ with the second index is derived from the knowledge of the pattern geometry which may be determined prior to the 3D scanning.

Preferably, but not necessarily, the reference signal $f$ averages to zero over time, i.e. for all j we have $$\sum_{i=1}^{n} f_{i,j} = 0$$

to suppress the DC part of the light variation or correlation measure. The focus position corresponding to the pattern being in focus on the object for a single sensor element in the camera will be given by an extremum value of the correlation measure of that sensor element when the focus position is varied over a range of values. The focus position may be varied in equal steps from one end of the scanning region to the other.

To obtain a sharp image of an object by means of a camera the object must be in focus and the optics of the camera and the object must be in a fixed spatial relationship during the exposure time of the image sensor of the camera. Applied to the present disclosure this should imply that the pattern and the focus should be varied in discrete steps to be able to fix the pattern and the focus for each image sampled in the camera, i.e. fixed during the exposure time of the sensor array. However, to increase the sensitivity of the image data the exposure time of the sensor array should be as high as the sensor frame rate permits. Thus, in the preferred embodiment of the invention images are recorded (sampled) in the camera while the pattern is continuously varying (e.g. by continuously rotating a pattern wheel) and the focus plane is continuously moved. This implies that the individual images will be slightly blurred since they are the result of a time-integration of the image while the pattern is varying and the focus plane is moved. This is something that one could expect to lead to deterioration of the data quality, but in practice the advantage of concurrent variation of the pattern and the focus plane is bigger than the drawback.

In another embodiment of the invention images are recorded (sampled) in the camera while the pattern is fixed and the focus plane is continuously moved, i.e. no movement of the pattern. This could be the case when the light source is a segmented light source, such as a segment LED that flashes in an appropriate fashion. In this embodiment the knowledge of the pattern is obtained by a combination of prior knowledge of the geometry of the individual segments on the segmented LED give rise to a variation across light sensing elements and the applied current to different segments of the LED at each recording.

In yet another embodiment of the invention images are recorded (sampled) in the camera while the pattern is continuously varying and the focus plane is fixed.

In yet another embodiment of the invention images are recorded (sampled) in the camera while the pattern and the focus plane are fixed.

The temporal correlation principle may be applied in general within image analysis. Thus, a further embodiment of the invention relates to a method for calculating the amplitude of a light intensity oscillation in at least one (photoelectric) light sensitive element, said light intensity oscillation generated by a periodically varying illumination pattern and said amplitude calculated in at least one pattern oscillation period, said method comprising the steps of:
  providing the following a predetermined number of sampling times during a pattern oscillation period:
    sampling the light sensitive element thereby providing the signal of said light sensitive element, and
    providing an angular position and/or a phase of the periodically varying illumination pattern for said sampling, and
  calculating said amplitude(s) by integrating the products of a predetermined periodic function and the signal of the corresponding light sensitive element over said predetermined number of sampling times, wherein said periodic function is a function of the angular position and/or the phase of the periodically varying illumination pattern.

This may also be expressed as $$A = \sum_{i} f(p_i) I_i$$

where A is the calculated amplitude or correlation measure, i is the index for each sampling, $f$ is the periodic function, $p_i$ is the angular position/phase of the illumination pattern for sampling i and $l_i$ is the signal of the light sensitive element for sampling i. Preferably the periodic function averages to zero over a pattern oscillation period, i.e. $\Sigma_i f(p_i)=0$.

To generalize the principle to a plurality of light sensitive elements, for example in a sensor array, the angular position/phase of the illumination pattern for a specific light sensitive element may consist of an angular position/phase associated with the illumination pattern plus a constant offset associated with the specific light sensitive element. Thereby the correlation measure or amplitude of the light oscillation in light sensitive element j may be expressed as $$A_j = \sum_i f(\theta_j + p_i)I_{i,j},$$

where $\theta_j$ is the constant offset for light sensitive element j.

A periodically varying illumination pattern may be generated by a rotating wheel with an opaque mask comprising a plurality of radial spokes arranged in a symmetrical order. The angular position of the wheel will thereby correspond to the angular position of the pattern and this angular position may obtained by an encoder mounted on the rim of the wheel. The pattern variation across different sensor elements for different position of the pattern may be determined prior to the 3D scanning in a calibration routine. A combination of knowledge of this pattern variation and the pattern position constitutes knowledge of the pattern configuration. A period of this pattern may for example be the time between two spokes and the amplitude of a single or a plurality of light sensitive elements of this period may be calculated by sampling e.g. four times in this period.

A periodically varying illumination pattern may generated by a Ronchi ruling moving orthogonal to the lines and the position is measured by an encoder. This position corresponds to the angular position of the generated pattern. Alternatively, a checkerboard pattern could be used.

A periodically varying illumination pattern may generated by a one-dimensional array of LEDs that can be controlled line wise.

A varying illumination pattern may generated by a LCD or DLP based projector.

Optical Correlation

The abovementioned correlation principle (temporal correlation) requires some sort of registering of the time varying pattern, e.g. knowledge of the pattern configuration at each light level recording in the camera. However, a correlation principle without this registering may be provided in another embodiment of the invention. This principle is termed "optical correlation".

In this embodiment of the invention an image of the pattern itself and an image of at least a part of the object being scanned with the pattern projected onto it is combined on the camera. I.e. the image on the camera is a superposition of the pattern itself and the object being probed with the pattern projected onto it. A different way of expressing this is that the image on the camera substantially is a multiplication of an image of the pattern projected onto the object with the pattern itself.

This may be provided in the following way. In a further embodiment of the invention the pattern generation means comprises a transparent pattern element with an opaque mask. The probe light is transmitted through the pattern element, preferably transmitted transversely through the pattern element. The light returned from the object being scanned is retransmitted the opposite way through said pattern element and imaged onto the camera. This is preferably done in a way where the image of the pattern illuminating the object and the image of the pattern itself are coinciding when both are imaged onto the camera. One particular example of a pattern is a rotating wheel with an opaque mask comprising a plurality of radial spokes arranged in a symmetrical order such that the pattern possesses rotational periodicity. In this embodiment there is a well-defined pattern oscillation period if the pattern is substantially rotated at a constant speed. We define the oscillation period as $2\pi/\omega$.

We note that in the described embodiment of the invention the illumination pattern is a pattern of light and darkness. A light sensing element in the camera with a signal proportional to the integrated light intensity during the camera integration time $\delta t$ with label j, $I_j$ is given by $$I_j = K \int_t^{t+\delta t} T_j(t')S_j(t')dt'$$

Here K is the proportionality constant of the sensor signal, t is the start of the camera integration time, $T_j$ is the time-varying transmission of the part of the rotating pattern element imaged onto the j'th light sensing element, and $S_j$ is the time-varying light intensity of light returned from the scanned object and imaged onto the j'th light sensing element. In the described embodiment $T_j$ is the step function substantially defined by $T(t)=0$ for $\sin(\omega t+\phi_j)>0$ and $T_j(t)=1$ elsewhere. $\phi_j$ is a phase dependent on the position of the j'th imaging sensor.

The signal on the light sensing element is a correlation measure of the pattern and the light returned from the object being scanned. The time-varying transmission takes the role of the reference signal and the time-varying light intensity of light returned from the scanned object takes the role of the input signal. The advantage of this embodiment of the invention is that a normal CCD or CMOS camera with intensity sensing elements may be used to record the correlation measure directly since this appears as an intensity on the sensing elements. Another way of expressing this is that the computation of the correlation measure takes place in the analog, optical domain instead of in an electronic domain such as an FPGA or a PC.

The focus position corresponding to the pattern being in focus on the object being scanned for a single sensor element in the camera will then be given by the maximum value of the correlation measure recorded with that sensor element when the focus position is varied over a range of values. The focus position may be varied in equal steps from one end of the scanning region to the other. One embodiment of the invention comprises means for recording and/or integrating and/or monitoring and/or storing each of a plurality of the sensor elements over a range of focus plane positions.

Preferably, the global maximum should be found. However, artifacts such as dirt on the optical system can result in false global maxima. Therefore, it can be advisable to look for local maxima in some cases.

Since the reference signal does not average to zero the correlation measure has a DC component. Since the DC part is not removed, there may exist a trend in DC signal over all focus element positions, and this trend can be dominating numerically. In this situation, the focus position may still be found by analysis of the correlation measure and/or one or more of its derivatives.

In a further embodiment of the invention the camera integration time is an integer number M of the pattern oscillation period, i.e. $\delta t = 2\pi M/\omega$. One advantage of this embodiment is that the magnitude of the correlation measure can be measured with a better signal-to-noise ratio in the presence of noise than if the camera integration time is not an integer number of the pattern oscillation period.

In another further embodiment of the invention the camera integration time is much longer than pattern oscillation period, i.e. $\delta t >> 2\pi M/\omega$. Many times the pattern oscillation time would here mean e.g. camera integration time at least 10 times the oscillation time or more preferably such as at least 100 or 1000 times the oscillation time. One advantage of this embodiment is that there is no need for synchronization of camera integration time and pattern oscillation time since for very long camera integration times compared to the pattern oscillation time the recorded correlation measure is substantially independent of accurate synchronization.

Equivalent to the temporal correlation principle the optical correlation principle may be applied in general within image analysis. Thus, a further embodiment of the invention relates to a method for calculating the amplitude of a light intensity oscillation in at least one (photoelectric) light sensitive element, said light intensity oscillation generated by a superposition of a varying illumination pattern with itself, and said amplitude calculated by time integrating the signal from said at least one light sensitive element over a plurality of pattern oscillation periods.

Spatial Correlation

The above mentioned correlation principles (temporal correlation and optical correlation) require the pattern to be varying in time. If the optical system and camera provides a lateral resolution which is at least two times what is needed for the scan of the object then it is possible to scan with a static pattern, i.e. a pattern which is not changing in time. This principle is termed "spatial correlation". The correlation measure is thus at least computed with sensor signals recorded at different sensor sites.

The lateral resolution of an optical system is to be understood as the ability of optical elements in the optical system, e.g. a lens system, to image spatial frequencies on the object being scanned up to a certain point. Modulation transfer curves of the optical system are typically used to describe imaging of spatial frequencies in an optical system. One could e.g. define the resolution of the optical system as the spatial frequency on the object being scanned where the modulation transfer curve has decreased to e.g. 50%. The resolution of the camera is a combined effect of the spacing of the individual camera sensor elements and the resolution of the optical system.

In the spatial correlation the correlation measure refers to a correlation between input signal and reference signal occurring in space rather than in time. Thus, in one embodiment of the invention the resolution of the measured 3D geometry is equal to the resolution of the camera. However, for the spatial correlation the resolution of the measured 3D geometry is lower than the resolution of the camera, such as at least 2 times lower, such as at least 3 times lower, such as at least 4 times lower, such as at least 5 times lower, such as at least 10 times lower. The sensor element array is preferably divided into groups of sensor elements, preferably rectangular groups, such as square groups of sensor elements, preferably adjacent sensor elements. The resolution of the scan, i.e. the measured 3D geometry, will then be determined by the size of these groups of sensor elements. The oscillation in the light signal is provided within these groups of sensor elements, and the amplitude of the light oscillation may then be obtained by analyzing the groups of sensor elements. The division of the sensor element array into groups is preferably provided in the data processing stage, i.e. the division is not a physical division thereby possibly requiring a specially adapted sensor array. Thus, the division into groups is "virtual" even though the single pixel in a group is an actual physical pixel.

In one embodiment of the invention the pattern possesses translational periodicity along at least one spatial coordinate. In a further embodiment of the invention the spatially periodic pattern is aligned with the rows and/or the columns of the array of sensor elements. For example in the case of a static line pattern the rows or columns of the pixels in the camera may be parallel with the lines of the pattern. Or in the case of a static checkerboard pattern the row and columns of the checkerboard may be aligned with the rows and columns, respectively, of the pixels in the camera. By aligning is meant that the image of the pattern onto the camera is aligned with the "pattern" of the sensor element in the sensor array of the camera. Thus, a certain physical location and orientation of the pattern generation means and the camera requires a certain configuration of the optical components of the scanner for the pattern to be aligned with sensor array of the camera.

In a further embodiment of the invention at least one spatial period of the pattern corresponds to a group of sensor elements. In a further embodiment of the invention all groups of sensor elements contain the same number of elements and have the same shape. E.g. when the period of a checkerboard pattern corresponds to a square group of e.g. 2×2, 3×3, 4×4, 5×5, 6×6, 7×7, 8×8, 9×9, 10×10 or more pixels on the camera.

In yet another embodiment one or more edges of the pattern is aligned with and/or coincide with one or more edges of the array of sensor elements. For example a checkerboard pattern may be aligned with the camera pixels in such a way that the edges of the image of the checkerboard pattern onto the camera coincide with the edges of the pixels.

In spatial correlation independent knowledge of the pattern configuration allows for calculating the correlation measure at each group of light sensing. For a spatially periodic illumination this correlation measure can be computed without having to estimate the cosine and sinusoidal part of the light intensity oscillation. The knowledge of the pattern configuration may be obtained prior to the 3D scanning.

In a further embodiment of the invention the correlation measure, $A_j$, within a group of sensor elements with label j is determined by means of the following formula:

$$A_j = \sum_{i=1}^{n} f_{i,j} I_{i,j}$$

Where n is the number of sensor elements in a group of sensors, $f_j = (f_{1,j}, \ldots f_{n,j})$ is the reference signal vector obtained from knowledge of the reference signal vector obtained from knowledge of the pattern configuration, an $I_j = (I_{1,j}, \ldots I_{n,j})$ is input signal vector. For the case of sensors grouped in square regions with N sensors as square length then $n = N^2$.

Preferably, but not necessarily, the elements of the reference signal vector averages to zero over space, i.e. for all j we have $$\sum_{i=1}^{n} f_{i,j} = 0$$

to suppress the DC part of the correlation measure. The focus position corresponding to the pattern being in focus on the object for a single group of sensor elements in the camera will be given by an extremum value of the correlation measure of that sensor element group when the focus position is varied over a range of values. The focus position may be varied in equal steps from one end of the scanning region to the other.

In the case of a static checkerboard pattern with edges aligned with the camera pixels and with the pixel groups having an even number of pixels such as 2×2, 4×4, 6×6, 8×8, 10×10, a natural choice of the reference vector $f$ would be for its elements to assume the value 1 for the pixels that image a bright square of the checkerboard and −1 for the pixels that image a dark square of the checkerboard.

Equivalent to the other correlation principles the spatial correlation principle may be applied in general within image analysis. In particular in a situation where the resolution of the camera is higher than what is necessary in the final image. Thus, a further embodiment of the invention relates to a method for calculating the amplitude(s) of a light intensity oscillation in at least one group of light sensitive elements, said light intensity oscillation generated by a spatially varying static illumination pattern, said method comprising the steps of:
  providing the signal from each light sensitive element in said group of light sensitive elements, and
  calculating said amplitude(s) by integrating the products of a predetermined function and the signal from the corresponding light sensitive element over said group of light sensitive elements, wherein said predetermined function is a function reflecting the illumination pattern.

To generalize the principle to a plurality of light sensitive elements, for example in a sensor array, the correlation measure or amplitude of the light oscillation in group j may be expressed as $$A_j = \sum_{i=1}^{n} f(i, j) I_{i,j},$$

where n is the number of sensor elements in group j, $l_{i,j}$ is the signal from the 7th sensor element in group j and $f(i,j)$ is a predetermined function reflecting the pattern.

Compared to temporal correlation, spatial correlation has the advantage that no moving pattern is required. This implies that knowledge of the pattern configuration may be obtained prior to the 3D scanning. Conversely, the advantage of temporal correlation is its higher resolution, as no pixel grouping is required.

All correlation principles, when embodied with an image sensor that allows very high frame rates, enable 3D scanning of objects in motion with little motion blur. It also becomes possible to trace moving objects over time ("4D scanning"), with useful applications for example in machine vision and dynamic deformation measurement. Very high frame rates in this context are at least 500, but preferably at least 2000 frames per second.

Transforming correlation measure extrema to 3D world coordinates Relating identified focus position(s) for camera sensor or camera sensor groups to 3D world coordinates may be done by ray tracing through the optical system. Before such ray tracing can be performed the parameters of the optical system need to be known. One embodiment of the invention comprises a calibration step to obtain such knowledge. A further embodiment of the invention comprises a calibration step in which images of an object of known geometry are recorded for a plurality of focus positions. Such an object may be a planar checkerboard pattern. Then, the scanner can be calibrated by generating simulated ray traced images of the calibration object and then adjusting optical system parameters as to minimize the difference between the simulated and recorded images.

In a further embodiment of the invention the calibration step requires recording of images for a plurality of focus positions for several different calibration objects and/or several different orientations and/or positions of one calibration object.

With knowledge of the parameters of the optical system, one can employ backward ray tracing technique to estimate the 2D→3D mapping. This requires that the scanner's optical system be known, preferably through calibration. The following steps can be performed:
  1. From each pixel of the image (at the image sensor), trace a certain number of rays, starting from the image sensor and through the optical system (backward ray tracing).
  2. From the rays that emit, calculate the focus point, the point where all these rays substantially intersect. This point represents the 3D coordinate of where a 2D pixel will be in focus, i.e., in yield the global maximum of light oscillation amplitude.
  3. Generate a look up table for all the pixels with their corresponding 3D coordinates.

The above steps are repeated for a number of different focus lens positions covering the scanner's operation range.

Specular Reflections

High spatial contrast of the in-focus pattern image on the object is often necessary to obtain a good signal to noise ratio of the correlation measure on the camera. This in turn may be necessary to obtain a good estimation of the focus position corresponding to an extremum in the correlation measure. This sufficient signal to noise ratio for successful scanning is often easily achieved in objects with a diffuse surface and negligible light penetration. For some objects, however, it is difficult to achieve high spatial contrast.

A difficult kind of object, for instance, is an object displaying multiple scattering of the incident light with a light diffusion length large compared to the smallest feature size of the spatial pattern imaged onto the object. A human tooth is an example of such an object. The human ear and ear canal are other examples. In case of intra oral scanning, the scanning should preferably be provided without spraying and/or drying the teeth to reduce the specular reflections and light penetration. Improved spatial contrast can be achieved by preferential imaging of the specular surface reflection from the object on the camera. Thus, one embodiment of the invention comprises means for preferential/selectively imaging of specular reflected light and/or diffusively reflected light. This may be provided if the scanner further comprises means for polarizing the probe light, for example by means of at least one polarizing beam splitter. A polarizing beam splitter may for instance be provided for forming an image of the object in the camera. This may be utilized to extinguish specular reflections, because if the incident light is linearly polarized a specular reflection from the object has the property that it preserves its polarization state The scanner according to the invention may further comprise means for changing the polarization state of the probe light and/or the light reflected from the object. This can be provided by means of a retardation plate, preferably located in the optical path. In one embodiment of the invention the retardation plate is a quarter wave retardation plate. A linearly polarized light wave is transformed into a circularly polarized light wave upon passage of a quarter wave plate with an orientation of 45 degrees of its fast axis to the linear polarization direction. This may be utilized to enhance specular reflections because a specular reflection from the object has the property that it flips the helicity of a circularly polarized light wave, whereas light that is reflected by one or more scattering events becomes depolarized.

The Field of View (Scanning Length)

In one embodiment of the invention the probe light is transmitted towards the object in a direction substantially parallel with the optical axis. However, for the scan head to be entered into a small space such as the oral cavity of a patient it is necessary that the tip of the scan head is sufficiently small. At the same time the light out of the scan head need to leave the scan head in a direction different from the optical axis. Thus, a further embodiment of the invention comprises means for directing the probe light and/or imaging an object in a direction different from the optical axis. This may be provided by means of at least one folding element, preferably located along the optical axis, for directing the probe light and/or imaging an object in a direction different from the optical axis. The folding element could be a light reflecting element such as a mirror or a prism. In one embodiment of the invention a 45 degree mirror is used as folding optics to direct the light path onto the object. Thereby the probe light is guided in a direction perpendicular to the optical axis. In this embodiment the height of the scan tip is at least as large as the scan length and preferably of approximately equal size.

One embodiment of the invention comprises at least two light sources, such as light sources with different wavelengths and/or different polarization. Preferably also control means for controlling said at least two light sources. Preferably this embodiment comprises means for combining and/or merging light from said at least two light sources. Preferably also means for separating light from said at least two light sources. If waveguide light sources are used they may be merged by waveguides. However, one or more diffusers may also be provided to merge light sources.

Separation and/or merging may be provided by at least one optical device which is partially light transmitting and partially light reflecting, said optical device preferably located along the optical axis, an optical device such as a coated mirror or coated plate. One embodiment comprises at least two of said optical devices, said optical devices preferably displaced along the optical axis. Preferably at least one of said optical devices transmits light at certain wavelengths and/or polarizations and reflects light at other wavelengths and/or polarizations.

One exemplary embodiment of the invention comprises at least a first and a second light source, said light sources having different wavelength and/or polarization, and wherein a first optical device reflects light from said first light source in a direction different from the optical axis and transmits light from said second light source, and a second optical device reflects light from said second light source in a direction different from the optical axis. Preferably said first and second optical devices reflect the probe light in parallel directions, preferably in a direction perpendicular to the optical axis, thereby imaging different parts of the object surface. Said different parts of the object surface may be at least partially overlapping.

Thus, for example light from a first and a second light source emitting light of different wavelengths (and/or polarizations) is merged together using a suitably coated plate that transmits the light from the first light source and reflects the light from the second light source. At the scan tip along the optical axis a first optical device (e.g. a suitably coated plate, dichroic filter) reflects the light from the first light source onto the object and transmits the light from the second light source to a second optical device (e.g. a mirror) at the end of the scan tip, i.e. further down the optical axis. During scanning the focus position is moved such that the light from the first light source is used to project an image of the pattern to a position below the first optical device while second light source is switched off. The 3D surface of the object in the region below the first optical device is recorded. Then the first light source is switched off and the second light source is switched on and the focus position is moved such that the light from the second light source is used to project an image of the pattern to a position below the second optical device. The 3D surface of the object in the region below the second optical device is recorded. The region covered with the light from the two light sources respectively may partially overlap.

In another embodiment of the invention the probe light is directed in a direction different from the optical axis by means of a curved fold mirror. This embodiment may comprise one or more optical elements, such as lenses, with surfaces that may be aspherical to provide corrected optical imaging.

A further embodiment of the invention comprises of at least one translation stage for translating mirror(s) along the optical axis. This allows for a scan tip with a smaller height than the scan length. A large scan length can be achieved by combining several scans with the mirror(s) in different positions along the optical axis.

In another embodiment of the invention the probe light is directed in a direction different from the optical axis by means of at least one grating that provides anamorphic magnification so that the image of the pattern on the object being scanned is stretched. The grating may be blazed. In this embodiment the light source needs to be monochromatic or semi-monochromatic.

The abovementioned embodiments suitable for increasing the scan length may comprise control means for providing a coordination of the light sources and the focus element.

Color Scanning

One embodiment of the invention is only registering the surface topology (geometry) of the object being scanned. However, another embodiment of the invention is being adapted to obtain the color of the surface being scanned, i.e. capable of registering the color of the individual surface elements of the object being scanned together with the surface topology of the object being scanned. To obtain color information the light source needs to be white or to comprise at least three monochromatic light sources with colors distributed across the visible part of the electromagnetic spectrum.

To provide color information the array of sensor elements may be a color image sensor. The image sensor may accommodate a Bayer color filter scheme. However, other color image sensor types may be provided, such as a Foveon type color image sensor, wherein the image sensor provides color registration in each sensor element.

One embodiment of the invention comprises means selecting one color of the probe light at a time, i.e. selectively switching between different colors of the probe light, thereby illuminating the object with different colors. If a white light source is used then some kind of color filtering must be provided. Preferably comprising a plurality of color filters, such as red, green and blue color filters, and means for inserting said color filters singly in front of the white light source, thereby selecting a color of the probe light.

In one embodiment of the invention color filters are integrated in the pattern generation means, i.e. the pattern generation means comprises color filters, such as translucent and/or transparent parts that are substantially monochromatically colored. For example a pattern element such as a rotating wheel with an opaque mask and where the translucent/transparent parts are color filters. For example one third of the wheel is red, one third is green and one third is blue.

Probe light of different colors may also be provided by at least three monochromatic light sources, such as lasers or LED's, said light sources having wavelengths distributed across the visible part of the wavelength spectrum. This will in general also require means for merging said light sources. For example suitable coated plates. In the case of waveguide light sources, the merging may be provided by a waveguide element.

To handle the different colors of the probe light the optical system is preferably substantially achromatic.

One embodiment of the invention comprises means for switching between at least two colors, preferably three colors, such as red, green and blue, of the probe light for a focal plane position. I.e. for a single focal plane position it is possible to switch between different colors of the probe light. For example by switching on and off different monochromatic light sources (having one only light source turned on at a time) or by applying different color filters. Furthermore, the amplitude of the light signal of each of a plurality of the sensor elements may be determined for each color for each focal plane positions. I.e. for each focus position the color of the probe light may be switched. The embedded time varying pattern provides a single color oscillating light signal and the amplitude of the signal in each sensor element may be determined for that color. Switching to the next color the amplitude may be determined again. When the amplitude has been determined for all colors the focus position is changed and the process is repeated. The color of the surface being scanned may then be obtained by combining and/or weighing the color information from a plurality of the sensor elements. E.g. the color expressed as e.g. an RGB color coordinate of each surface element can be reconstructed by appropriate weighting of the amplitude signal for each color corresponding to the maximum amplitude. This technique may also be applied when a static pattern is provided where the color of at least a part of the pattern is varying in time.

To decrease the amount of data to be processed the color resolution of the imaging may be chosen to be less than the spatial resolution. The color information is then provided by data interpolation. Thus, in one embodiment of the invention the amplitude of the light signal of each of a plurality of the sensor elements is determined for each color for selected full color focal plane positions, and the amplitude of the light signal of each of a plurality of the sensor elements is determined for one color for each focal plane position. Then the color of the surface being scanned may be obtained by interpolating the color information from full color focal plane positions. Thus, for example the amplitude is registered for all colors at an interval of N focus positions; while one color is selected for determination of the amplitude at all focus positions. N is a number which could be e.g. 3, 5, or 10. This results in a color resolution which is less than the resolution of the surface topology. This technique may also be applied when a static pattern is provided where the color of at least a part of the pattern is varying in time.

Another embodiment of the invention does not register full color information and employs only two light sources with different colors. An example of this is a dental scanner that uses red and blue light to distinguish hard (tooth) tissue from soft (gum) tissue.

Impression Scanning

One embodiment of the invention is adapted to impression scanning, such as scanning of dental impressions and/or ear canal impressions.

Small Cavity Scanner

Specific applications of the scanner according to the invention relates to scanning of cavities, in particular body cavities. Scanning in cavities may relate to scanning of objects in the cavity, such as scanning of teeth in a mouth. However, scanning of e.g. the ear relate to scanning of the inner surface of the cavity itself. In general scanning of a cavity, especially a small cavity, requires some kind of probe for the scanner. Thus, in one embodiment of the invention the point of emission of probe light and the point of accumulation of reflected light is located on a probe, said probe being adapted to be entered into a cavity, such as a body cavity.

In another embodiment of the invention the probe is adapted to scan at least a part of the surface of a cavity, such as an ear canal. The ability to scan at least a part of the external part of the ear and/or the ear canal and make a virtual or real model of the ear is essential in the design of modern custom-fitted hearing aid (e.g. ear shell or mold). Today, scanning of ears is performed in a two-step process where a silicone impression of the ear is taken first and the impression is subsequently scanned using an external scanner in a second step.

Thus, one embodiment of the invention comprises
 a housing accommodating the camera, pattern generation means, focus varying means and data processing means, and
 at least one probe accommodating a first optical system, preferably a substantially elongated probe.

Preferably, the point of emission of probe light and the point of accumulation of light returned from the scanned object is located on said probe. The optical system in the probe is for transmitting the probe light from the housing toward the object and also for transmitting and/or imaging light returned from the object back towards the housing where the camera is located. Thus, the optical system in the probe may comprise a system of lenses. In one embodiment of the invention probe may comprise at least one optical fibre and/or a fibre bundle for transmitting/transporting/guiding the probe light and/or the returned light from the object surface. In this case the optical fibre(s) may act as an optical relay system that merely transports light (i.e. probe light and returned light) inside the probe. In one embodiment of the invention the probe is endoscopic. The probe may be rigid or flexible. Use of optical fibre(s) in the probe may e.g. provide a flexible probe with a small diameter.

In one embodiment of the invention the light is transmitted to the object and imaged by means of only the optical system in the probe, the first optical system. However, in a further embodiment of the invention the housing may further comprise a second optical system.

In a further embodiment of the invention the probe is detachable from the housing. Then preferably a first point of emission of probe light and a first point of accumulation of returned light is located on the probe, and a second point of emission of probe light and a second point of accumulation of returned light is located on the housing. This may require optical systems in both the housing and the probe. Thus, a scan may be obtained with the probe attached to the housing. However, a scan may also be obtained with the probe detached from the housing, i.e. the housing may be a standalone scanner in itself. For example the probe may be adapted to be inserted into and scanning the inside of a cavity, whereas the housing may be adapted to scanning of exterior surfaces. The attachment of the probe may include mechanical and/or electrical transfer between the housing and the probe. For instance attaching the probe may provide an electrical signal to the control electronics in the housing that signals the current configuration of the device.

In one embodiment of the invention the probe light is directed toward the object in a direction substantially parallel with the optical axis and/or the longitudinal axis of the probe.

In a further embodiment the probe comprises a posterior reflective element, such as a mirror, for directing the probe light in a direction different from the optical axis, preferably in a direction perpendicular to the optical axis. Applying to the abovementioned example with a stand-alone scanner housing with the probe detached, the probe light may exit the housing in a direction parallel with the optical axis of the optical system in the housing (i.e. the second optical system), whereas with the probe attached the probe light may be directed in a direction different than the optical axis of the optical system of the probe (i.e. the first optical system). Thereby the probe is better adapted to scanning a cavity.

In some embodiments of this invention, waste heat generated in the scanner is used to warm the probe such that no or less condensation occurs on the probe when the probe is inside the body cavity, e.g. the mouth. Waste heat can, e.g., be generated by the processing electronics, the light source, and/or the mechanism that moves the focus element.

In some embodiments of this invention, the scanner provides feedback to the user when the registration of subsequent scans to a larger model of the 3D surface fails. For example, the scanner could flash the light source.

Further, the probe may comprise means for rotating/spinning the reflective element, preferably around an axis substantially parallel with the optical axis and/or the longitudinal axis of the probe. Thereby the probe may be adapted to provide a scan 360° around the optical axis and/or the longitudinal axis of the probe, preferably without rotation of probe and/or scanner.

In a further embodiment of the invention a plurality of different probes matches the housing. Thereby different probes adapted to different environments, surfaces, cavities, etc. may be attached to the housing to account for different scanning situations. A specific example of this is when the scanner comprises a first probe being adapted to scan the interior part of a human ear and a second probe being adapted to scan the exterior part of said human ear. Instead of a second probe it may be the housing itself, i.e. with the probe detached, that is adapted to scan the exterior part of said human ear. I.e. the housing may be adapted to perform a 3D surface scan. In other words: the housing with the probe attached may be adapted to scan the interior part of a human ear and the housing with the probe detached may be adapted to scan the exterior part of said human ear. Preferably, means for merging and/or combining 3D data for the interior and exterior part of the ear provided, thereby providing a full 3D model of a human ear.

For handheld embodiments of this invention, a pistol-like design is ergonomic because the device rests comfortably inside the hand of the operator, with most of the mass resting on top of the hand and/or wrist. In such a design, it is advantageous to be able to orient the above-mentioned posterior reflective in multiple positions. For example, it could be possible to rotate a probe with the posterior reflective element, with or without the step of detaching it from the main body of the scanning device. Detachable probes may also be autoclavable, which is a definitely advantage for scanners applied in humans, e.g., as medical devices. For embodiments of this invention that realize a physically moving focus element by means of a motor, it is advantageous to place this motor inside a grip of the pistol-like shape.

Use of Motion, Gravity, and Magnetic Sensors

Handheld embodiments of the invention preferably include motion sensors such as accelerometers and/or gyros. Preferably, these motion sensors are small like microelectromechanical systems (MEMS) motion sensors. The motion sensors should preferably measure all motion in 3D, i.e., both translations and rotations for the three principal coordinate axes. The benefits are:

A) Motion sensors can detect vibrations and/or shaking. Scans such affected can be either discarded or corrected by use of image stabilization techniques.

B) Motion sensors can help with stitching and/or registering partial scans to each other. This advantage is relevant when the field of view of the scanner is smaller than the object to be scanned. In this situation, the scanner is applied for small regions of the object (one at a time) that then are combined to obtain the full scan. In the ideal case, motion sensors can provide the required relative rigid-motion transformation between partial scans' local coordinates, because they measure the relative position of the scanning device in each partial scan. Motion sensors with limited accuracy can still provide a first guess for a software-based stitching/registration of partial scans based on, e.g., the Iterative Closest Point class of algorithms, resulting in reduced computation time.

C) Motion sensors can be used (also) as a remote control for the software that accompanies the invention. Such software, for example, can be used to visualize the acquired scan. With the scanner device now acting as a remote control, the user can, for example, rotate and/or pan the view (by moving the remote control in the same way as the object on the computer screen should "move"). Especially in clinical application, such dual use of the handheld scanner is preferable out of hygienic considerations, because the operator avoids contamination from alternative, hand-operated input devices (touch screen, mouse, keyboard, etc.).

Even if it is too inaccurate to sense translational motion, a 3-axis accelerometer can provide the direction of gravity relative to the scanning device. Also a magnetometer can provide directional information relative to the scanning device, in this case from the earth's magnetic field. Therefore, such devices can help with stitching/registration and act as a remote control element.

The present invention relates to different aspects including the scanner device described above and in the following, and corresponding methods, devices, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a method for obtaining and/or measuring the 3D geometry of at least a part of the surface of an object, said method comprising the steps of:
generating a probe light incorporating a spatial pattern,
transmitting the probe light towards the object along the optical axis of an optical system, thereby illuminating at least a part of the object with said pattern,
transmitting at least a part of the light returned from the object to the camera,
varying the position of the focus plane of the pattern on the object while maintaining a fixed spatial relation of the scanner and the object,
obtaining at least one image from said array of sensor elements,
evaluating a correlation measure at each focus plane position between at least one image pixel and a weight function, where the weight function is determined based on information of the configuration of the spatial pattern;
determining by analysis of the correlation measure the in-focus position(s) of:
  each of a plurality of image pixels in the camera for said range of focus plane positions, or
  each of a plurality of groups of image pixels in the camera for said range of focus planes, and
transforming in-focus data into 3D real world coordinates.

Disclosed is also a computer program product comprising program code means for causing a data processing system to perform the method, when said program code means are executed on the data processing system.

Disclosed is also a computer program product, comprising a computer-readable medium having stored there on the program code means.

Another aspect of the invention relates to a scanner for obtaining and/or measuring the 3D geometry of at least a part of the surface of an object, said scanner comprising:
at least one camera accommodating an array of sensor elements,
means for generating a probe light,
means for transmitting the probe light towards the object thereby illuminating at least a part of the object,
means for transmitting light returned from the object to the camera,
means for varying the position of the focus plane on the object,
means for obtaining at least one image from said array of sensor elements,
means for:
  a) determining the in-focus position(s) of:
    each of a plurality of the sensor elements for a range of focus plane positions, or
    each of a plurality of groups of the sensor elements for a range of focus plane positions, and
  b) transforming in-focus data into 3D real world coordinates;
wherein the scanner further comprises counter-weight means for counter-balancing the means for varying the position of the focus plane.

Disclosed is also a method for obtaining and/or measuring the 3D geometry of at least a part of the surface of an object, said method comprising the steps of:
accommodating an array of sensor elements,
generating a probe light,
transmitting the probe light towards the object thereby illuminating at least a part of the object,
transmitting light returned from the object to the camera,
varying the position of the focus plane on the object,
obtaining at least one image from said array of sensor elements,
determining the in-focus position(s) of:
  each of a plurality of the sensor elements for a range of focus plane positions, or
  each of a plurality of groups of the sensor elements for a range of focus plane positions, and
transforming in-focus data into 3D real world coordinates;
wherein the method further comprises counter-balancing the means for varying the position of the focus plane.

Another aspect of the invention relates to a handheld 3D scanner with a grip at an angle of more than 30 degrees from the scanner's main optical axis, for use in intraoral or in-ear scanning.

BRIEF DESCRIPTION OF THE DRAWINGS

FIGS. 3A through 3C: Schematic presentations of example embodiments of patterns according to the invention.

FIGS. 10A and 10B: Schematics showing how a scanner embodiment can be used to both scan the outer and inner ear, respectively.

Figure 1:
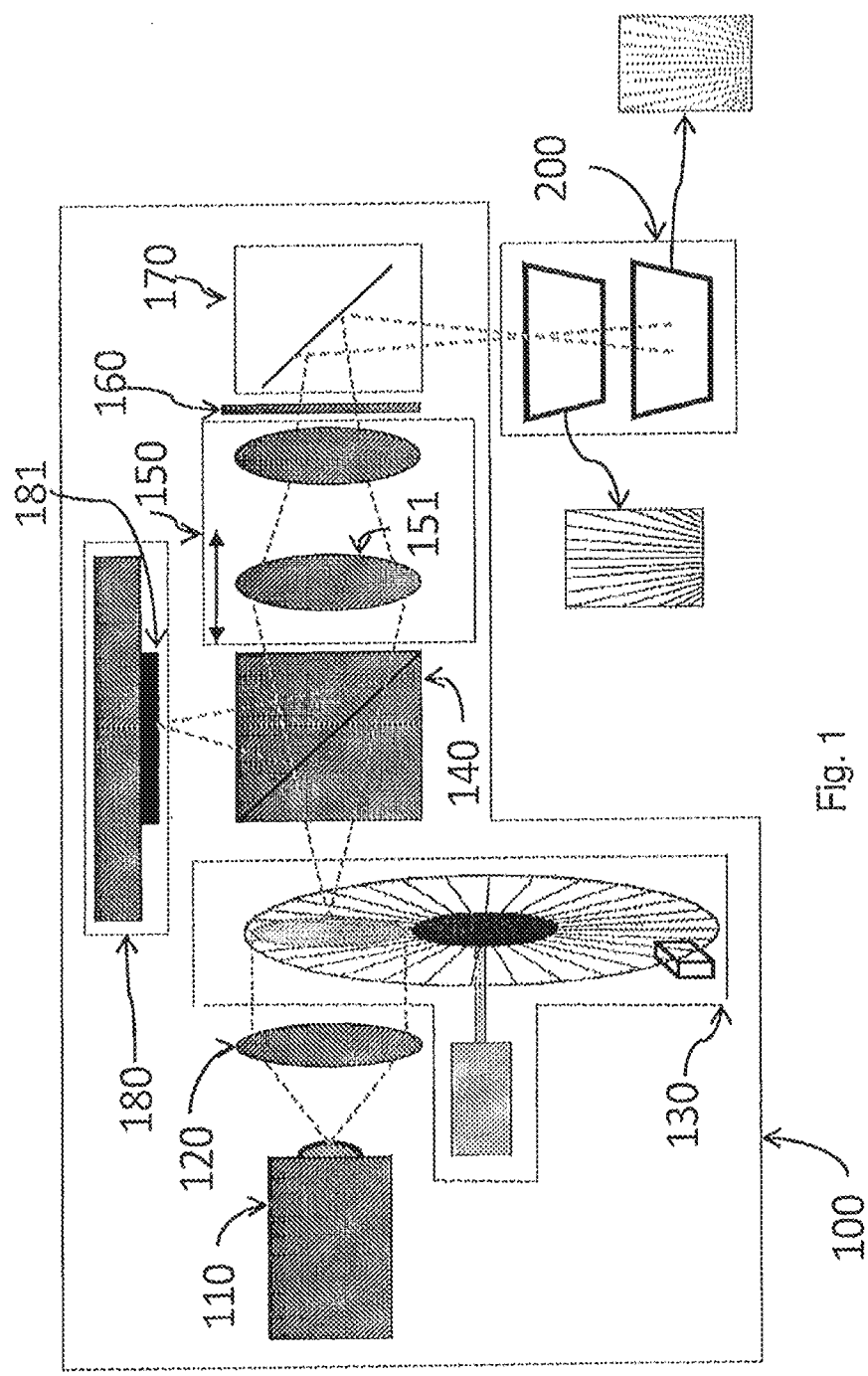
FIG. 1: A schematic presentation of a first example embodiment of the device according to the invention.

It will be understood that the ray traces and lenses depicted in the figures are for purpose of illustration only, and depict optical paths generally in the discussed systems. The ray traces and lens shapes should not be understood to limit the scope of the invention in any sense including the magnitude, direction, or focus of light rays or bundles passing through various optical components, notwithstanding any variations in number, direction, shape, position or size thereof, except as expressly indicated in the following detailed description of the exemplary embodiments illustrated in the drawings.

DETAILED DESCRIPTION OF THE DRAWINGS

A functional hand held 3D surface scanner should preferably have the following properties:

1) Telecentricity in the space of the object being scanned,
2) possibility to shift the focal plane while maintaining telecentricity and magnification
3) simple focusing scheme that involves tuning of optical components only in the handle of the device and not in the probe tip, and
4) a total size consistent with a hand held scanning device.

The scanner embodiment illustrated in FIG. 1 is a handheld scanner with all components inside the housing (head) 100. The scanner head comprises a tip which can be entered into a cavity, a light source 110, optics 120 to collect the light from the light source, pattern generation means 130, a beam splitter 140, an image sensor and electronics 180, a lens system which transmits and images the light between the pattern, the object being scanned, and the image sensor (camera) 180. The light from the light source 110 travels back and forth through the optical system 150. During this passage the optical system images the pattern 130 onto the object being scanned 200 and further images the object being scanned onto the image sensor 181. The lens system includes a focusing element 151 which can be adjusted to shift the focal imaging plane of the pattern on the probed object 200. One way to embody the focusing element is to physically move a single lens element back and forth along the optical axis. The device may include polarization optics 160. The device may include folding optics 170 which directs the light out of the device in a direction different to the optical axis of the lens system, e.g. in a direction perpendicular to the optical axis of the lens system. As a whole, the optical system provides an imaging of the pattern onto the object being probed and from the object being probed to the camera. One application of the device could be for determining the 3D structure of teeth in the oral cavity. Another application could be for determining the 3D shape of the ear canal and the external part of the ear.

The optical axis in FIG. 1 is the axis defined by a straight line through the light source 110, optics 120 and the lenses in the optical system 150. This also corresponds to the longitudinal axis of the scanner illustrated in FIG. 1. The optical path is the path of the light from the light source 110 to the object 220 and back to the camera 180. The optical path may change direction, e.g. by means of beam splitter 140 and folding optics 170.

The focus element is adjusted in such a way that the image of the pattern on the scanned object is shifted along the optical axis, preferably in equal steps from one end of the scanning region to the other. When the pattern is varied in time in a periodic fashion for a fixed focus position then the in-focus regions on the object will display a spatially varying pattern. The out-of-focus regions will display smaller or no contrast in the light variation. The 3D surface structure of the probed object is determined by finding the plane corresponding to an extremum in the correlation measure for each sensor in the camera's sensor array or each group of sensor in the camera's sensor array when recording the correlation measure for a range of different focus positions 300. Preferably one would move the focus position in equal steps from one end of the scanning region to the other.

Pattern Generation

An embodiment of the pattern generation means is shown in FIG. 3A: A transparent wheel with an opaque mask 133 in the form of spokes pointing radially from the wheel center. In this embodiment the pattern is time-varied by rotating the wheel with a motor 131 connected to the wheel with e.g. a drive shaft 132. The position of the pattern in time may be registered during rotation. This can be achieved by e.g. using a position encoder on the rim of the pattern 134 or obtaining the shaft position directly from motor 131.

FIG. 3B illustrates another embodiment of the pattern generation means: A segmented light source 135, preferably a segmented LED. In this embodiment the LED surface is imaged onto the object under investigation. The individual LED segments 136 are turned on and off in a fashion to provide a known time-varying pattern on the object. The control electronics 137 of the time varying pattern is connected to the segmented light source via electrical wires 138. The pattern is thus integrated into the light source and a separate light source is not necessary.

Figure 3C:
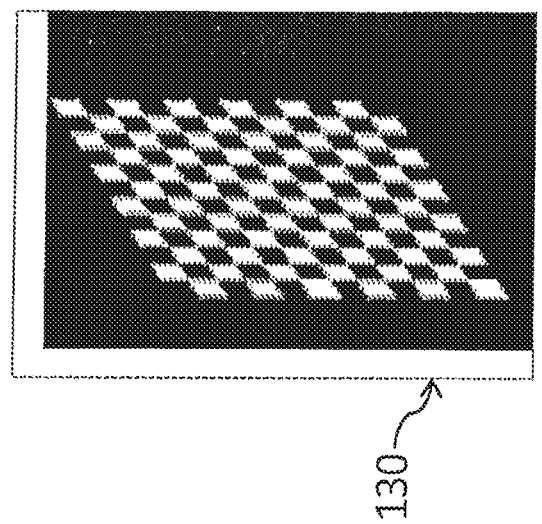

FIG. 3C illustrates a static pattern as applied in a spatial correlation embodiment of this invention. The checkerboard pattern shown is preferred because calculations for this regular pattern are easiest.

Temporal Correlation

FIG. 1 is also an exemplary illustration of the temporal correlation wherein an image of the pattern on and/or in the object is formed on the camera. Each individual light sensing element in the camera sees a variation in the signal level corresponding to the variation of the illumination pattern on the object. The variation is periodic in the exemplary illustration. The light variation for each individual light sensing element will have a constant phase offset relative to the pattern position.

The correlation measure may be obtained by recording n images on the camera during at least one oscillation period. n is an integer number greater than one. The registration of the pattern position for each individual image combined with the phase offset values for each sensing element and the recorded images allows for an efficient extraction of the correlation measure in each individual sensing element in the camera using the following formula, $$A_j = \sum_{i=1}^{n} f_{i,j} I_{i,j}$$

Here $A_j$ is the estimated correlation measure of sensing element j, $1_{1,j}, \ldots 1_{n,j}$ are the n recorded signals from sensing element j, $f_{1,j}, \ldots f_{n,j}$ are the n reference signal values obtained from the knowledge of the pattern configuration for each image recording. $f$ has two indices i,j. The variation of $f$ with the first index is derived from the knowledge of the pattern position during each image recording. The variation of $f$ with the second index is derived from the knowledge of the pattern geometry which may be determined prior to the 3D scanning.

The focus position corresponding to the pattern being in focus on the object for a single sensor in the camera will be given by an extremum in the recorded correlation measure of that sensor when the focus position is varied over a range of values, preferably in equal steps from one end of the scanning region to the other.
Spatial Correlation In an example of the spatial correlation scheme, one image of the object with projected checkerboard pattern is recorded with as high resolution as allowed by the image sensor.

Figure 16:
FIG. 16: Example fused correlation measure image of an intraoral scene.

The scheme in the spatial correlation in is then to analyze groups of pixels in the recorded image and extract the correlation measure in the pattern. An extremum in the obtained correlation measures indicates the in-focus position. For simplicity, one can use a checkerboard pattern with a period corresponding to n=N×N pixels on the sensor and then analyze the correlation measure within one period of the pattern (in the general case the pattern need not be quadratic N×N). In the best case, it will be possible to align the pattern so that the checkerboard edges coincide with the pixel edges but the scanning principle does not rely upon this. FIG. 16 shows this for the case n=4×4=16. For a sensor with W×H=1024×512 pixels, this would correspond to obtaining 256×128 correlation measure points from one image. Extraction of the correlation measure $A_j$ within an N×N group of pixels with label j is given by $$A_j = \sum_{i=1}^{n} f_{i,j} I_{i,j}$$

where $f_j = (f_{1,j}, \ldots f_{n,j})$ is the reference signal vector obtained from knowledge of the pattern configuration, and $I_j = (I_{1,j}, \ldots I_{n,j})$ is input signal vector.

To suppress any DC part in the light we prefer that for all j that $$0 = \sum_{i=1}^{n} f_{i,j}$$

Figure 2:
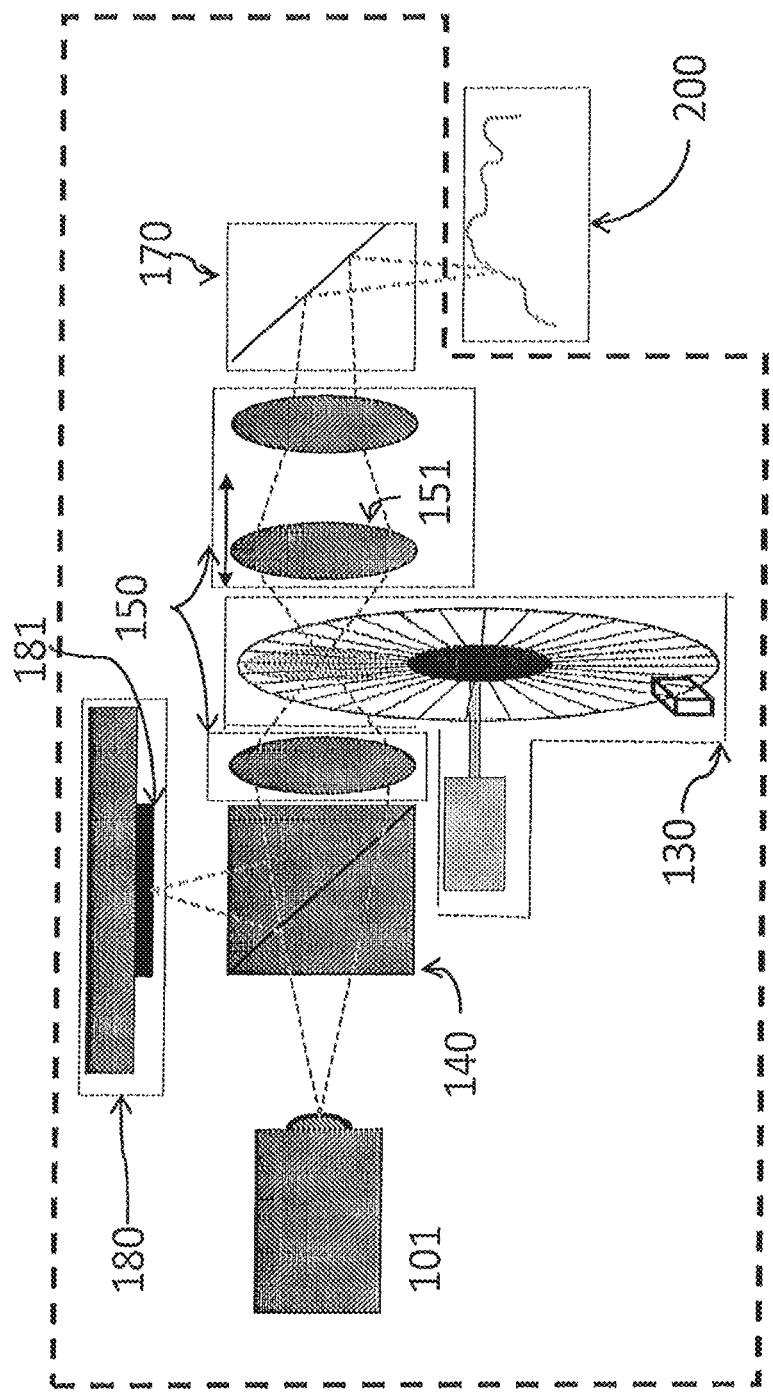
FIG. 2: A schematic presentation of a second example embodiment of the device according to the invention (optical correlation).

For the situation depicted in FIG. 16 for instance, $f_{i,j} = -1$ for the pixels corresponding to the dark parts of the pattern, and $f_{i,j} = +1$ otherwise. If the pattern edge was not aligned with the edges of the pixels, or if the optical system was not perfect (and thus in all practical applications), then $f_{i,j}$ would assume values between $-1$ and $+1$ for some i. A detailed description of how to determine the reference function is given later.
Optical Correlation An example of the optical correlation shown in FIG. 2. In this embodiment an image is formed on the camera 180 which is a superposition of the pattern 130 with the probed object 200. In this embodiment the pattern is of a transmissive nature where light is transmitted through the pattern and the image of the pattern is projected onto the object and back again. In particular this involves retransmission of the light through the pattern in the opposite direction. An image of the pattern onto the camera is then formed with the aid of a beam splitter 140. The result of this arrangement is an image being formed on the camera which is a superposition of the pattern itself and the object being probed. A different way of expressing this is that the image on the camera is substantially a multiplication of an image of the pattern projected onto the object with the pattern itself.

The variation is periodic in the exemplary illustration. The correlation measure between the light variation on the object and the pattern for a given focus distance may be obtained by time integrating the camera signal over a large number of oscillation periods so that exact synchronization of pattern oscillation time and camera integration time is not important. The focus position corresponding to the pattern being in focus on the object for a single sensor in the camera will be given by the maximum recorded signal value of that sensor when the focus position is varied over a range of values, preferably in equal steps from one end of the scanning region to the other.
Finding the Predetermined Reference Function In the following, the process for computing the reference signal $f$ is described for a spatial correlation embodiment of this invention, and depicted in a stylized way in FIGS. 14A-14E.

The process starts by recording a series of images of the checkerboard pattern as projected, e.g., on a flat surface, preferably oriented orthogonally to the optical axis of the scanner. The images are taken at different positions of the focusing element, in effect covering the entire travel range of said focus element. Preferably, the images are taken at equidistant locations.

Figure 14A:
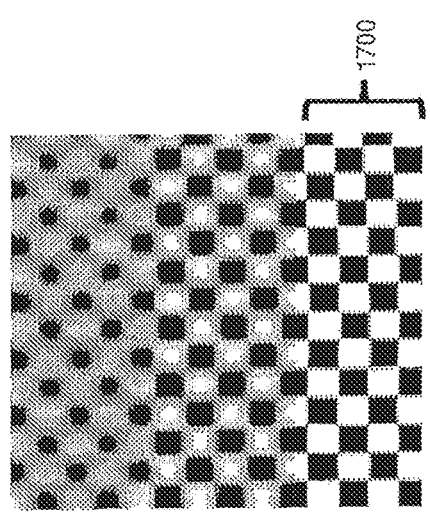
FIGS. 14A through 14E: Illustration of the process of generating a fused reference signal, visualized as images.
Figure 14B:
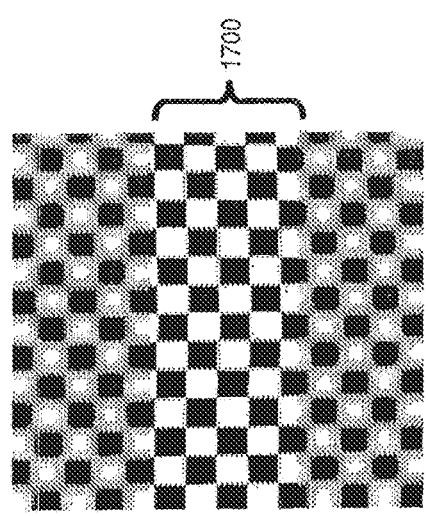
Figure 14C:
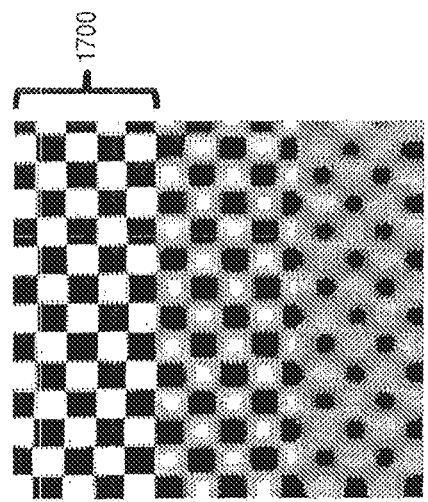
Figure 14D:
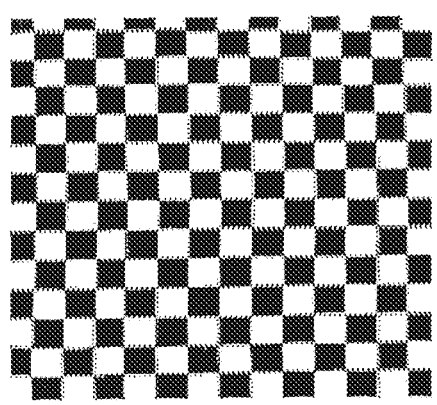

As the focus plane generally is not a geometrical plane, different regions of the flat surface will be in focus in different images. Examples of three such images are shown in FIGS. 14A-14C, where 1700 is an in-focus region. Note that in this stylized figure, transitions between regions in and out of focus, respectively, are exaggerated in order to demonstrate the principle more clearly. Also, in general there will be many more images than just the three used in this simple example.

In-focus regions within an image are found as those of maximum intensity variance (indicating maximum contrast) over the entire said series of images. The region to compute variance over need not be the same as the pixel group dimension used in spatial correlation, but should be large enough to contain the both dark and light regions of the pattern, and it must be the same for all images in the series.

Figure 14E:
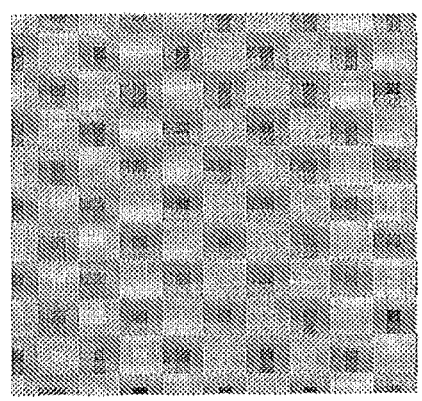

Finally, a "fused image" (FIG. 14D) is generated by combining all the in-focus regions of the series (FIGS. 14A-14C). Note that in real applications, the fused image will generally not be a perfect checkerboard of black and white, but rather include intermediate gray values as caused by an imperfect optical system and a checkerboard that is not perfectly aligned with the camera sensors. An example of part of a real fused image is shown in FIG. 14E.

The pixel intensities within this image can be interpreted as a "weight image" with same dimensions as the original image of the pattern. In other words, the pixel values can be interpreted as the reference signal and the reference vector/set of weight values $f_j = (f_{1,j}, \ldots f_{n,j})$ for the n pixels in the pixel group with index j can be found from the pixel values.

For convenience in the implementation of the calculations, especially when carried out on an FPGA, the fused image can be sub-divided into pixel groups. The DC part of the signal can then be removed by subtracting the within-group intensity mean from each pixel intensity value. Furthermore, one can then normalize by dividing by the within-group standard deviation. The thus processed weight values are an alternative description of the reference signal.

Because of the periodic nature of the "fused image" and thus the "weight image", the latter can be compressed efficiently, thus minimizing memory requirements in the electronics that can implement the algorithm described here. For example, the PNG algorithm can be used for compression.

The "Correlation Image"

A "correlation" image is generated based on the "fused image" and the set of images recorded with the camera during a scan. For spatial correlation based on an N×N checkerboard pattern, recall that within-group correlation measure is $$A_j = \sum_{i=1}^{N \times N} f_{i,j} I_{i,j},$$

where $f_j=(f_{1,j}, \ldots f_{n,j})$ are values from the fused image, and $I_j=(I_{1,j}, \ldots I_{n,j})$ are values from a recorded image on the camera. The pixel groupings used in any DC removal and possibly normalization that yielded the fused image are the same as in the above calculation. For each image recorded by the scanner during a sweep of the focusing element, there will thus be an array of (H/N)×(W/N) values of A. This array can be visualized as an image.

Figure 15:
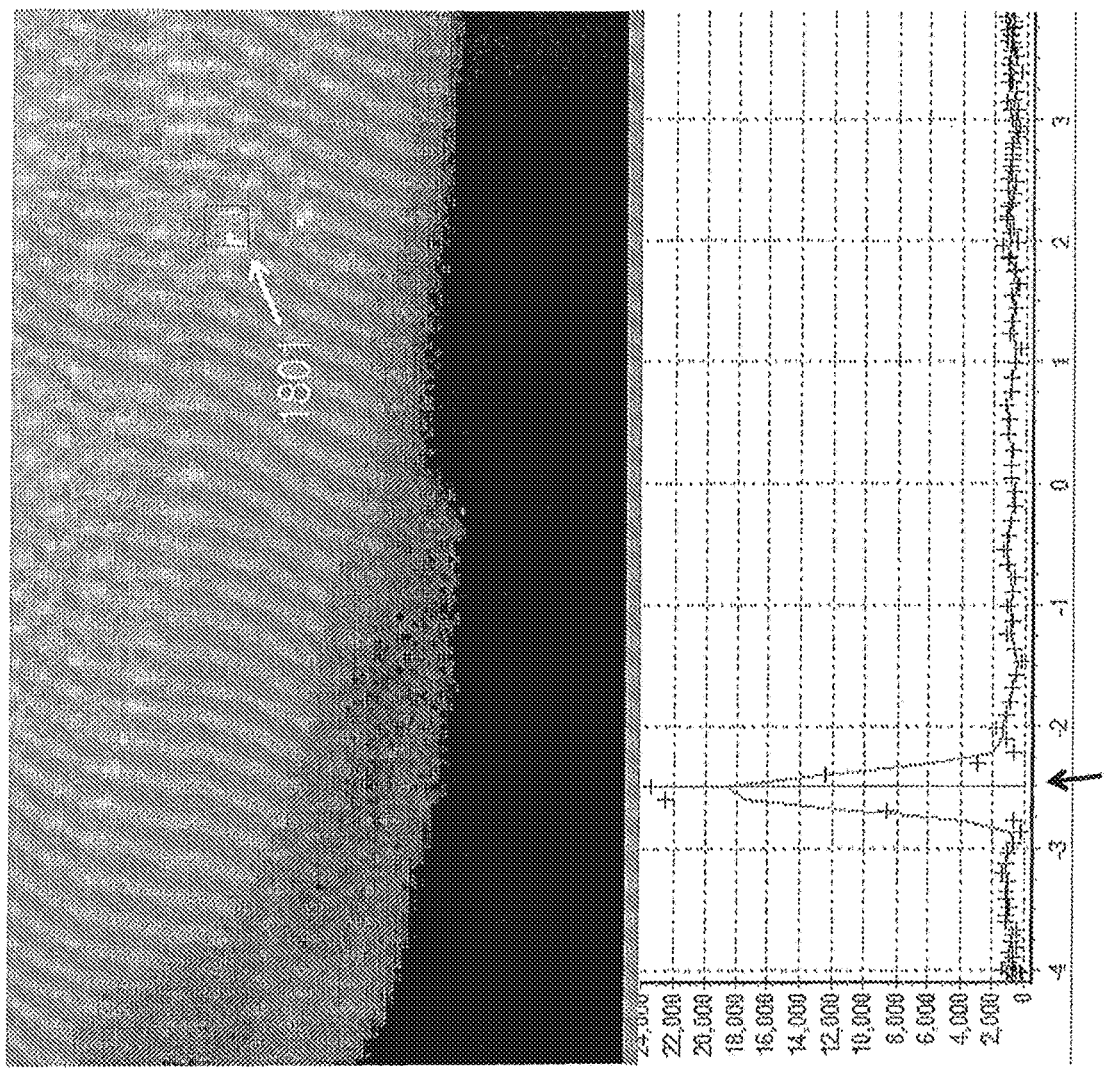
FIG. 15: Top: Example image with projected pattern showing on a human tooth. Bottom: The correlation measure for the series of focus lens positions at the group of pixels framed in the top part of the figure.

FIG. 15 (top section) shows one example correlation measure image, here of part of a human tooth and its edge. A pixel group of 6×6 pixels is marked by a square 1801. For this example pixel group, the series of correlation measures A over all images within a sweep of the focusing element is shown in the chart in the bottom section of FIG. 15 (cross hairs). The x-axis on the chart is the position of the focusing element, while the y-axis shows the magnitude of A. Running a simple Gaussian filter over the raw series results in a smoothed series (solid line). In the figure the focus element is in the position that gives optimal focus for the example group of pixels. This fact is both subjectively visible in the picture, but also determined quantitatively as the maximum of the series of A. The vertical line 1802 in the bottom section of FIG. 15 indicates the location of the global extremum and thus the in-focus position. Note that in this example, the location of the maxima in the smoothed and the raw series, respectively, are visually indistinguishable. In principle, however, it is possible and also advantageous to find the maximum location from the smoothed series, as that can be between two lens positions and thus provide higher accuracy.

The array of values of A can be computed for every image recorded in a sweep of the focus element. Combining the global extrema (over all images) of A in all pixel groups in the same manner the fused image was combined, one can obtain a pseudo-image of dimension (H/N)×(W/N). This we call the "fused correlation image". An example of a fused correlation image of some teeth and gingiva is shown in FIG. 16. As can be seen, it is useful for visualization purposes.

Increasing Field of View

For the scan head to be entered into a small space such as the oral cavity of a patient it is necessary that the tip of the scan head is sufficiently small. At the same time the light out of the scan head need to leave the scan head in a direction different from the optical axis, e.g. at a direction perpendicular to the optical axis. In one embodiment of the invention a 45 degree mirror is used as folding optics 170 direct the light path onto the object. In this embodiment the height of the scan tip need to be at least as large as the scan length.

Figure 4:
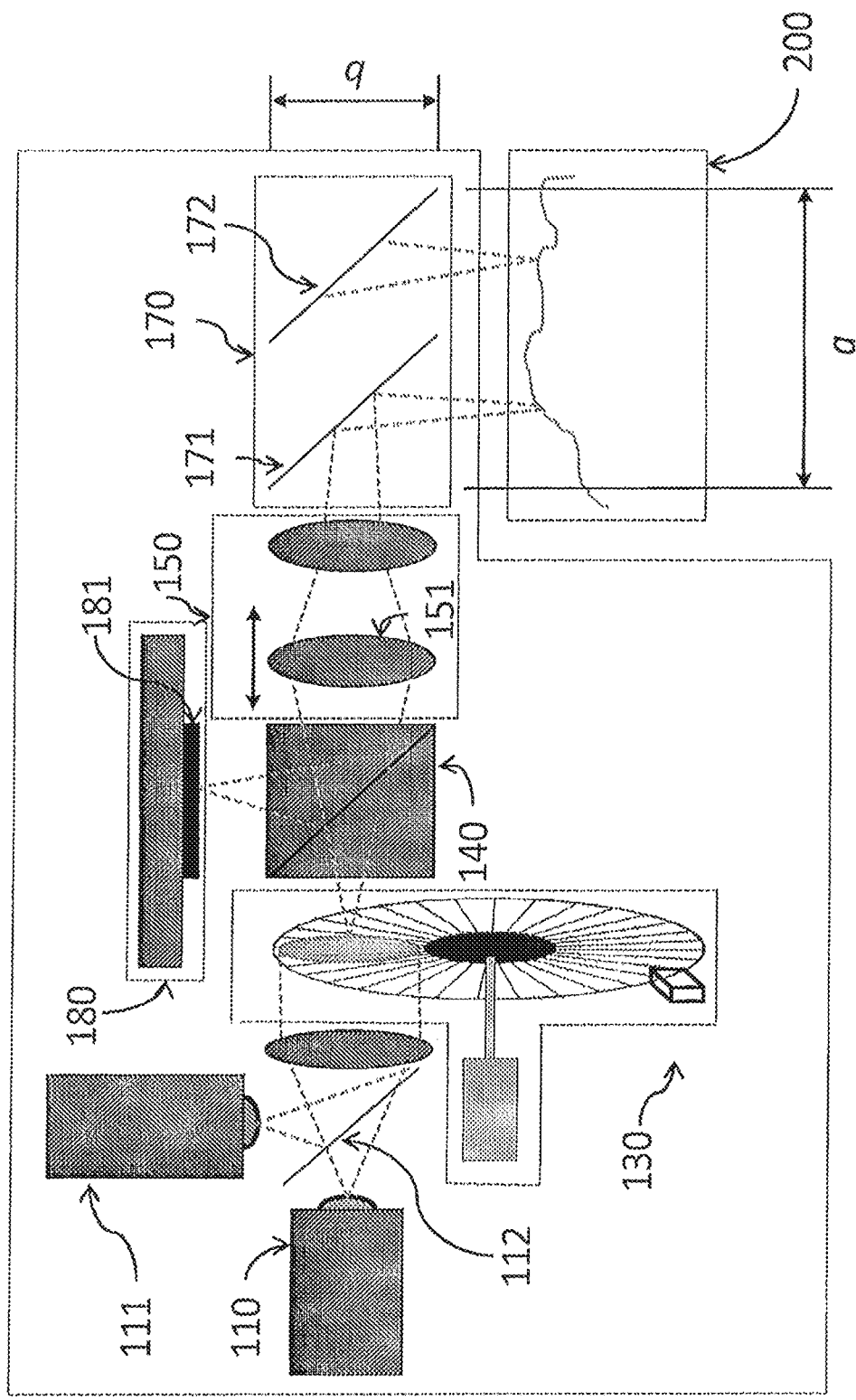
FIG. 4: A schematic presentation of a first example embodiment of a flat scan tip with large scan length, using a plurality of (dichroic) mirrors and light sources.

Another embodiment of the invention is shown in FIG. 4. This embodiment of the invention allows for a scan tip with a smaller height (denoted b in the figure) than the scan length (denoted a in the figure). The light from two sources 110 and 111 emitting light of different colors/wavelengths is merged together using a suitably coated plate (e.g. a dichroic filter) 112 that transmit the light from 110 and reflects the light from 111. At the scan tip a suitably coated plate (e.g. a dichroic filter) 171 reflects the light from one source onto the object and transmits the light from the other source to a mirror at the end of the scan tip 172. During scanning the focus position is moved such that the light from 110 is used to project an image of the pattern to a position below 171 while 111 is switched off. The 3D surface of the object in the region below 171 is recorded. Then 110 is switched off and 111 is switched on and the focus position is moved such that the light from 111 is used to project an image of the pattern to a position below 172. The 3D surface of the object in the region below 172 is recorded. The region covered with the light from 110 and 111 respectively may partially overlap.

Figure 5:
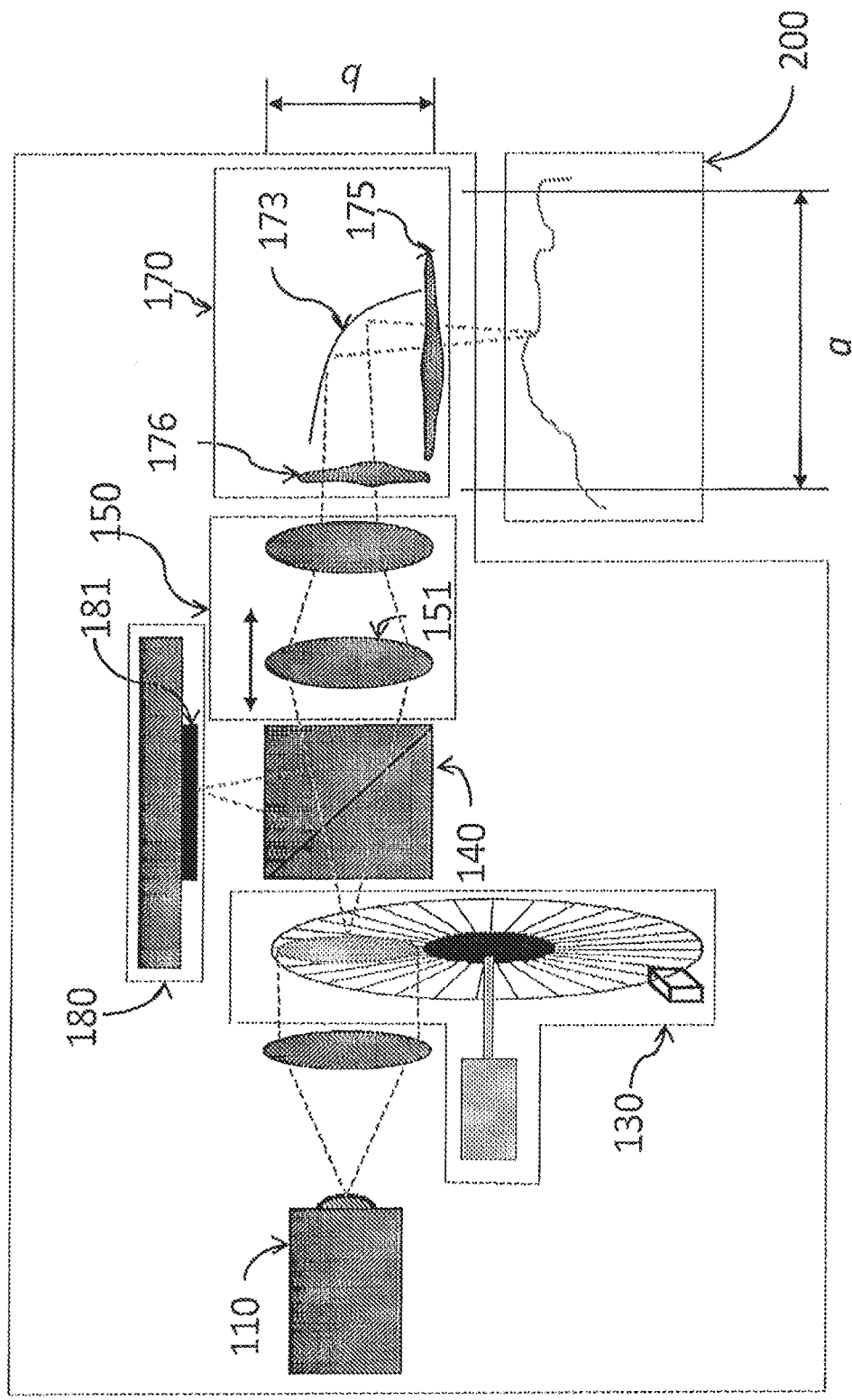
FIG. 5: A schematic presentation of a third example embodiment of a flat scan tip with a large scan length, using a curved mirror.

Another embodiment of the invention that allows for a scan tip with a smaller height (denoted b in the figure) than the scan length (denoted a in the figure) is shown in FIG. 5. In this embodiment the fold optics 170 comprises a curved fold mirror 173 that may be supplemented with one or two lens elements 175 and 176 with surfaces that may be aspherical to provide corrected optical imaging.

Figure 6:
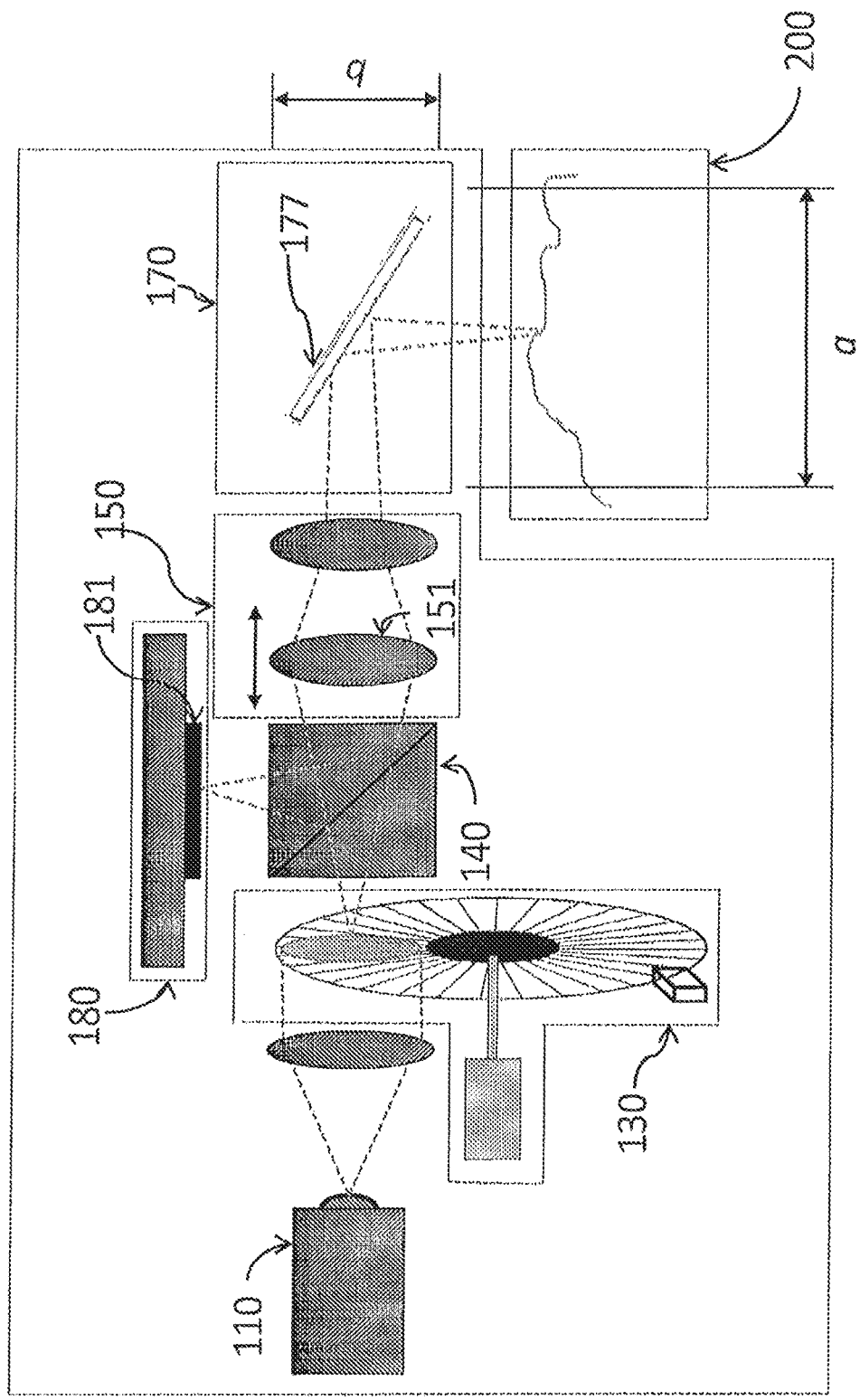
FIG. 6: A schematic presentation of a fourth example embodiment of a flat scan tip with large scan length, using a diffractive grating.

Another embodiment of the invention that allows for a scan tip with a smaller height (denoted b in the figure) than the scan length (denoted a in the figure) is shown in FIG. 6. In this embodiment the fold optics 170 comprises a grating 177 that provides anamorphic magnification so that the image of the pattern on the object being scanned is stretched. The grating may be blazed. The light source 110 needs to be monochromatic or semi-monochromatic in this embodiment.

Achieving high spatial contrast of pattern projected onto difficult objects High spatial contrast of the in-focus pattern image on the object is necessary to obtain a high correlation measure signal based on the camera pictures. This in turn is necessary to obtain a good estimation of the focus position corresponding to the position of an extremum of the correlation measure. This necessary condition for successful scanning is easily achieved in objects with a diffuse surface and negligible light penetration. For some objects, however, it is difficult to achieve high spatial contrast, or more generally variation.

A difficult kind of object, for instance, is an object displaying multiple scattering with a light diffusion length large compared to the smallest feature size of the spatial pattern imaged onto the object. A human tooth is an example of such an object. The human ear and ear canal are other examples. Improved spatial variation in such objects can be achieved by preferential imaging of the specular surface reflection from the object on the camera. An embodiment of the invention applies polarization engineering shown in FIG. 1. In this embodiment the beam splitter 140 is a polarizing beam splitter that transmits respectively reflects two orthogonal polarization states, e.g. S- and P-polarization states. The light transmitted through the lens system 150 is thus of a specific polarization state. Before leaving the device the polarization state is changed with a retardation plate 160. A preferred type of retardation plate is a quarter wave retardation plate. A linearly polarized light wave is transformed into a circularly polarized light wave upon passage of a quarter wave plate with an orientation 45 degrees of its fast axis to the linear polarization direction. A specular reflection from the object has the property that it flips the helicity of a circularly polarized light wave. Upon passage of the quarter wave retardation plate by the specularly reflected light the polarization state becomes orthogonal to the state incident on the object. For instance an S-polarization state propagating in the downstream direction toward the object will be returned as a P-polarization state. This implies that the specularly reflected light wave will be directed towards the image sensor 181 in the beam splitter 140. Light that enters into the object and is reflected by one or more scattering events becomes depolarized and one half of this light will be directed towards the image sensor 181 by the beam splitter 140.

Another kind of difficult object is an object with a shiny or metallic-looking surface. This is particularly true for a polished object or an object with a very smooth surface. A piece of jewelry is an example of such an object. Even very smooth and shiny objects, however, do display an amount of diffuse reflection. Improved spatial contrast in such objects can be achieved by preferential imaging of the diffuse surface reflection from the object on the camera. In this embodiment the beam splitter 140 is a polarizing beam splitter that transmits respectively reflects two orthogonal polarization states, e.g. S- and P-polarization states. The light transmitted through the lens system 150 is thus of a specific polarization state. A diffuse reflection from the object has the property that it loses its polarization. This implies that half of the diffusely reflected light wave will be directed towards the image sensor 181 in the beam splitter 140. Light that enters into the object and is reflected by specular polarization preserves its polarization state and thus none of it will be directed towards the image sensor 181 by the beam splitter 140.

Reducing Shaking Caused by Focus Element

Figure 7:
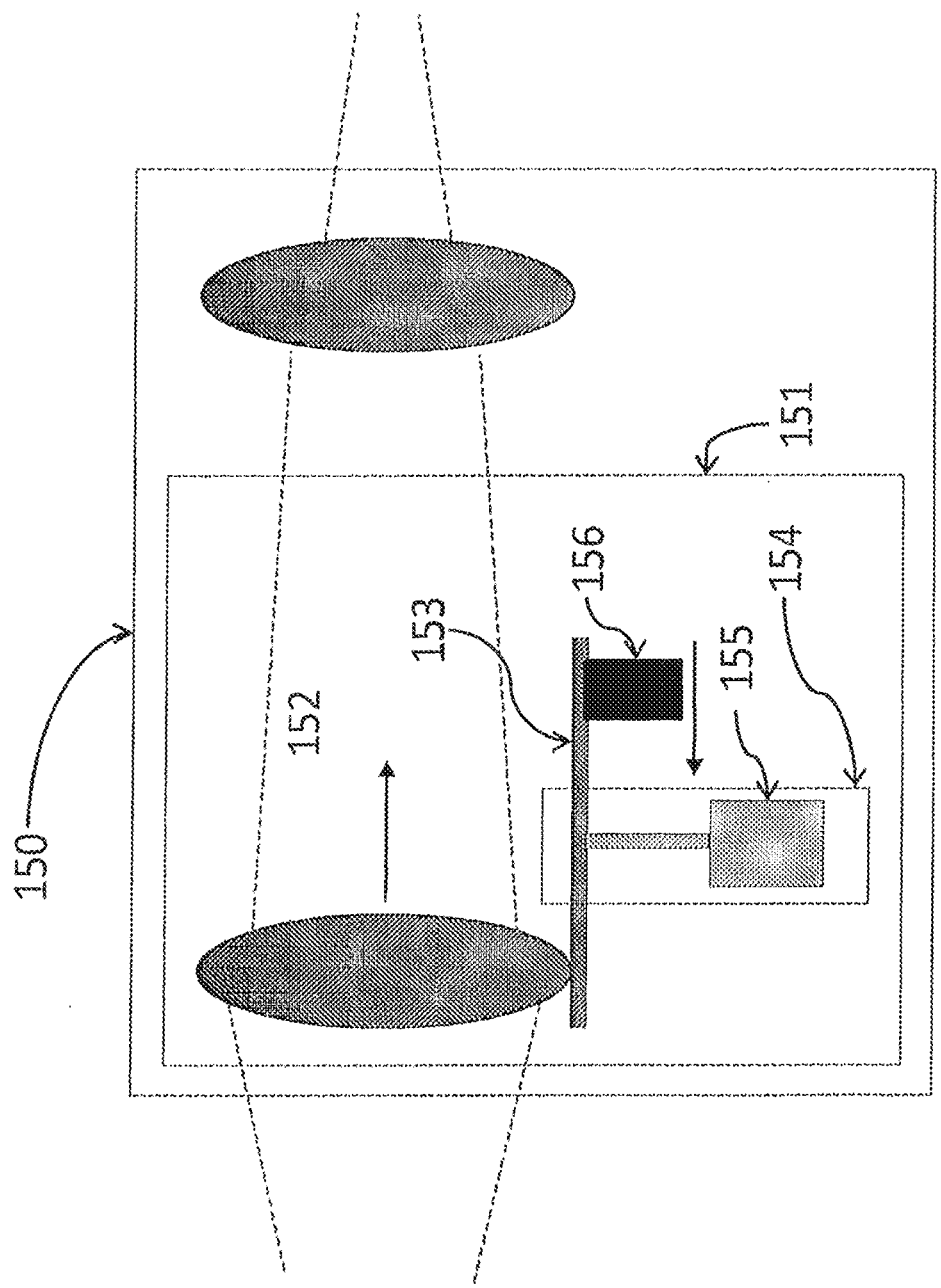
FIG. 7: A schematic presentation of an example embodiment of a mass-balanced focus lens scanner.

During scanning the focus position is changed over a range of values, preferably provided by a focusing element 151 in the optical system 150. FIG. 7 illustrates an example of how to reduce shaking caused by the oscillating focus element. The focusing element is a lens element 152 that is mounted on a translation stage 153 and translated back and forth along the optical axis of said optical system with a mechanical mechanism 154 that includes a motor 155. During scanning the center of mass of the handheld device is shifted due to the physical movement of the lens element and holder. This results in an undesirable shaking of the handheld device during scanning. The situation is aggravated if the scan is fast, e.g. a scan time of less than one second. In one implementation of the invention the shifting of the center of mass is eliminated by moving a counter-weight 156 in a direction opposite to the lens element in such a way that the center of mass of the handheld device remains fixed. In the preferred implementation the focus lens and the counter-weight are mechanically connected and their opposite movement is driven by the same motor.

Color Measurement

Figure 8:
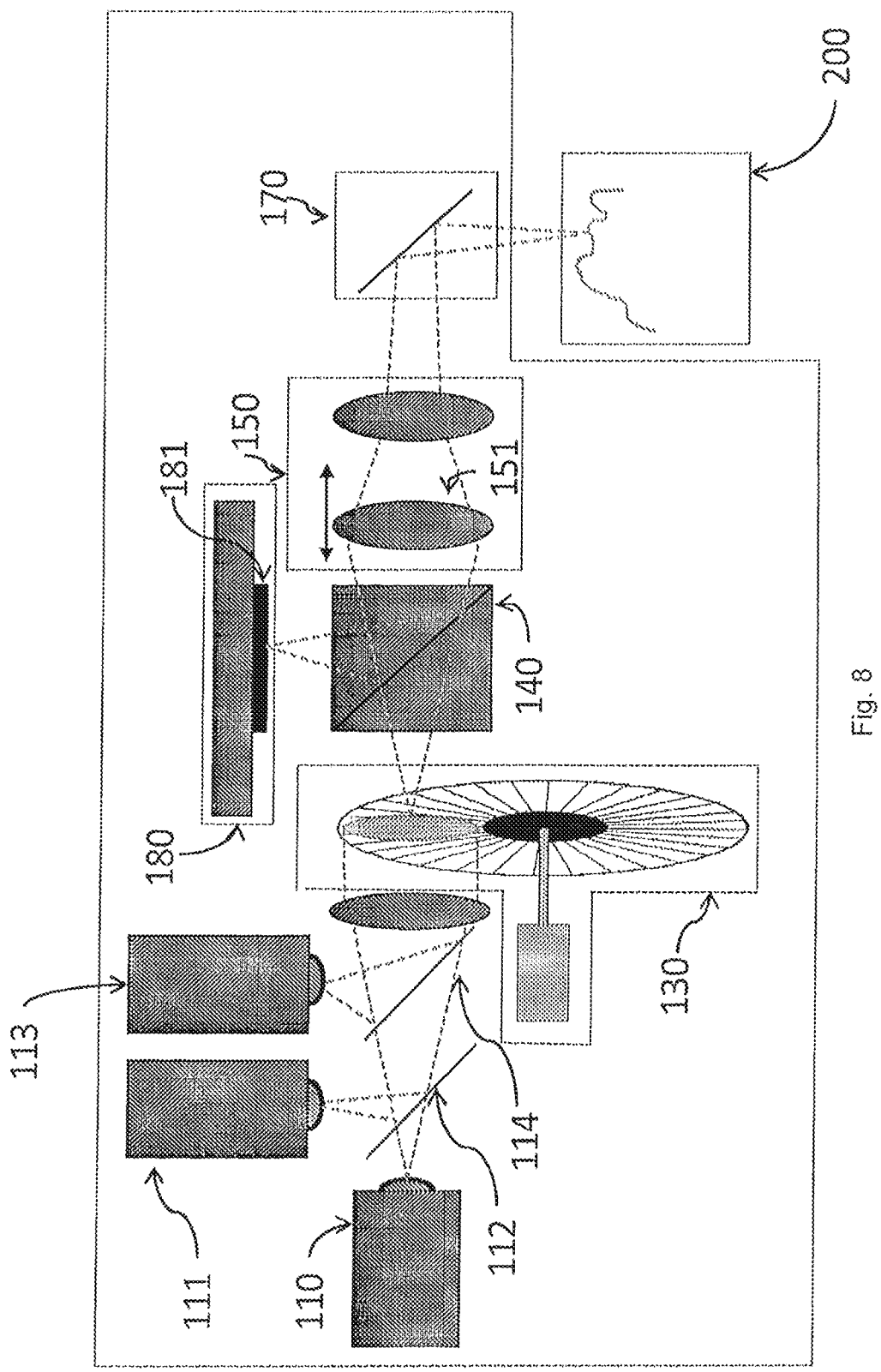
FIG. 8: A schematic presentation of an example embodiment of a device for simultaneous scanning of a surface shape and color.

An embodiment of a color 3D scanner is shown in FIG. 8. Three light sources 110, 111, and 113 emit red, green, and blue light. The light sources are may be LEDs or lasers. The light is merged together to overlap or essentially overlap. This may be achieved by means of two appropriately coated plates 112 and 114. Plate 112 transmits the light from 110 and reflects the light from 111. Plate 114 transmits the light from 110 and 111 and reflects the light from 113. The color measurement is performed as follows: For a given focus position the amplitude of the time-varying pattern projected onto the probed object is determined for each sensor element in the sensor 181 by one of the above mentioned methods for each of the light sources individually. In the preferred embodiment only one light source is switched on at the time, and the light sources are switched on after turn. In this embodiment the optical system 150 may be achromatic. After determining the amplitude for each light source the focus position is shifted to the next position and the process is repeated. The color expressed as e.g. an RGB color coordinate of each surface element can be reconstructed by appropriate weighting of the amplitude signal for each color corresponding the maximum amplitude.

One specific embodiment of the invention only registers the amplitude for all colors at an interval of P focus positions; while one color is selected for determination of the amplitude at all focus positions. P is a number which could be e.g. 3, 5, or 10. This results in a color resolution which is less than the resolution of the surface topology. Color of each surface element of the probed object is determined by interpolation between the focus positions where full color information is obtained. This is in analogy to the Bayer color scheme used in many color digital cameras. In this scheme the color resolution is also less than the spatial resolution and color information need to be interpolated.

A simpler embodiment of the 3D color scanner does not register full color information and employs only two light sources with different colors. An example of this is a dental scanner that uses red and blue light to distinguish hard (tooth) tissue from soft (gum) tissue.

Ear Scanner Embodiment

FIGS. 9-12D schematically illustrate an embodiment of a time-varying structured light illumination-based scanner for direct scanning of human ears by scanning both the exterior (outer) and interior (inner) part of a human ear by use of a common scanner exterior handle and a detachable probe. This embodiment is advantageous in that it allows for non-intrusive scanning using a probe designed to be inserted into small cavities, such as a human ear. This is done in part by positioning the bulky and essential parts of the scanner, such as the scanner camera, light source, electronics and focusing optics outside the closely confined part of the ear canal.

The ability to scan the outer and inner part of human ears and make a virtual or real model of the ear is essential in the design of modern custom-fitted hearing aid (e.g. ear shell or mold). Today, scanning of ears is performed in a two-step process where a silicone impression of the ear is taken first and the impression is subsequently scanned using an external scanner in a second step. The process of making the impression suffers from several drawbacks which will shortly be described in the following. One major drawback comes from frequent poor quality impressions taken by qualified clinic professionals due to the preparation and techniques required. Inaccuracies may arise because the impression material is known to expand during hardening and that deformation and creation of fractures in the impression are often created when the impression is removed from the ear. Another drawback is related to health risks involved with taking the impression due to irritation and allergic responses, damage to the tympanic membrane and infections. Finally, the impression process is an uncomfortable experience for many patients, especially for young children, who often require impressions taken at regular intervals (e.g. every four months) to accommodate the changing dimensions of the ear canal. In short, these drawbacks can be overcome if it is possible to scan the outer and inner ear in a non-intrusive way and obtain a registration between the inner and outer ear surfaces.

Figure 9:
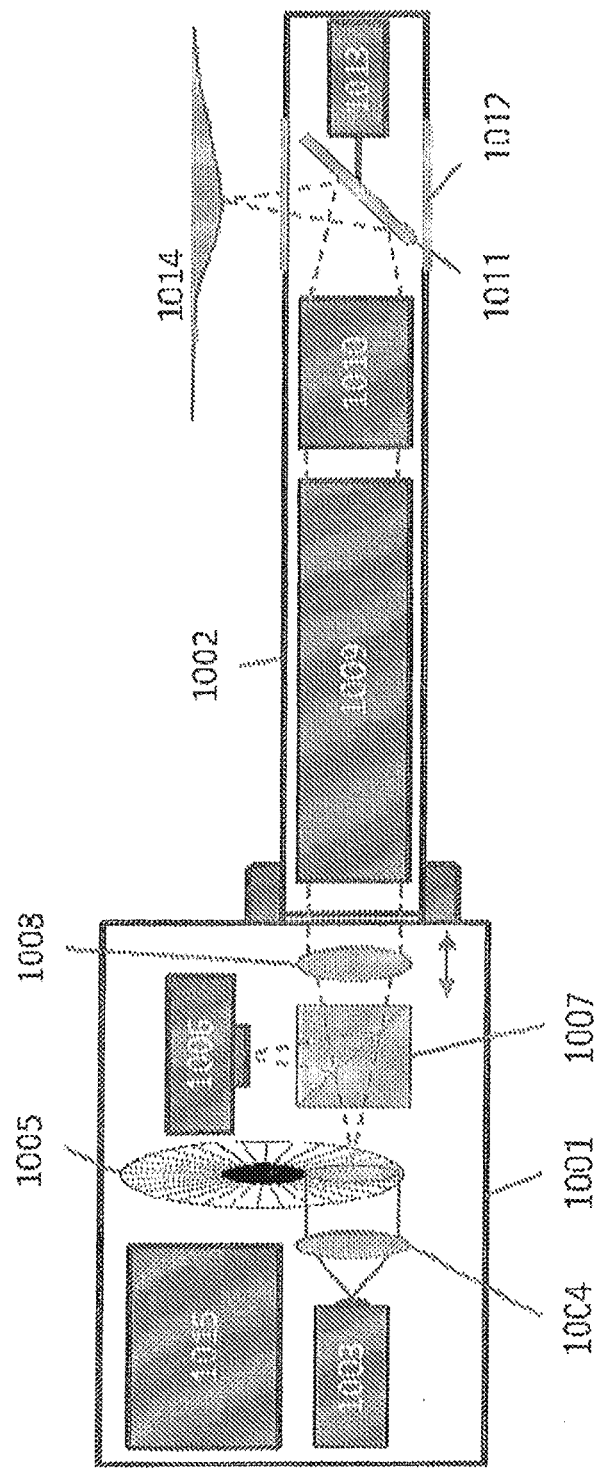
FIG. 9: A schematic presentation of an example embodiment of a device for scanning the at least a part of the external part of the human ear and/or a part of the ear canal of a human ear.
Figure 11:
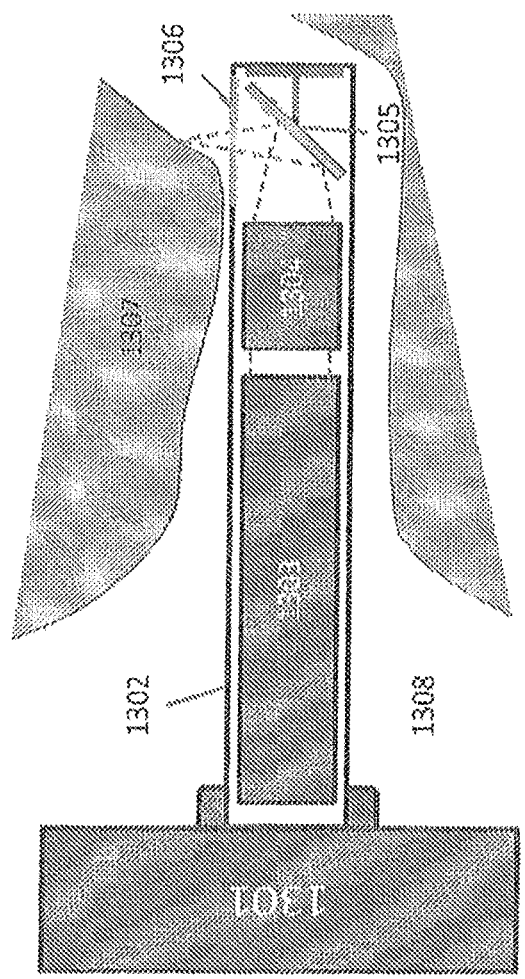
FIG. 11: Schematic of a scanner probe embodiment used to scan a narrow body cavity, such as a human ear.
Figure 12:
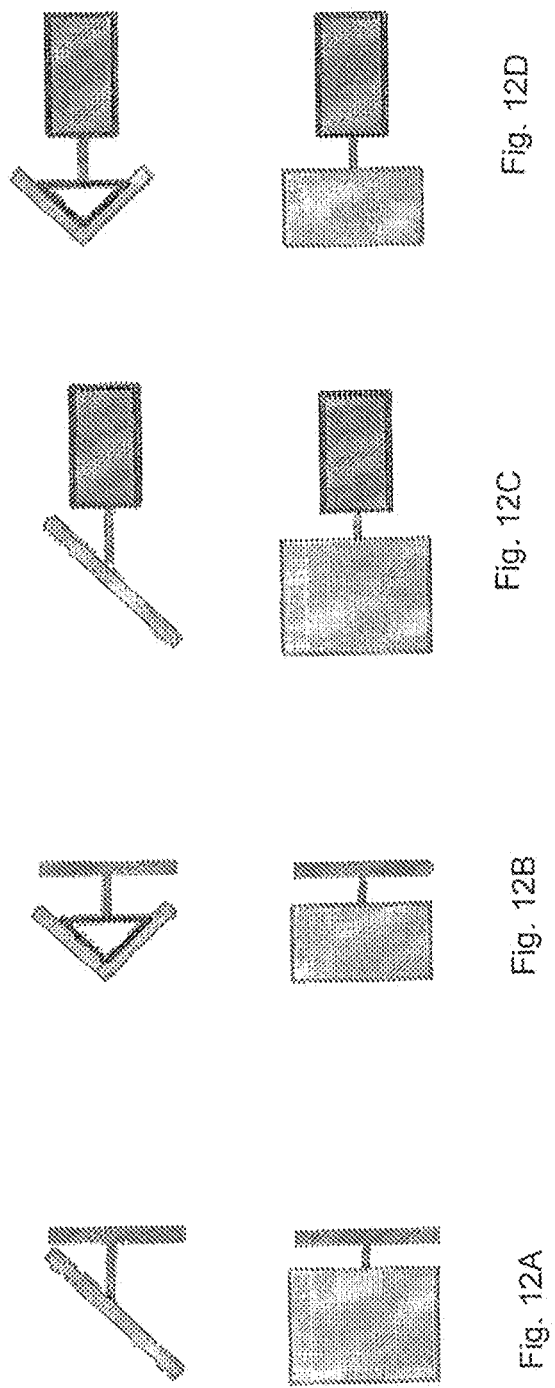
FIGS. 12A through 12D: Examples of mirror configurations to be used with a scanner probe.
Figure 13:
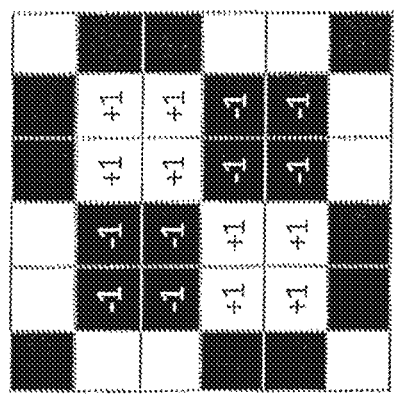
FIG. 13: A schematic representation of the reference signal values/weight values per pixel for a checkerboard pattern in an idealized optical system.

The following is not restricted to ear scanning but can be used to scan any small bodily cavity. FIG. 9 is a schematic of an embodiment of such a scanner. The scanner consists of two main parts—a scanner exterior 1001 and a scanner probe 1002. The scanner exterior may be used without the probe to obtain a larger field-of-view needed e.g. to scan the exterior part of the ear 1102, or the first part of the ear canal up to the first bend. The large field-of-view of the scanner exterior is important to obtain good registration between individual sub-scans and high global accuracy. By attaching a scanner probe 1002 to the scanner exterior 1001, the combined scanner allows for scanning of small and bent cavity surfaces, such as the interior part of an ear 1203. In this way and using the same system, the combined scanner exterior and probe are able to both scan larger external areas along with smaller internal areas.

In FIG. 9 the exterior part of the scanner embodiment 1001 consists of a diverging light source 1003 (laser, LED, Tungsten or another type) which is collimated using collimation optics 1004. The collimated light is used to illuminate a transparent object 1005 (e.g. glass) with an opaque pattern, e.g. fringes on it. The pattern is subsequently imaged onto the object to be scanned using a suitable optical system. The pattern is observed using a similar optical system and a camera 1006, where the latter is positioned outside the cavity. The 3D information is obtained from the 2D images by observing the light oscillation created by the movement of the pattern across the scan object as contained in the individual pixel amplitude.

To facilitate movement of the pattern, the fringe pattern 1005 is rotating in one embodiment. In another embodiment, the fringe pattern is positioned on a translating plate that moves in a plane perpendicular to the optical axis with a certain oscillation frequency. The light to and from the scan object is projected through a beam splitter arrangement 1007, which consists of a prism cube in one embodiment and in another embodiment consists of an angled plate or membrane. The beam splitter serves to transmit the source light further down the system, while at the same time guide the reflected light from the scan object back to the camera, which is positioned on an axis perpendicular to the axis of the light source and beam splitter.

To move the focus plane the scanner exterior includes focusing optics, which in one embodiment consists of a single movable lens 1008. The purpose of the focusing optics is to facilitate movement of the plane of focus for the whole imaging system in the required scanning range and along the optical axis. In one embodiment, the focusing optics of the scanner exterior 1101 includes an objective that can focus the light directly, without any use of additional optics, as shown in FIG. 10A. In another embodiment, the scanner exterior is supplied with a wide-angle objective designed with a large field-of-view, e.g. sufficiently large for scanning the exterior part of a human ear 1102.

The optical part of the scanner probe consists of an endoscopic optical relay system 1009 followed by a probe objective 1010, both of which are of sufficiently small diameter to fit into the canal of a human ear. These optical systems may consist of both a plurality of optical fibers and lenses and serve to transport and focus the light from the scanner exterior onto the scan object 1014 (e.g. the interior surface of an ear), as well as to collimate and transport the reflected light from the scan object back to the scanner exterior. In one embodiment, the probe objective provides telecentric projection of the fringe pattern onto the scan object. Telecentric projection can significantly ease the data mapping of acquired 2D images to 3D images. In another embodiment, the chief rays (center ray of each ray bundle) from the probe objective are diverging (non-telecentric) to provide the camera with an angle-of-view larger than zero, as shown in FIG. 9.

The position of the focus plane is controlled by the focusing optics 1008 and can be moved in a range large enough to at least coincide with the scan surface 1014. A single sub-scan is obtained by collecting a number of 2D images at different positions of the focus plane and at different positions of the fringe pattern, as previously described. As the focus plane coincides with the scan surface at a single pixel position, the fringe pattern will be projected onto the surface point in-focus and with high contrast, thereby giving rise to a large variation, or amplitude, of the pixel value over time. For each pixel it is thus possible to identify individual settings of the focusing optics for which each pixel will be in-focus. By using knowledge of the optical system, it is possible to transform the contrast information vs. position of the focus plane into 3D surface information, on an individual pixel basis.

In one embodiment, a mirror arrangement 1011, consisting of a single reflective mirror, or prism, or an arrangement of mirrors, are located after the probe objective 1010. This arrangement serves to reflect the rays to a viewing direction different from that of the of the probe axis. Different example mirror arrangements are found in FIGS. 12A-12D. In one particular embodiment, the angle between the mirror normal and the optical axis is approximately 45 degrees, thus providing a 90 degree view with respect to the probe axis—an arrangement ideal for looking round corners. A transparent window 1012 is positioned adjacent to the mirror and as part of the probe casing/shell, to allow the light to pass between the probe and the scan object, while keeping the optics clean from outside dirt particles.

To reduce the probe movement required by a scanner operator, the mirror arrangement may be rotated using a motor 1013. In one embodiment, the mirror arrangement rotates with constant velocity. By full rotation of a single mirror, it is in this way possible to scan with 360 degree coverage around the probe axis without physically moving the probe. In this case, the probe window 1012 is required to surround/go all around the probe to enable viewing in every angle. In another embodiment, the mirror rotates with a certain rotation oscillation frequency. In yet another embodiment, the mirror arrangement tilt with respect to the probe axis is varied with a certain oscillation frequency.

A particular embodiment uses a double mirror instead of a single mirror (FIGS. 12B and 12D). In a special case, the normal of the two mirrors are angled approx. 90 degrees with respect to each other. The use of a double mirror helps registration of the individual sub-scans, since information of two opposite surfaces in this way is obtained at the same time. Another benefit of using a double mirror is that only 180 degrees of mirror rotation is required to scan a full 360 degrees. A scanner solution employing double mirrors may therefore provide 360 degrees coverage in less time than single mirror configurations.

"Pistol-Like" Grip

Figure 17:
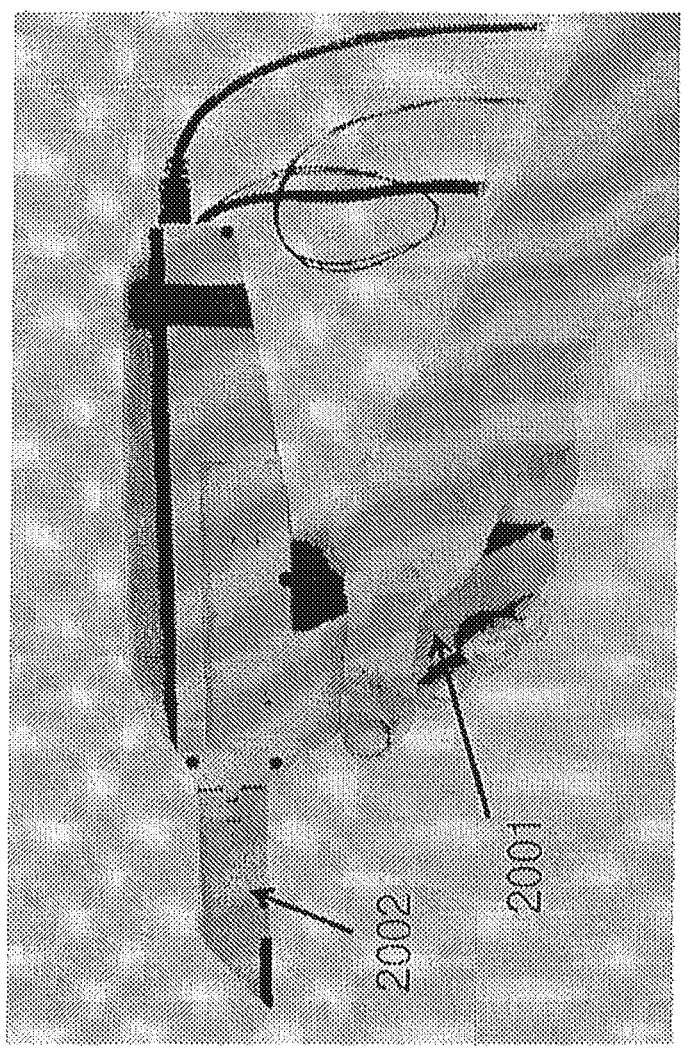
FIG. 17: Example of a handheld intraoral scanner with a pistol-like grip and a removable tip.

FIG. 17 shows an embodiment of the scanner with a pistol-like grip 2001. This form is particularly ergonomic. The scanner in FIG. 17 is designed for intra-oral scanning of teeth. The tip 2002 can be removed from the main body of the scanner and can be autoclaved. Furthermore, the tip can have two positions relative to the main body of the scanner, namely looking down (as in FIG. 17) and looking up. Therefore, scanning the upper and the lower mouth of a patient is equally comfortable for the operator. Note that the scanner shown in FIG. 17 is an early prototype with several cables attached for testing purposes only.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

Embodiment

1. A scanner for determining the 3D geometry and color of at least a part of the surface of an object, said scanner comprising:
    at least one camera accommodating an array of sensor elements,
    a light source for generating a probe light,
        an optical system for transmitting the probe light towards the object along an optical path thereby illuminating at least a part of the object in a plurality of configurations and for transmitting at least a part of the light returned from the object to the at least one camera,
        wherein the plurality of configurations is in the form of a time-varying illumination pattern, such that the 3D geometry is determined based on the time-varying illumination pattern, and
        a hardware processor configured to:
        selectively switch a color of the probe light, thereby illuminating the object with different colors at different times,
        record different images by the at least one camera at the different times, thereby recording images of the object with the different colors, and
        combine the different colors from the different images, thereby obtaining the color of the surface of the object.

The invention claimed is:

1. A handheld intraoral scanner for determining a 3D geometry of an object in an oral cavity, the intraoral scanner comprising:
    a tip configured to be inserted into the oral cavity;
    at least one camera accommodating an array of sensor elements;
    a pattern generator configured to generate, using a light source, a static pattern or a time-varying illumination pattern; and
    an optical system configured to transmit the static pattern or the time-varying illumination pattern, via the tip, towards the object along an optical path thereby illuminating at least a part of the object with the static pattern or the time-varying illumination pattern, and to transmit at least a part of the light returned from the object to the at least one camera to form a plurality of 2D images, wherein the plurality of 2D images is configured to determine a 3D geometry; and
    wherein the handheld intraoral scanner is wireless.

2. The handheld intraoral scanner according to claim 1, wherein the at least one camera is a high-speed camera.

3. The handheld intraoral scanner according to claim 1, wherein the static pattern or the time-varying illumination pattern is a time-varying illumination pattern.

4. The handheld intraoral scanner according to claim 1, comprising one or more motion sensors located on the intraoral scanner to measure three-dimensional motion of the handheld intraoral scanner.

5. The handheld intraoral scanner according to claim 1, wherein the handheld intraoral scanner is configured to enter a calibration mode in which images of an object of known geometry are recorded.

6. The handheld intraoral scanner according to claim 1, further comprising a hardware processor, located within the wireless intraoral scanner, configured to process the plurality of 2D images, and transmit, via a wireless connection, the processed plurality of 2D images in real time.

7. The handheld intraoral scanner according to claim 1, wherein the light source is a white light source, and wherein the at least one camera accommodates a Bayer color filter.

8. The handheld intraoral scanner according to claim 1, further comprising a hardware processor configured to locally process raw 3D data into data for the 3D geometry, such that the data for the 3D geometry is wirelessly transmitted instead of the raw 3D data, and wherein the raw 3D data is based on the plurality of 2D images.

9. The handheld intraoral scanner according to claim 8, wherein the hardware processor processes the raw 3D data into data for the 3D geometry in real time.

10. The handheld intraoral scanner according to claim 1, wherein the optical system is configured to backward ray tracing to estimate a 2D to 3D mapping.

11. The handheld intraoral scanner according to claim 1, wherein the static pattern or the time-varying illumination pattern is a static pattern.

12. The handheld intraoral scanner according to claim 11, wherein the static pattern is a static line pattern, a static checkerboard pattern, or a planar checkboard pattern.

13. A handheld intraoral scanner for determining a 3D geometry of an object in an oral cavity, the intraoral scanner comprising:
    a tip configured to be inserted into the oral cavity;
    at least one camera accommodating an array of sensor elements;
    a pattern generator configured to generate, using a light source, a probe light with a plurality of configurations in the form of a static pattern or a time-varying illumination pattern; and
    an optical system configured to transmit the probe light, via the tip, towards the object along an optical path thereby illuminating at least a part of the object with the static pattern or the time-varying illumination pattern, and to transmit at least a part of the light returned from the object to the at least one camera to form a plurality of 2D images, wherein the plurality of 2D images is configured to determine a 3D geometry; and wherein the handheld intraoral scanner is wireless.

14. The handheld intraoral scanner according to claim 13, wherein heat generated in the handheld intraoral scanner is used to warm the probe light such that no or less condensation occurs on the probe light when the probe light is inside the oral cavity.

15. The handheld intraoral scanner according to claim 13, further comprising a hardware processor configured to: selectively switch a color of the probe light, thereby illuminating the object with different colors at different times; record different images by the at least one camera at the different times, thereby recording images of the object with the different colors; and combine the different colors from the different images, thereby obtaining the color of the surface of the object.

16. The handheld intraoral scanner according to claim 15, wherein the different colors are provided by at least three monochromatic light sources of the light source.

17. The handheld intraoral scanner according to claim 13, wherein the probe light is directed towards the object in a direction substantially parallel with the longitudinal axis of the tip, and wherein the probe light is further reflected towards the object by a single reflective mirror located in the tip.

18. The handheld intraoral scanner according to claim 13, wherein the probe light is autoclavable.

19. The handheld intraoral scanner according to claim 13, wherein the probe light is a tip with a smaller height than a scan length.

* * * * *